(12) United States Patent
Saba et al.

(10) Patent No.: US 7,674,580 B2
(45) Date of Patent: Mar. 9, 2010

(54) COMPOSITIONS AND METHODS FOR THE MODULATION OF SPHINGOLIPID METABOLISM AND/OR SIGNALING

(75) Inventors: Julie D Saba, Oakland, CA (US); Henrik Fyrst, Alameda, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 798 days.

(21) Appl. No.: 10/348,052

(22) Filed: Jan. 17, 2003

(65) Prior Publication Data

US 2003/0219782 A1 Nov. 27, 2003

Related U.S. Application Data

(63) Continuation-in-part of application No. 10/053,510, filed on Jan. 17, 2002, now Pat. No. 6,830,881.

(60) Provisional application No. 60/349,582, filed on Jan. 17, 2002.

(51) Int. Cl.
*C12Q 1/68* (2006.01)
*C07H 21/04* (2006.01)
*C07H 21/02* (2006.01)
*C12P 19/34* (2006.01)

(52) U.S. Cl. .................... 435/6; 435/91.2; 536/23.1; 536/24.31

(58) Field of Classification Search ............. None
See application file for complete search history.

(56) References Cited

U.S. PATENT DOCUMENTS

| | | | | |
|---|---|---|---|---|
| 5,430,169 | A | 7/1995 | Boumendjel et al. | 558/169 |
| 6,187,562 | B1 | 2/2001 | Duckworth et al. | 435/69.1 |
| 6,423,527 | B1 | 7/2002 | Saba et al. | 435/232 |
| 6,858,427 | B2 * | 2/2005 | Gerritsen et al. | 435/325 |
| 2003/0054366 | A1 * | 3/2003 | Schlegel et al. | 435/6 |
| 2003/0215805 | A1 * | 11/2003 | Lillie et al. | 435/6 |
| 2004/0005563 | A1 * | 1/2004 | Mack et al. | 435/6 |
| 2004/0029114 | A1 * | 2/2004 | Mack et al. | 435/6 |
| 2004/0110197 | A1 * | 6/2004 | Skinner et al. | 435/6 |
| 2005/0221346 | A1 * | 10/2005 | Saba et al. | 435/6 |
| 2006/0252035 | A1 * | 11/2006 | Friedman et al. | 435/6 |

FOREIGN PATENT DOCUMENTS

| | | | |
|---|---|---|---|
| WO | WO 93/19760 | | 10/1993 |
| WO | WO 95/21848 | | 8/1995 |
| WO | WO 99/16888 | * | 4/1999 |
| WO | WO 99/38983 | | 8/1999 |
| WO | WO 99/61581 | A2 | 12/1999 |
| WO | WO 00/70028 | A1 | 11/2000 |
| WO | WO 01/31029 | A2 | 5/2001 |
| WO | WO 01/42479 | | 6/2001 |
| WO | WO 0149879 | A2 * | 7/2001 |
| WO | WO 01/85953 | A1 | 11/2001 |
| WO | WO 0227028 | A1 * | 4/2002 |

OTHER PUBLICATIONS

Amalfitano et al. Fluorescence in situ hybridization study of aneuploidy of chromosomes 7, 10, X, and Y in primary and secondary glioblastomas. 2000. Cancer Genet Cytogenet. vol. 116, pp. 6-9.*
Genbank entry GI:5532486. Apr. 20, 1999.*
Genbank entry GI:8133099. May 11, 2000.*
Pyne et al. Sphingosine 1-phosphate signalling in mammalian cells. 2000. Biochem J. vol. 349, pp. 385-402.*
Thompson et al. p53 gene mRNA expression and chromosome 17p allele loss in breast cancer. 1990. Br J Cancer. vol. 61, pp. 74-78.*
Bejaoui et al. SPTLC1 is mutated in hereditary sensory neuropathy, type 1. Nat Genet. Mar. 2001;27(3):261-2.*
Dawkins et al. Mutations in SPTLC1, encoding serine palmitoyltransferase, long chain base subunit-1, cause hereditary sensory neuropathy type I. Nat Genet. Mar. 2001;27(3):309-12.*
Gable et al. Mutations in the yeast LCB1 and LCB2 genes, including those corresponding to the hereditary sensory neuropathy type I mutations, dominantly inactivate serine palmitoyltransferase. J Biol Chem. Mar. 22, 2002;277(12):10194-200. Epub Jan. 7, 2002.*
Xia et al. An oncogenic role of sphingosine kinase. Curr Biol. Nov. 30, 2000;10(23):1527-30.*
Ioannidis (Nature genetics (2001) 29:306-309).*
Lucentini et al (The Scientist (2004) vol. 18).*
Wacholder et al (J. Natl. Cancer Institute (2004) 96(6):434-442).*
Oskouian et al (PNAS (2006) 103(46): 17384-17389).*
GenBank GI:1855648 [online] Aug. 1997 [retrieved on Apr. 2, 2009], retrieved from http://www.ncbi.nlm.nih.gov/nucest/1855648?report=est&log$=seqview.*
Adachi-Yamada, T. et al., "De Novo Synthesis of Sphingolipids Is Required for Cell Survival by Down-Regulating c-Jun N-Terminal Kinase in *Drosophila* Imaginal Discs," *Molecular and Cellular Biology 19*(10): 7276-7286, Oct. 1999.
Caligan, T.B. et al., "A High-Performance Liquid Chromatographic Method to Measure Sphingosine 1-Phosphate and Related Compounds from Sphingosine Kinase Assays and Other Biological Samples," *Analytical Biochemistry 281*(1): 36-44, May 15, 2000.
Fryst, H. et al., "The *PLB2* Gene of *Saccharomyces cerevisiae* Confers Resistance to Lysophophatidylcholine and Encodes a Phospholipase B/Lysophospholipase," *Biochemistry 38*(18): 5864-5871, May 4, 1999.
Gottlieb, D. et al., "The *DPL1* Gene Is Involved in Mediating the Response to Nutrient Deprivation in *Saccharomyces cerevisiae*," *Molecular Cell Biology Research Communications 1*(1): 66-71, Apr. 1999.

(Continued)

*Primary Examiner*—Young J Kim
*Assistant Examiner*—Samuel C Woolwine
(74) *Attorney, Agent, or Firm*—Seed IP Law Group PLLC

(57) ABSTRACT

Compositions, methods and kits for diagnosing and treating cancer and muscular disorders are provided. Therapeutic compositions may comprise agents that modulate sphingolipid metabolism and/or signaling pathways. Such compositions may be administered to a mammal afflicted with cancer. Diagnostic methods and kits may employ an agent suitable for detecting alterations in endogenous genes involved in sphingolipid metabolism. Such methods and kits may be used to detect the presence of a cancer or to evaluate the prognosis of a known disease. SPL polypeptides, polynucleotides and antibodies are also provided.

1 Claim, 3 Drawing Sheets

OTHER PUBLICATIONS

Hannun, Y.A. et al., "Enzymes of Sphingolipid Metabolism: From Modular to Intergrative Signaling," *Biochemistry 40*(16): 4893-4903, Apr. 24, 2001.

Heitman, J. et al., "FK 506-binding protein proline rotamase is a target for the immunosuppressive agent FK 506 in *Saccharomyces cerevisiae*," *Proc. Natl. Acad. Sci. USA 88*: 1948-1952, Mar. 1991.

Herr, D.R. et al., "*Sply* regulation of sphingolipid signaling molecules is essential for *Drosophila* development," *Development 130*: 2443-2453, 2003.

Kim, S. et al., "Accumulation of Phosphorylated Sphingoid Long Chain Bases Results in Cell Growth Inhibition in *Saccharomyces cerevisiae*," *Genetics 156*: 1519-1529, Dec. 2000.

Lanterman and Saba, "Characterization of sphingosine kinase (SK) acitivity in *Saccharomyces cerevisiae* and isolation of SK-deficient mutants," *Biochem. J. 332*: 525-531, 1998.

Mao, C. et al., "The dihydrosphingosine-1-phosphate phosphatases of *Saccharomyces cerevisiae* are important regulators of cell proliferation and heat stress responses," *Biochem. J. 342*: 667-675, 1999.

Melendez, A.J. et al., "Human sphingosine kinase: molecular cloning, functional characterization and tissue distribution," *Gene 251*: 19-26, 2000.

Mendel, J. et al., "Sphingosine Phosphate Lyase Expression Is Essential for Normal Development in *Caenorhabditis elegans*," *The Journal of Biological Chemistry 278*(25): 22341-22349, Jun. 20, 2003.

Olivera and Spiegel, "Sphingosine-1-phosphate as second messenger in cell proliferation induced by PDGF and FCS mitogens," *Nature 365*: 557-560, Oct. 7, 1993.

Pyne and Pyne, "Sphingosine 1-phosphate signalling via the endothelial differentiation gene family of G-protein-coupled receptors," *Pharmacology & Therapeutics 88*: 115-131, 2000.

Roseman, R.R. et al., "A *P* Element Containing *suppressor of Hairy-wing* Binding Regions Has Novel Properties for Mutagenesis in *Drosophila melanogaster*," *Genetics 141*: 1061-1074, Nov. 1995.

Saba, J. et al., "Ceramide: an intracellular mediator of apopotosis and growth suppression," *Phil. Trans. R. Soc. Lond. B 351*: 233-244, 1996.

Saba, J.D. et al., "The *BST1* Gene of *Saccharomyces cerevisiae* Is the Sphingosine-1-phosphate Lyase," *The Journal of Biological Chemistry 272*(42): 26087-26090, Oct. 17, 1997.

Van Veldhoven and Mannaerts, "Subcellular Localization and Membrane Topology of Sphingosine-1-phosphate Lyase in Rat Liver," *The Journal of Biological Chemistry 266*(19): 12502-12507, Jul. 5, 1991.

Van Veldhoven, P.P. et al., "Human sphingosine-1-phosphate lyase: cDNA cloning, functional expression studies and mapping to chromosome 10q22," *Biochimica et Biophysica Acta 1487*: 128-134, 2000.

Zhou and Saba, "Identification of the First Mammalian Sphingosine Phosphate Lyase Gene and Its Functional Expression in Yeast," *Biochemical and Biophysical Research Communications 242*(3): 502-507, Jan. 26, 1998.

Adams et al., GenBank Accession No. AA338781, Apr. 18, 1997.

Amann et al., "Tightly regulated tac promoter vectors useful for the expression of unfused and fused proteins in *Escherichia coli*," *Gene 69*(2):301-315, Sep. 30, 1988.

Branden et al., "Prediction, Engineering, and Design of Protein Structures," Introduction to Protein Structure, Garland Publishing, Inc., New York, p. 247, 1991.

Broun et al., "Catalytic Plasticity of Fatty Acid Modification Enzymes Underlying Chemical Diversity of Plant Lipids," *Science 282*:1315-1317, Nov. 13, 1998.

Fulton, GenBank Database, Accession No. U51031, Mar. 23, 1996.

Fulton, GenBank Database, Accession No. S70123, May 1996.

Hillier et al., GenBank Database, Accession No. T86263, Mar. 30, 1995.

Ikeda et al., "Sphingosine-1-phosphate lyase SPL is an endoplasmic reticulum-resident, integral membrane protein with the pyridoxal 5'-phosphate binding domain exposed to the cytosol," *Biochemical and Biophysical Research Communications 325*:338-343, 2004.

Kohara, GenBank Database, Accession No. D66593, Dec. 13, 1995.

Marra et al., GenBank Database, Accession No. AA107456, Nov. 6, 1996.

Marra et al., GenBank Database, Accession No. AA589412, Sep. 18, 1997.

Marra et al., GenBank Database, Accession No. WO8172, Sep. 5, 1996.

Qie et al., "Identification of a Saccaromyces Gene, LCB3, Necessary for Incorporation of Exogenous Long Chain Bases into Sphingolipids," *J. Biol. Chem., 272*(26):16110-16117, Jun. 27, 1997.

Reiss et al., "Sphingosine-phosphate Lyase Enhances Stress-induced Ceramide Generation and Apoptosis," *J. Biol. Chem. 279*(2):1281-1290, 2004.

Sadahira et al., Sphingosine 1-phosphate, a specific endogenous signaling molecule controlling cell motility and tumor cell invasiveness, *Proc. Natl. Acad. Sci. USA 89*(20:9686-9690, Oct. 15, 1992.

Seffernick et al., "Melamine Deaminase and Atrazine Chlorohydrolase: 98 Percent Identical but Functionally Different," *J. Bacteriol. 183*(8):2405-2410, Apr. 2001.

Spiegel et al., "Sphingosine-1-phosphate, a novel second messenger involved in cell growth regulation and signal transduction, affects growth and invasiveness of human breast cancer cells," *Breast Cancer Research and Treatment 31*:337-348, 1994.

van de Loo et al., "An oleate 12-hydroxylase from Ricinus communis L. is a fatty acyl desaturase homolog," *Proc. Natl. Acad. Sci. USA 92*:6743-6747, Jul. 1995.

Van Veldhoven et al., "Sphingosine-Phosphate Lyase," *Advances in Lipid Research 26*:69-98, 1993.

Waterston, GenBank Database, Accession No. AAC69001, Oct. 22, 1998.

Witkowski et al., "Conversion of a β-Ketoacyl Synthase to a Malonyl Decarboxylase by Replacement of the Active-Site Cysteine with Glutamine," *Biochemistry 38*(36):11643-11650, 1999.

\* cited by examiner

Potential Drosophila SK Genes

```
             181        195 196       210 211       225 226       240 241       255 256       270
1 DSK1747    FRSSNDYGWNLQTAE MAHHTIRKHKR---- -GNGSSSPADCGKQL LILLNPKSGSGKGRE LFQKQVAPLLTEAEV QYDLQITTHPQYAKE   235
2 DSK2159    FRSFDTFEDNMREAD RWYRSLRWQLHRTLE EIFVAPTVDERRRV LVLLNPKSGSGDARE VFNMHVTPVLNEAEV PYDLYVTKHSNFAIE   262
3 HSPHK1                                                 --V LVLLNPRGGKGKALQ LFRSHVQPLLAEAEI SFTLMLTERRNHARE    62

271        285 286       300 301       315 316       330 331       345 346       360
1 DSK1747    FVRTRRDLLTRYSGI VVASGDGLFYEVLNG LMERMDWKRACRELP LGIIPCGSGNGLAKS VAHHCNEPYEPKPIL HATLTCMAGK--STP   324
2 DSK2159    FLSTR--CLDAWCCV VAVGDGLFHEIVNG LLQRQDWAHVLPHLA LGIIPCGSGNGLARS IAHCYNK----PVL GAALTVISGR--SSP   343
3 HSPHK1     LVRSE--ELGRWDAL VVWSGDGLYMHEVVNG LMERPDWETAIQKP- LCSLPAGSGNALAAS LNHYAGYEQVTNEDL LTNCTLLLCRRLLSP   149

361        375 376       390 391       405 406       420 421       435 436       450
1 DSK1747    MDVWRVELATRDKHF VMYSFLSVGWGLIAD IDIESERLRSIGAQR FTLMAIKRLIGLRSY KGRVSYLLGKGKKEP PVEAARELPAESTAA   414
2 DSK2159    MDVWRVQLQSRS--- -LYSFLSIGMGLISD VDIESERIRMLGYQR FTWTLYRLVNLRTY NGRISYLLTDHEVSS -THSATGYAAQRRMQ   428
3 HSPHK1     MNLLSLHTASGLR-- -LFSVLSLAWGFTAD VDLESEKYRRLGEMR FTLGTFLRLAALRTY RGRLAYLPVGRVGSK ---TPASPVVQ---   230

451        465 466       480 481       495 496       510 511       525 526       540
1 DSK1747    GIRSSLPLNAGEFHD LPEEEEGEAVLDGEQ FADAISLDRSV---Y RQHADSWHSAMSRRT AYYSLGGPSMPSNRS RMSISQRIEAANAEF   501
2 DSK2159    SSRSCNTHIDMLNGP APIYHSSAEYLP-QE FADVISLETSINQSF RSRCDSMLSGGSRRS FYYSIS-ESIYHSLA DESEFAGLAAASLEN   516
3 HSPHK1     -QGPVDAHLVPLEEP VP--------------                                                                 246

541        555 556       570 571       585 586       600 601       615 616       630
1 DSK1747    AER--VPTGTIPPLQ MPLLSSDGMICEDGD FVMWHAAYTTHLSSD VFFAPESRLDDGLIY LVIIRRGVSRHOLLN FVLNLNAGTHLPIGE   589
2 DSK2159    RQQNYGPASELPDLN EPLSEDQGMLVEEGE FVMWHAVYQTHLGID CHFAPKAQLNDGTIY LILIRAGISRPHLLS FLYNMSSGTHLPESH   606
3 HSPHK1     --------SHMTVVPDED FVLVLALLHSHLGSE MFAAPMGRCAAGVMH LFYVRAGVSRAMLLR LFLAMEKGRHMEY-E   315

631        645 646       660 661       675 676       690 691       705 706       720
1 DSK1747    DPFIKVWPCRAFRIE PSSSDGILLVVDGERV EYGPIQAEVMPGLIN WMTTSGQ--------                                  641
2 DSK2159    DDHVKVLPVRAFRLE PYDNHGIITVDGERV EFGPLQAEVLPGIAR VMVPNVSTFRFQSAT LQHGIPVCIPVRKRF VLYNMSSEELAPINE   696
3 HSPHK1     CPYLVYVPVWAFRLE PKDGKGVFAVDGELM VSEAVQGQVHPNYFW MVSGCVEPP--PSWK PQQMPPPEEPL----                   384
```

Fig. 1

Scheme 1

SEQUENCE LISTING

```
<160> NUMBER OF SEQ ID NOS: 29

<210> SEQ ID NO 1
<211> LENGTH: 1770
<212> TYPE: DNA
<213> ORGANISM: S. cerevisiae
<220> FEATURE:
<221> NAME/KEY: CDS
<222> LOCATION: (1)...(1770)

<400> SEQUENCE: 1 atg agt gga gta tca aat aaa aca gta tca att aat ggt tgg tat ggc      48
Met Ser Gly Val Ser Asn Lys Thr Val Ser Ile Asn Gly Trp Tyr Gly
1               5                   10                  15 atg cca att cat tta cta agg gaa gaa ggc gac ttt gcc cag ttt atg      96
Met Pro Ile His Leu Leu Arg Glu Glu Gly Asp Phe Ala Gln Phe Met
            20                  25                  30 att cta acc atc aac gaa tta aaa ata gcc ata cat ggt tac ctc aga     144
Ile Leu Thr Ile Asn Glu Leu Lys Ile Ala Ile His Gly Tyr Leu Arg
        35                  40                  45 aat acc cca tgg tac aac atg ttg aag gat tat ttg ttt gtg atc ttt     192
Asn Thr Pro Trp Tyr Asn Met Leu Lys Asp Tyr Leu Phe Val Ile Phe
    50                  55                  60 tgt tac aag cta ata agt aat ttt ttt tat ctg ttg aaa gtt tat ggg     240
Cys Tyr Lys Leu Ile Ser Asn Phe Phe Tyr Leu Leu Lys Val Tyr Gly
65                  70                  75                  80 ccg gtg agg tta gca gtg aga aca tac gag cat agt tcc aga aga ttg     288
Pro Val Arg Leu Ala Val Arg Thr Tyr Glu His Ser Ser Arg Arg Leu
                85                  90                  95 ttt cgt tgg tta ttg gac tca cca ttt ttg agg ggt acc gta gaa aag     336
Phe Arg Trp Leu Leu Asp Ser Pro Phe Leu Arg Gly Thr Val Glu Lys
            100                 105                 110 gaa gtc aca aag gtc aaa caa tcg atc gaa gac gaa cta att aga tcg     384
Glu Val Thr Lys Val Lys Gln Ser Ile Glu Asp Glu Leu Ile Arg Ser
        115                 120                 125 gac tct cag tta atg aat ttc cca cag ttg cca tcc aat ggg ata cct     432
Asp Ser Gln Leu Met Asn Phe Pro Gln Leu Pro Ser Asn Gly Ile Pro
    130                 135                 140
```

```
cag gat gat gtt att gaa gag cta aat aaa ttg aac gac ttg ata cca     480
Gln Asp Asp Val Ile Glu Glu Leu Asn Lys Leu Asn Asp Leu Ile Pro
145                 150                 155                 160 cat acc caa tgg aag gaa gga aag gtc tct ggt gcc gtt tac cac ggt     528
His Thr Gln Trp Lys Glu Gly Lys Val Ser Gly Ala Val Tyr His Gly
            165                 170                 175 ggt gat gat ttg atc cac tta caa aca atc gca tac gaa aaa tat tgc     576
Gly Asp Asp Leu Ile His Leu Gln Thr Ile Ala Tyr Glu Lys Tyr Cys
        180                 185                 190 gtt gcc aat caa tta cat ccc gat gtc ttt cct gcc gta cgt aaa atg     624
Val Ala Asn Gln Leu His Pro Asp Val Phe Pro Ala Val Arg Lys Met
    195                 200                 205 gaa tcc gaa gtg gtt tct atg gtt tta aga atg ttt aat gcc cct tct     672
Glu Ser Glu Val Val Ser Met Val Leu Arg Met Phe Asn Ala Pro Ser
210                 215                 220 gat aca ggt tgt ggt acc aca act tca ggt ggt aca gaa tcc ttg ctt     720
Asp Thr Gly Cys Gly Thr Thr Thr Ser Gly Gly Thr Glu Ser Leu Leu
225                 230                 235                 240 tta gca tgt ctg agc gct aaa atg tat gcc ctt cat cat cgt gga atc     768
Leu Ala Cys Leu Ser Ala Lys Met Tyr Ala Leu His His Arg Gly Ile
            245                 250                 255 acc gaa cca gaa ata att gct ccc gta act gca cat gct ggg ttt gac     816
Thr Glu Pro Glu Ile Ile Ala Pro Val Thr Ala His Ala Gly Phe Asp
        260                 265                 270 aaa gct gct tat tac ttt ggc atg aag cta cgc cac gtg gag cta gat     864
Lys Ala Ala Tyr Tyr Phe Gly Met Lys Leu Arg His Val Glu Leu Asp
    275                 280                 285 cca acg aca tat caa gtg gac ctg gga aaa gtg aaa aaa ttc atc aat     912
Pro Thr Thr Tyr Gln Val Asp Leu Gly Lys Val Lys Lys Phe Ile Asn
290                 295                 300 aag aac aca att tta ctg gtc ggt tcc gct cca aac ttt cct cat ggt     960
Lys Asn Thr Ile Leu Leu Val Gly Ser Ala Pro Asn Phe Pro His Gly
305                 310                 315                 320 att gcc gat gat att gaa gga ttg ggt aaa ata gca caa aaa tat aaa    1008
Ile Ala Asp Asp Ile Glu Gly Leu Gly Lys Ile Ala Gln Lys Tyr Lys
            325                 330                 335 ctt cct tta cac gtc gac agt tgt cta ggt tcc ttt att gtt tca ttt    1056
Leu Pro Leu His Val Asp Ser Cys Leu Gly Ser Phe Ile Val Ser Phe
        340                 345                 350 atg gaa aag gct ggt tac aaa aat ctg cca tta ctt gac ttt aga gtc    1104
Met Glu Lys Ala Gly Tyr Lys Asn Leu Pro Leu Leu Asp Phe Arg Val
    355                 360                 365 ccg gga gtc acc tca ata tca tgt gac act cat aaa tat gga ttt gca    1152
Pro Gly Val Thr Ser Ile Ser Cys Asp Thr His Lys Tyr Gly Phe Ala
370                 375                 380 cca aaa ggc tcg tca gtt ata atg tat aga aac agc gac tta cga atg    1200
Pro Lys Gly Ser Ser Val Ile Met Tyr Arg Asn Ser Asp Leu Arg Met
385                 390                 395                 400 cat cag tat tac gta aat cct gct tgg act ggc ggg tta tat ggc tct    1248
His Gln Tyr Tyr Val Asn Pro Ala Trp Thr Gly Gly Leu Tyr Gly Ser
            405                 410                 415 cct aca tta gca ggg tcc agg cct ggt gct att gtc gta ggt tgt tgg    1296
Pro Thr Leu Ala Gly Ser Arg Pro Gly Ala Ile Val Val Gly Cys Trp
        420                 425                 430 gcc act atg gtc aac atg ggt gaa aat ggg tac att gag tcg tgc caa    1344
Ala Thr Met Val Asn Met Gly Glu Asn Gly Tyr Ile Glu Ser Cys Gln
    435                 440                 445 gaa ata gtc ggt gca gca atg aag ttt aaa aaa tac atc cag gaa aac    1392
Glu Ile Val Gly Ala Ala Met Lys Phe Lys Lys Tyr Ile Gln Glu Asn
450                 455                 460
```

```
att cca gac ctg aat ata atg ggc aac cct aga tat tca gtc att tca    1440
Ile Pro Asp Leu Asn Ile Met Gly Asn Pro Arg Tyr Ser Val Ile Ser
465                 470                 475                 480 ttt tct tca aag acc ttg aac ata cac gaa cta tct gac agg ttg tcc    1488
Phe Ser Ser Lys Thr Leu Asn Ile His Glu Leu Ser Asp Arg Leu Ser
                485                 490                 495 aag aaa ggc tgg cat ttc aat gcc cta caa aag ccg gtt gca cta cac    1536
Lys Lys Gly Trp His Phe Asn Ala Leu Gln Lys Pro Val Ala Leu His
            500                 505                 510 atg gcc ttc acg aga ttg agc gct cat gtt gtg gat gag atc tgc gac    1584
Met Ala Phe Thr Arg Leu Ser Ala His Val Val Asp Glu Ile Cys Asp
        515                 520                 525 att tta cgt act acc gtg caa gag ttg aag agc gaa tca aat tct aaa    1632
Ile Leu Arg Thr Thr Val Gln Glu Leu Lys Ser Glu Ser Asn Ser Lys
    530                 535                 540 cca tcc cca gac gga act agc gct cta tat ggt gtc gcc ggg agc gtt    1680
Pro Ser Pro Asp Gly Thr Ser Ala Leu Tyr Gly Val Ala Gly Ser Val
545                 550                 555                 560 aaa act gct ggc gtt gca gac aaa ttg att gtg gga ttc cta gac gca    1728
Lys Thr Ala Gly Val Ala Asp Lys Leu Ile Val Gly Phe Leu Asp Ala
                565                 570                 575 tta tac aag ttg ggt cca gga gag gat acc gcc acc aag tag           1770
Leu Tyr Lys Leu Gly Pro Gly Glu Asp Thr Ala Thr Lys *
            580                 585

<210> SEQ ID NO 2
<211> LENGTH: 589
<212> TYPE: PRT
<213> ORGANISM: S. cerevisiae

<400> SEQUENCE: 2

Met Ser Gly Val Ser Asn Lys Thr Val Ser Ile Asn Gly Trp Tyr Gly
1               5                   10                  15

Met Pro Ile His Leu Leu Arg Glu Glu Gly Asp Phe Ala Gln Phe Met
                20                  25                  30

Ile Leu Thr Ile Asn Glu Leu Lys Ile Ala Ile His Gly Tyr Leu Arg
            35                  40                  45

Asn Thr Pro Trp Tyr Asn Met Leu Lys Asp Tyr Leu Phe Val Ile Phe
        50                  55                  60

Cys Tyr Lys Leu Ile Ser Asn Phe Phe Tyr Leu Leu Lys Val Tyr Gly
65                  70                  75                  80

Pro Val Arg Leu Ala Val Arg Thr Tyr Glu His Ser Ser Arg Arg Leu
                85                  90                  95

Phe Arg Trp Leu Leu Asp Ser Pro Phe Leu Arg Gly Thr Val Glu Lys
            100                 105                 110

Glu Val Thr Lys Val Lys Gln Ser Ile Glu Asp Glu Leu Ile Arg Ser
        115                 120                 125

Asp Ser Gln Leu Met Asn Phe Pro Gln Leu Pro Ser Asn Gly Ile Pro
    130                 135                 140

Gln Asp Asp Val Ile Glu Glu Leu Asn Lys Leu Asn Asp Leu Ile Pro
145                 150                 155                 160

His Thr Gln Trp Lys Glu Gly Lys Val Ser Gly Ala Val Tyr His Gly
                165                 170                 175

Gly Asp Asp Leu Ile His Leu Gln Thr Ile Ala Tyr Glu Lys Tyr Cys
            180                 185                 190

Val Ala Asn Gln Leu His Pro Asp Val Phe Pro Ala Val Arg Lys Met
        195                 200                 205
```

```
Glu Ser Glu Val Val Ser Met Val Leu Arg Met Phe Asn Ala Pro Ser
    210                 215                 220

Asp Thr Gly Cys Gly Thr Thr Thr Ser Gly Gly Thr Glu Ser Leu Leu
225                 230                 235                 240

Leu Ala Cys Leu Ser Ala Lys Met Tyr Ala Leu His His Arg Gly Ile
                245                 250                 255

Thr Glu Pro Glu Ile Ile Ala Pro Val Thr Ala His Ala Gly Phe Asp
            260                 265                 270

Lys Ala Ala Tyr Tyr Phe Gly Met Lys Leu Arg His Val Glu Leu Asp
        275                 280                 285

Pro Thr Thr Tyr Gln Val Asp Leu Gly Lys Val Lys Lys Phe Ile Asn
    290                 295                 300

Lys Asn Thr Ile Leu Leu Val Gly Ser Ala Pro Asn Phe Pro His Gly
305                 310                 315                 320

Ile Ala Asp Asp Ile Glu Gly Leu Gly Lys Ile Ala Gln Lys Tyr Lys
                325                 330                 335

Leu Pro Leu His Val Asp Ser Cys Leu Gly Ser Phe Ile Val Ser Phe
            340                 345                 350

Met Glu Lys Ala Gly Tyr Lys Asn Leu Pro Leu Leu Asp Phe Arg Val
        355                 360                 365

Pro Gly Val Thr Ser Ile Ser Cys Asp Thr His Lys Tyr Gly Phe Ala
    370                 375                 380

Pro Lys Gly Ser Ser Val Ile Met Tyr Arg Asn Ser Asp Leu Arg Met
385                 390                 395                 400

His Gln Tyr Tyr Val Asn Pro Ala Trp Thr Gly Gly Leu Tyr Gly Ser
                405                 410                 415

Pro Thr Leu Ala Gly Ser Arg Pro Gly Ala Ile Val Val Gly Cys Trp
            420                 425                 430

Ala Thr Met Val Asn Met Gly Glu Asn Gly Tyr Ile Glu Ser Cys Gln
        435                 440                 445

Glu Ile Val Gly Ala Ala Met Lys Phe Lys Lys Tyr Ile Gln Glu Asn
    450                 455                 460

Ile Pro Asp Leu Asn Ile Met Gly Asn Pro Arg Tyr Ser Val Ile Ser
465                 470                 475                 480

Phe Ser Ser Lys Thr Leu Asn Ile His Glu Leu Ser Asp Arg Leu Ser
                485                 490                 495

Lys Lys Gly Trp His Phe Asn Ala Leu Gln Lys Pro Val Ala Leu His
            500                 505                 510

Met Ala Phe Thr Arg Leu Ser Ala His Val Val Asp Glu Ile Cys Asp
        515                 520                 525

Ile Leu Arg Thr Thr Val Gln Glu Leu Lys Ser Glu Ser Asn Ser Lys
    530                 535                 540

Pro Ser Pro Asp Gly Thr Ser Ala Leu Tyr Gly Val Ala Gly Ser Val
545                 550                 555                 560

Lys Thr Ala Gly Val Ala Asp Lys Leu Ile Val Gly Phe Leu Asp Ala
                565                 570                 575

Leu Tyr Lys Leu Gly Pro Gly Glu Asp Thr Ala Thr Lys
            580                 585

<210> SEQ ID NO 3
<211> LENGTH: 1629
<212> TYPE: DNA
<213> ORGANISM: C. elegans
```

-continued

```
<220> FEATURE:
<221> NAME/KEY: CDS
<222> LOCATION: (1)...(1629)

<400> SEQUENCE: 3 atg gat ttt gca ctg gag caa tat cat agt gca aag gat ttg tta ata        48
Met Asp Phe Ala Leu Glu Gln Tyr His Ser Ala Lys Asp Leu Leu Ile
 1               5                  10                  15 ttt gag ctt cga aag ttc aat cca att gtt ctg gtt tct agt act att        96
Phe Glu Leu Arg Lys Phe Asn Pro Ile Val Leu Val Ser Ser Thr Ile
             20                  25                  30 gtt gca aca tac gta ctc acc aat ctg aga cat atg cat tta gat gaa       144
Val Ala Thr Tyr Val Leu Thr Asn Leu Arg His Met His Leu Asp Glu
         35                  40                  45 atg ggc atc cgg aaa cgt ttg agc act tgg ttt ttc acc act gta aag       192
Met Gly Ile Arg Lys Arg Leu Ser Thr Trp Phe Phe Thr Thr Val Lys
     50                  55                  60 cgt gtg cct ttc atc agg aaa atg att gac aaa caa cta aac gaa gta       240
Arg Val Pro Phe Ile Arg Lys Met Ile Asp Lys Gln Leu Asn Glu Val
 65                  70                  75                  80 aag gac gag ctt gag aaa agt ctg aga att gtg gat cga agc acc gaa       288
Lys Asp Glu Leu Glu Lys Ser Leu Arg Ile Val Asp Arg Ser Thr Glu
                 85                  90                  95 tac ttc act aca atc cca agc cat tca gtt gga aga act gaa gta ctt       336
Tyr Phe Thr Thr Ile Pro Ser His Ser Val Gly Arg Thr Glu Val Leu
            100                 105                 110 cgc ctt gct gcc atc tat gat gat ttg gaa gga cca gct ttt ttg gaa       384
Arg Leu Ala Ala Ile Tyr Asp Asp Leu Glu Gly Pro Ala Phe Leu Glu
        115                 120                 125 gga aga gta tct gga gca gtc ttc aat aga gaa gac gac aag gac gaa       432
Gly Arg Val Ser Gly Ala Val Phe Asn Arg Glu Asp Asp Lys Asp Glu
    130                 135                 140 cgg gag atg tat gag gag gtg ttc gga aaa ttt gcc tgg acc aac cca       480
Arg Glu Met Tyr Glu Glu Val Phe Gly Lys Phe Ala Trp Thr Asn Pro
145                 150                 155                 160 ctt tgg cca aaa ttg ttc cct gga gtg aga atc atg gag gct gaa gtt       528
Leu Trp Pro Lys Leu Phe Pro Gly Val Arg Ile Met Glu Ala Glu Val
                165                 170                 175 gtt cgc atg tgt tgt aat atg atg aat gga gat tcg gag aca tgt gga       576
Val Arg Met Cys Cys Asn Met Met Asn Gly Asp Ser Glu Thr Cys Gly
            180                 185                 190 act atg tca act ggt gga tcc att tca att ctt ttg gcg tgc ctg gct       624
Thr Met Ser Thr Gly Gly Ser Ile Ser Ile Leu Leu Ala Cys Leu Ala
        195                 200                 205 cat cgt aat cgt ctt ttg aaa aga gga gaa aag tac aca gag atg att       672
His Arg Asn Arg Leu Leu Lys Arg Gly Glu Lys Tyr Thr Glu Met Ile
    210                 215                 220 gtc cca tca tcc gtc cat gca gcg ttc ttc aaa gct gcc gaa tgt ttc       720
Val Pro Ser Ser Val His Ala Ala Phe Phe Lys Ala Ala Glu Cys Phe
225                 230                 235                 240 cgt atc aaa gtt cgc aag att cca gtt gat cct gtt act ttc aaa gta       768
Arg Ile Lys Val Arg Lys Ile Pro Val Asp Pro Val Thr Phe Lys Val
                245                 250                 255 gac ctt gtc aaa atg aaa gcc gca att aac aag aga aca tgt atg tta       816
Asp Leu Val Lys Met Lys Ala Ala Ile Asn Lys Arg Thr Cys Met Leu
            260                 265                 270 gtt gga tct gct cca aac ttt cca ttt gga act gtt gat gac att gaa       864
Val Gly Ser Ala Pro Asn Phe Pro Phe Gly Thr Val Asp Asp Ile Glu
        275                 280                 285
```

```
gct att gga cag cta gga ctt gaa tat gac atc cca gtt cat gtt gat    912
Ala Ile Gly Gln Leu Gly Leu Glu Tyr Asp Ile Pro Val His Val Asp
    290                 295                 300 gct tgt ctt ggt ggt ttc ctt ctt cca ttc ctt gaa gaa gac gag att    960
Ala Cys Leu Gly Gly Phe Leu Leu Pro Phe Leu Glu Glu Asp Glu Ile
305                 310                 315                 320 cgc tat gac ttc cgt gtt cct ggt gta tct tcg att tct gca gat agt   1008
Arg Tyr Asp Phe Arg Val Pro Gly Val Ser Ser Ile Ser Ala Asp Ser
                325                 330                 335 cac aaa tac gga ctc gct cca aag ggg tca tca gtt gtt ctt tat cgc   1056
His Lys Tyr Gly Leu Ala Pro Lys Gly Ser Ser Val Val Leu Tyr Arg
            340                 345                 350 aat aag gaa ctt ctt cat aat cag tac ttc tgt gat gct gat tgg caa   1104
Asn Lys Glu Leu Leu His Asn Gln Tyr Phe Cys Asp Ala Asp Trp Gln
        355                 360                 365 gga ggt atc tat gca tcg gct act atg gaa gga tca cgc gct ggg cac   1152
Gly Gly Ile Tyr Ala Ser Ala Thr Met Glu Gly Ser Arg Ala Gly His
    370                 375                 380 aac att gca ctt tgc tgg gcc gca atg ctt tat cac gct cag gaa gga   1200
Asn Ile Ala Leu Cys Trp Ala Ala Met Leu Tyr His Ala Gln Glu Gly
385                 390                 395                 400 tac aag gcc aat gct aga aag att gtt gac act aca aga aag att aga   1248
Tyr Lys Ala Asn Ala Arg Lys Ile Val Asp Thr Thr Arg Lys Ile Arg
                405                 410                 415 aat gga ctt tca aac att aag gga atc aaa tta caa ggg cca agt gat   1296
Asn Gly Leu Ser Asn Ile Lys Gly Ile Lys Leu Gln Gly Pro Ser Asp
            420                 425                 430 gtt tgt att gtt agc tgg aca acc aat gat gga gtt gaa ctc tac aga   1344
Val Cys Ile Val Ser Trp Thr Thr Asn Asp Gly Val Glu Leu Tyr Arg
        435                 440                 445 ttc cat aac ttc atg aag gaa aaa cat tgg caa ctg aat gga ctt caa   1392
Phe His Asn Phe Met Lys Glu Lys His Trp Gln Leu Asn Gly Leu Gln
    450                 455                 460 ttc cca gct gga gtt cat atc atg gtc act atg aat cat act cat cct   1440
Phe Pro Ala Gly Val His Ile Met Val Thr Met Asn His Thr His Pro
465                 470                 475                 480 gga ctc gct gaa gct ttc gtc gcc gat tgc aga gct gca gtt gag ttt   1488
Gly Leu Ala Glu Ala Phe Val Ala Asp Cys Arg Ala Ala Val Glu Phe
                485                 490                 495 gtc aaa agc cac aaa cca tcg gaa tcc gac aag aca agt gaa gca gcc   1536
Val Lys Ser His Lys Pro Ser Glu Ser Asp Lys Thr Ser Glu Ala Ala
            500                 505                 510 atc tac gga ctt gct caa agt att cca gac cga tcg ctt gtt cac gag   1584
Ile Tyr Gly Leu Ala Gln Ser Ile Pro Asp Arg Ser Leu Val His Glu
        515                 520                 525 ttt gct cac agc tat atc gat gct gtt tat gct tta aca gag tga       1629
Phe Ala His Ser Tyr Ile Asp Ala Val Tyr Ala Leu Thr Glu *
    530                 535                 540

<210> SEQ ID NO 4
<211> LENGTH: 542
<212> TYPE: PRT
<213> ORGANISM: C. elegans

<400> SEQUENCE: 4

Met Asp Phe Ala Leu Glu Gln Tyr His Ser Ala Lys Asp Leu Leu Ile
1               5                   10                  15

Phe Glu Leu Arg Lys Phe Asn Pro Ile Val Leu Val Ser Ser Thr Ile
            20                  25                  30
```

-continued

```
Val Ala Thr Tyr Val Leu Thr Asn Leu Arg His Met His Leu Asp Glu
        35                  40                  45

Met Gly Ile Arg Lys Arg Leu Ser Thr Trp Phe Phe Thr Thr Val Lys
    50                  55                  60

Arg Val Pro Phe Ile Arg Lys Met Ile Asp Lys Gln Leu Asn Glu Val
65                  70                  75                  80

Lys Asp Glu Leu Glu Lys Ser Leu Arg Ile Val Asp Arg Ser Thr Glu
                85                  90                  95

Tyr Phe Thr Thr Ile Pro Ser His Ser Val Gly Arg Thr Glu Val Leu
            100                 105                 110

Arg Leu Ala Ala Ile Tyr Asp Asp Leu Glu Gly Pro Ala Phe Leu Glu
        115                 120                 125

Gly Arg Val Ser Gly Ala Val Phe Asn Arg Glu Asp Asp Lys Asp Glu
    130                 135                 140

Arg Glu Met Tyr Glu Glu Val Phe Gly Lys Phe Ala Trp Thr Asn Pro
145                 150                 155                 160

Leu Trp Pro Lys Leu Phe Pro Gly Val Arg Ile Met Glu Ala Glu Val
                165                 170                 175

Val Arg Met Cys Cys Asn Met Met Asn Gly Asp Ser Glu Thr Cys Gly
            180                 185                 190

Thr Met Ser Thr Gly Gly Ser Ile Ser Ile Leu Leu Ala Cys Leu Ala
        195                 200                 205

His Arg Asn Arg Leu Leu Lys Arg Gly Glu Lys Tyr Thr Glu Met Ile
    210                 215                 220

Val Pro Ser Ser Val His Ala Ala Phe Phe Lys Ala Ala Glu Cys Phe
225                 230                 235                 240

Arg Ile Lys Val Arg Lys Ile Pro Val Asp Pro Val Thr Phe Lys Val
                245                 250                 255

Asp Leu Val Lys Met Lys Ala Ala Ile Asn Lys Arg Thr Cys Met Leu
            260                 265                 270

Val Gly Ser Ala Pro Asn Phe Pro Phe Gly Thr Val Asp Asp Ile Glu
        275                 280                 285

Ala Ile Gly Gln Leu Gly Leu Glu Tyr Asp Ile Pro Val His Val Asp
    290                 295                 300

Ala Cys Leu Gly Gly Phe Leu Leu Pro Phe Leu Glu Glu Asp Glu Ile
305                 310                 315                 320

Arg Tyr Asp Phe Arg Val Pro Gly Val Ser Ile Ser Ala Asp Ser
                325                 330                 335

His Lys Tyr Gly Leu Ala Pro Lys Gly Ser Ser Val Val Leu Tyr Arg
            340                 345                 350

Asn Lys Glu Leu Leu His Asn Gln Tyr Phe Cys Asp Ala Asp Trp Gln
        355                 360                 365

Gly Gly Ile Tyr Ala Ser Ala Thr Met Glu Gly Ser Arg Ala Gly His
    370                 375                 380

Asn Ile Ala Leu Cys Trp Ala Ala Met Leu Tyr His Ala Gln Glu Gly
385                 390                 395                 400

Tyr Lys Ala Asn Ala Arg Lys Ile Val Asp Thr Thr Arg Lys Ile Arg
                405                 410                 415

Asn Gly Leu Ser Asn Ile Lys Gly Ile Lys Leu Gln Gly Pro Ser Asp
            420                 425                 430

Val Cys Ile Val Ser Trp Thr Thr Asn Asp Gly Val Glu Leu Tyr Arg
        435                 440                 445
```

```
Phe His Asn Phe Met Lys Glu Lys His Trp Gln Leu Asn Gly Leu Gln
    450                 455                 460

Phe Pro Ala Gly Val His Ile Met Val Thr Met Asn His Thr His Pro
465                 470                 475                 480

Gly Leu Ala Glu Ala Phe Val Ala Asp Cys Arg Ala Ala Val Glu Phe
                485                 490                 495

Val Lys Ser His Lys Pro Ser Glu Ser Asp Lys Thr Ser Glu Ala Ala
                500                 505                 510

Ile Tyr Gly Leu Ala Gln Ser Ile Pro Asp Arg Ser Leu Val His Glu
            515                 520                 525

Phe Ala His Ser Tyr Ile Asp Ala Val Tyr Ala Leu Thr Glu
            530                 535                 540

<210> SEQ ID NO 5
<211> LENGTH: 1707
<212> TYPE: DNA
<213> ORGANISM: Mus musculus
<220> FEATURE:
<221> NAME/KEY: CDS
<222> LOCATION: (1)...(1707)

<400> SEQUENCE: 5
```

| | | | | | | | | | | | | | | | | |
|---|---|---|---|---|---|---|---|---|---|---|---|---|---|---|---|---|
| atg | ccc | gga | acc | gac | ctc | ctc | aag | ctg | aag | gac | ttc | gag | cct | tat | ttg | 48 |
| Met | Pro | Gly | Thr | Asp | Leu | Leu | Lys | Leu | Lys | Asp | Phe | Glu | Pro | Tyr | Leu | |
| 1 | | | | 5 | | | | | 10 | | | | | 15 | | |

```
gag att ttg gaa tct tat tcc aca aaa gcc aag aat tat gtg aat gga    96
Glu Ile Leu Glu Ser Tyr Ser Thr Lys Ala Lys Asn Tyr Val Asn Gly
             20                  25                  30 tat tgc acc aaa tat gag ccc tgg cag ctc att gcg tgg agt gtc ctg   144
Tyr Cys Thr Lys Tyr Glu Pro Trp Gln Leu Ile Ala Trp Ser Val Leu
         35                  40                  45 tgt act ctg ctg ata gtc tgg gtg tat gag ctt atc ttc cag cca gag   192
Cys Thr Leu Leu Ile Val Trp Val Tyr Glu Leu Ile Phe Gln Pro Glu
     50                  55                  60 agt tta tgg tct cgg ttt aaa aaa aaa tta ttt aag ctt atc agg aag   240
Ser Leu Trp Ser Arg Phe Lys Lys Lys Leu Phe Lys Leu Ile Arg Lys
 65                  70                  75                  80 atg cca ttt att gga cgt aag atc gaa caa cag gtg agc aaa gcc aag   288
Met Pro Phe Ile Gly Arg Lys Ile Glu Gln Gln Val Ser Lys Ala Lys
                 85                  90                  95 aag gat ctt gtc aag aac atg cca ttc cta aag gtg gac aag gat tat   336
Lys Asp Leu Val Lys Asn Met Pro Phe Leu Lys Val Asp Lys Asp Tyr
            100                 105                 110 gtg aaa act ctg cct gct cag ggt atg ggc aca gct gag gtt ctg gag   384
Val Lys Thr Leu Pro Ala Gln Gly Met Gly Thr Ala Glu Val Leu Glu
        115                 120                 125 aga ctc aag gag tac agc tcc atg gat ggt tcc tgg caa gaa ggg aaa   432
Arg Leu Lys Glu Tyr Ser Ser Met Asp Gly Ser Trp Gln Glu Gly Lys
    130                 135                 140 gcc tca gga gct gtg tac aat ggg gaa ccg aag ctc acg gag ctg ctg   480
Ala Ser Gly Ala Val Tyr Asn Gly Glu Pro Lys Leu Thr Glu Leu Leu
145                 150                 155                 160 gtg cag gct tat gga gaa ttc acg tgg agc aat cca ctg cat cca gat   528
Val Gln Ala Tyr Gly Glu Phe Thr Trp Ser Asn Pro Leu His Pro Asp
                165                 170                 175 atc ttc cct gga ttg cgg aag tta gag gca gaa atc gtt agg atg act   576
Ile Phe Pro Gly Leu Arg Lys Leu Glu Ala Glu Ile Val Arg Met Thr
            180                 185                 190
```

-continued

| | | |
|---|---|---|
| tgt tcc ctc ttc aat ggg gga cca gat tcc tgt gga tgt gtg act tct<br>Cys Ser Leu Phe Asn Gly Gly Pro Asp Ser Cys Gly Cys Val Thr Ser<br>195                         200                       205 | 624 |

```
tgt tcc ctc ttc aat ggg gga cca gat tcc tgt gga tgt gtg act tct    624
Cys Ser Leu Phe Asn Gly Gly Pro Asp Ser Cys Gly Cys Val Thr Ser
    195                 200                 205 ggg gga acg gaa agc atc ctg atg gcc tgc aaa gct tac cgg gac ttg    672
Gly Gly Thr Glu Ser Ile Leu Met Ala Cys Lys Ala Tyr Arg Asp Leu
210                 215                 220 gcg tta gag aag ggg atc aaa act cca gaa att gtg gct ccc gag agt    720
Ala Leu Glu Lys Gly Ile Lys Thr Pro Glu Ile Val Ala Pro Glu Ser
225                 230                 235                 240 gcc cat gct gca ttc gac aaa gca gct cat tat ttt ggg atg aag att    768
Ala His Ala Ala Phe Asp Lys Ala Ala His Tyr Phe Gly Met Lys Ile
            245                 250                 255 gtc cga gtt gca ctg aaa aag aac atg gag gtg gat gtg cag gca atg    816
Val Arg Val Ala Leu Lys Lys Asn Met Glu Val Asp Val Gln Ala Met
        260                 265                 270 aag aga gcc atc tcc agg aac aca gct atg ctg gtc tgt tct acc cca    864
Lys Arg Ala Ile Ser Arg Asn Thr Ala Met Leu Val Cys Ser Thr Pro
    275                 280                 285 cag ttt cct cat ggt gtg atg gat cct gtc ccc gaa gtg gcc aag tta    912
Gln Phe Pro His Gly Val Met Asp Pro Val Pro Glu Val Ala Lys Leu
290                 295                 300 act gtc aga tat aaa atc cca ctc cat gtg gat gct tgt ctg ggg ggc    960
Thr Val Arg Tyr Lys Ile Pro Leu His Val Asp Ala Cys Leu Gly Gly
305                 310                 315                 320 ttc ctc att gtc ttc atg gag aaa gca ggg tac cca ctg gag aaa cca   1008
Phe Leu Ile Val Phe Met Glu Lys Ala Gly Tyr Pro Leu Glu Lys Pro
            325                 330                 335 ttt gat ttc cgg gtg aaa ggt gtg acc agc att tca gca gat act cat   1056
Phe Asp Phe Arg Val Lys Gly Val Thr Ser Ile Ser Ala Asp Thr His
        340                 345                 350 aag tat ggc tat gct cct aaa ggt tca tca gtg gtg atg tac tct aac   1104
Lys Tyr Gly Tyr Ala Pro Lys Gly Ser Ser Val Val Met Tyr Ser Asn
    355                 360                 365 gag aag tac agg acg tac cag ttc ttt gtt ggt gca gac tgg caa ggt   1152
Glu Lys Tyr Arg Thr Tyr Gln Phe Phe Val Gly Ala Asp Trp Gln Gly
370                 375                 380 ggt gtc tac gca tct cca agc ata gct ggc tca cgg cct ggt ggc atc   1200
Gly Val Tyr Ala Ser Pro Ser Ile Ala Gly Ser Arg Pro Gly Gly Ile
385                 390                 395                 400 att gca gcc tgt tgg gcg gcc ttg atg cac ttc ggt gag aac ggc tat   1248
Ile Ala Ala Cys Trp Ala Ala Leu Met His Phe Gly Glu Asn Gly Tyr
            405                 410                 415 gtt gaa gct acc aaa cag atc atc aaa act gct cgc ttc ctg aag tca   1296
Val Glu Ala Thr Lys Gln Ile Ile Lys Thr Ala Arg Phe Leu Lys Ser
        420                 425                 430 gaa ctg gaa aac atc aaa aac atc ttc att ttc ggt gat cct caa ttg   1344
Glu Leu Glu Asn Ile Lys Asn Ile Phe Ile Phe Gly Asp Pro Gln Leu
    435                 440                 445 tca gtt att gct ctg gga tcc aac gat ttt gac att tac cga cta tct   1392
Ser Val Ile Ala Leu Gly Ser Asn Asp Phe Asp Ile Tyr Arg Leu Ser
450                 455                 460 aat atg atg tct gct aag ggg tgg aat ttt aac tac ctg cag ttc cca   1440
Asn Met Met Ser Ala Lys Gly Trp Asn Phe Asn Tyr Leu Gln Phe Pro
465                 470                 475                 480 aga agc att cat ttc tgc att acg tta gta cat act cgg aag cga gtg   1488
Arg Ser Ile His Phe Cys Ile Thr Leu Val His Thr Arg Lys Arg Val
            485                 490                 495 gcg atc cag ttc cta aag gat atc cgg gaa tca gtc aca caa atc atg   1536
Ala Ile Gln Phe Leu Lys Asp Ile Arg Glu Ser Val Thr Gln Ile Met
        500                 505                 510
```

```
aag aat cct aaa gct aag acc aca gga atg ggt gcc atc tat ggc atg    1584
Lys Asn Pro Lys Ala Lys Thr Thr Gly Met Gly Ala Ile Tyr Gly Met
            515                 520                 525 gcc cag gca acc att gac agg aag ctg gtt gca gaa ata tcc tcc gtc    1632
Ala Gln Ala Thr Ile Asp Arg Lys Leu Val Ala Glu Ile Ser Ser Val
        530                 535                 540 ttc ttg gac tgc ctt tat act acg gac ccc gtg act cag ggc aac cag    1680
Phe Leu Asp Cys Leu Tyr Thr Thr Asp Pro Val Thr Gln Gly Asn Gln
545                 550                 555                 560 atg aac ggt tct cca aag ccc cgc tga                                1707
Met Asn Gly Ser Pro Lys Pro Arg *
                565

<210> SEQ ID NO 6
<211> LENGTH: 568
<212> TYPE: PRT
<213> ORGANISM: Mus musculus

<400> SEQUENCE: 6

Met Pro Gly Thr Asp Leu Leu Lys Leu Lys Asp Phe Glu Pro Tyr Leu
 1               5                  10                  15

Glu Ile Leu Glu Ser Tyr Ser Thr Lys Ala Lys Asn Tyr Val Asn Gly
             20                  25                  30

Tyr Cys Thr Lys Tyr Glu Pro Trp Gln Leu Ile Ala Trp Ser Val Leu
         35                  40                  45

Cys Thr Leu Leu Ile Val Trp Val Tyr Glu Leu Ile Phe Gln Pro Glu
     50                  55                  60

Ser Leu Trp Ser Arg Phe Lys Lys Leu Phe Lys Leu Ile Arg Lys
 65                  70                  75                  80

Met Pro Phe Ile Gly Arg Lys Ile Glu Gln Gln Val Ser Lys Ala Lys
                 85                  90                  95

Lys Asp Leu Val Lys Asn Met Pro Phe Leu Lys Val Asp Lys Asp Tyr
            100                 105                 110

Val Lys Thr Leu Pro Ala Gln Gly Met Gly Thr Ala Glu Val Leu Glu
        115                 120                 125

Arg Leu Lys Glu Tyr Ser Ser Met Asp Gly Ser Trp Gln Gly Lys
    130                 135                 140

Ala Ser Gly Ala Val Tyr Asn Gly Glu Pro Lys Leu Thr Glu Leu Leu
145                 150                 155                 160

Val Gln Ala Tyr Gly Glu Phe Thr Trp Ser Asn Pro Leu His Pro Asp
                165                 170                 175

Ile Phe Pro Gly Leu Arg Lys Leu Glu Ala Glu Ile Val Arg Met Thr
            180                 185                 190

Cys Ser Leu Phe Asn Gly Gly Pro Asp Ser Gly Cys Val Thr Ser
        195                 200                 205

Gly Gly Thr Glu Ser Ile Leu Met Ala Cys Lys Ala Tyr Arg Asp Leu
    210                 215                 220

Ala Leu Glu Lys Gly Ile Lys Thr Pro Glu Ile Val Ala Pro Glu Ser
225                 230                 235                 240

Ala His Ala Ala Phe Asp Lys Ala His Tyr Phe Gly Met Lys Ile
                245                 250                 255

Val Arg Val Ala Leu Lys Lys Asn Met Glu Val Asp Val Gln Ala Met
            260                 265                 270

Lys Arg Ala Ile Ser Arg Asn Thr Ala Met Leu Val Cys Ser Thr Pro
        275                 280                 285
```

```
Gln Phe Pro His Gly Val Met Asp Pro Val Pro Glu Val Ala Lys Leu
    290                 295                 300

Thr Val Arg Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu Lys Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Val Val Met Tyr Ser Asn
        355                 360                 365

Glu Lys Tyr Arg Thr Tyr Gln Phe Val Gly Ala Asp Trp Gln Gly
    370                 375                 380

Gly Val Tyr Ala Ser Pro Ser Ile Ala Gly Ser Arg Pro Gly Gly Ile
385                 390                 395                 400

Ile Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Asn Ile Phe Ile Phe Gly Asp Pro Gln Leu
        435                 440                 445

Ser Val Ile Ala Leu Gly Ser Asn Asp Phe Asp Ile Tyr Arg Leu Ser
    450                 455                 460

Asn Met Met Ser Ala Lys Gly Trp Asn Phe Asn Tyr Leu Gln Phe Pro
465                 470                 475                 480

Arg Ser Ile His Phe Cys Ile Thr Leu Val His Thr Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Gly Met
        515                 520                 525

Ala Gln Ala Thr Ile Asp Arg Lys Leu Val Ala Glu Ile Ser Ser Val
    530                 535                 540

Phe Leu Asp Cys Leu Tyr Thr Thr Asp Pro Val Thr Gln Gly Asn Gln
545                 550                 555                 560

Met Asn Gly Ser Pro Lys Pro Arg
                565

<210> SEQ ID NO 7
<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 7 atg cct agc aca gac ctt ctg atg ttg aag gcc ttt gag ccc tac tta    48
Met Pro Ser Thr Asp Leu Leu Met Leu Lys Ala Phe Glu Pro Tyr Leu
 1               5                  10                  15 gag att ttg gaa gta tac tcc aca aaa gcc aag aat tat gta aat gga    96
Glu Ile Leu Glu Val Tyr Ser Thr Lys Ala Lys Asn Tyr Val Asn Gly
                20                  25                  30 cat tgc acc aag tat gag ccc tgg cag cta att gca tgg agt gtc gtg   144
His Cys Thr Lys Tyr Glu Pro Trp Gln Leu Ile Ala Trp Ser Val Val
            35                  40                  45
```

```
tgg acc ctg ctg ata gtc tgg gga tat gag ttt gtc ttc cag cca gag      192
Trp Thr Leu Leu Ile Val Trp Gly Tyr Glu Phe Val Phe Gln Pro Glu
     50              55                  60 agt tta tgg tca agg ttt aaa aag aaa tgt ttt aag ctc acc agg aag      240
Ser Leu Trp Ser Arg Phe Lys Lys Lys Cys Phe Lys Leu Thr Arg Lys
 65              70                  75                  80 atg ccc att att ggt cgt aag att caa gac aag ttg aac aag acc aag      288
Met Pro Ile Ile Gly Arg Lys Ile Gln Asp Lys Leu Asn Lys Thr Lys
                 85                  90                  95 gat gat att agc aag aac atg tca ttc ctg aaa gtg gac aaa gag tat      336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag      384
Val Lys Ala Leu Pro Ser Gln Gly Leu Ser Ser Ser Ala Val Leu Glu
        115                 120                 125 aaa ctt aag gag tac agc tct atg gac gcc ttc tgg caa gag ggg aga      432
Lys Leu Lys Glu Tyr Ser Ser Met Asp Ala Phe Trp Gln Glu Gly Arg
130                 135                 140 gcc tct gga aca gtg tac agt ggg gag gag aag ctc act gag ctc ctt      480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat      528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct      576
Ile Phe Pro Gly Leu Arg Lys Ile Glu Ala Glu Ile Val Arg Ile Ala
            180                 185                 190 tgt tcc ctg ttc aat ggg gga cca gat tcg tgt gga tgt gtg act tct      624
Cys Ser Leu Phe Asn Gly Gly Pro Asp Ser Cys Gly Cys Val Thr Ser
        195                 200                 205 ggg gga aca gaa agc ata ctc atg gcc tgc aaa gca tgt cgg gat ctg      672
Gly Gly Thr Glu Ser Ile Leu Met Ala Cys Lys Ala Cys Arg Asp Leu
210                 215                 220 gcc ttt gag aag ggg atc aaa act cca gaa att gtg gct ccc caa agt      720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att      768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg      816
Val Arg Val Pro Leu Thr Lys Met Met Glu Val Asp Val Arg Ala Met
            260                 265                 270 aga aga gct atc tcc agg aac act gcc atg ctc gtc tgt tct acc cca      864
Arg Arg Ala Ile Ser Arg Asn Thr Ala Met Leu Val Cys Ser Thr Pro
        275                 280                 285 cag ttt cct cat ggt gta ata gat cct gtc cct gaa gtg gcc aag ctg      912
Gln Phe Pro His Gly Val Ile Asp Pro Val Pro Glu Val Ala Lys Leu
290                 295                 300 gct gtc aaa tac aaa ata ccc ctt cat gtc gac gct tgt ctg gga ggc      960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca     1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat     1056
Phe Asp Phe Arg Val Lys Gly Val Thr Ser Ile Ser Ala Asp Thr His
            340                 345                 350 aag tat ggc tat gcc cca aaa ggc tca tca ttg gtg ttg tat agt gac     1104
Lys Tyr Gly Tyr Ala Pro Lys Gly Ser Ser Leu Val Leu Tyr Ser Asp
        355                 360                 365
```

```
aag aag tac agg aac tat cag ttc ttc gtc gat aca gat tgg cag ggt    1152
Lys Lys Tyr Arg Asn Tyr Gln Phe Phe Val Asp Thr Asp Trp Gln Gly
    370                 375                 380 ggc atc tat gct tcc cca acc atc gca ggc tca cgg cct ggt ggc att    1200
Gly Ile Tyr Ala Ser Pro Thr Ile Ala Gly Ser Arg Pro Gly Gly Ile
385                 390                 395                 400 agc gca gcc tgt tgg gct gcc ttg atg cac ttc ggt gag aac ggc tat    1248
Ser Ala Ala Cys Trp Ala Ala Leu Met His Phe Gly Glu Asn Gly Tyr
                405                 410                 415 gtt gaa gct acc aaa cag atc atc aaa act gct cgc ttc ctc aag tca    1296
Val Glu Ala Thr Lys Gln Ile Ile Lys Thr Ala Arg Phe Leu Lys Ser
            420                 425                 430 gaa ctg gaa aat atc aaa ggc atc ttt gtt ttt ggg aat ccc caa ttg    1344
Glu Leu Glu Asn Ile Lys Gly Ile Phe Val Phe Gly Asn Pro Gln Leu
        435                 440                 445 tca ctc att gct ctg gga tcc cgt gat ttt gac atc tac cga cta tca    1392
Ser Leu Ile Ala Leu Gly Ser Arg Asp Phe Asp Ile Tyr Arg Leu Ser
450                 455                 460 aac ctg atg act gct aag ggg tgg aac ttg aac cag ttg cag ttc cca    1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta    1488
Pro Ser Ile His Phe Cys Ile Thr Leu Leu His Ala Arg Lys Arg Val
                485                 490                 495 gct ata caa ttc cta aag gac att cga gaa tct gtc act caa atc atg    1536
Ala Ile Gln Phe Leu Lys Asp Ile Arg Glu Ser Val Thr Gln Ile Met
            500                 505                 510 aag aat cct aaa gcg aag acc aca gga atg ggt gcc atc tat gcc atg    1584
Lys Asn Pro Lys Ala Lys Thr Thr Gly Met Gly Ala Ile Tyr Ala Met
        515                 520                 525 gcc cag aca act gtt gac agg aat atg gtt gca gaa ttg tcc tca gtc    1632
Ala Gln Thr Thr Val Asp Arg Asn Met Val Ala Glu Leu Ser Ser Val
530                 535                 540 ttc ttg gac agc ttg tac agc acc gac act gtc acc cag ggc agc cag    1680
Phe Leu Asp Ser Leu Tyr Ser Thr Asp Thr Val Thr Gln Gly Ser Gln
545                 550                 555                 560 atg aat ggt tct cca aaa ccc cac tga                                1707
Met Asn Gly Ser Pro Lys Pro His  *
                565

<210> SEQ ID NO 8
<211> LENGTH: 568
<212> TYPE: PRT
<213> ORGANISM: Homo sapiens

<400> SEQUENCE: 8

Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95
```

-continued

```
Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ala Val Leu Glu
        115                 120                 125

Lys Leu Lys Glu Tyr Ser Met Asp Ala Phe Trp Gln Glu Gly Arg
    130                 135                 140

Ala Ser Gly Thr Val Tyr Ser Gly Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Cys Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
        275                 280                 285

Gln Phe Pro His Gly Val Ile Asp Pro Val Pro Glu Val Ala Lys Leu
    290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Leu Val Leu Tyr Ser Asp
        355                 360                 365

Lys Lys Tyr Arg Asn Tyr Gln Phe Phe Val Asp Thr Asp Trp Gln Gly
    370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Gly Ile Phe Val Phe Gly Asn Pro Gln Leu
        435                 440                 445

Ser Leu Ile Ala Leu Gly Ser Arg Asp Phe Asp Ile Tyr Arg Leu Ser
    450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
            500                 505                 510
```

```
Lys Asn Pro Lys Ala Lys Thr Thr Gly Met Gly Ala Ile Tyr Ala Met
            515                 520                 525

Ala Gln Thr Thr Val Asp Arg Asn Met Val Ala Glu Leu Ser Ser Val
    530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
                565

<210> SEQ ID NO 9
<211> LENGTH: 1467
<212> TYPE: DNA
<213> ORGANISM: Homo sapiens
<220> FEATURE:
<221> NAME/KEY: CDS
<222> LOCATION: (1)...(1467)

<400> SEQUENCE: 9 atg cct agc aca gac ctt ctg atg ttg aag gcc ttt gag ccc tac tta    48
Met Pro Ser Thr Asp Leu Leu Met Leu Lys Ala Phe Glu Pro Tyr Leu
1               5                  10                  15 gag att ttg gaa gta tac tcc aca aaa gcc aag aat tat gta aat gga    96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg   144
His Cys Thr Lys Tyr Glu Pro Trp Gln Leu Ile Ala Trp Ser Val Val
        35                  40                  45 tgg acc ctg ctg ata gtc tgg gga tat gag ttt gtc ttc cag cca gag   192
Trp Thr Leu Leu Ile Val Trp Gly Tyr Glu Phe Val Phe Gln Pro Glu
    50                  55                  60 agt tta tgg tca agg ttt aaa aag aaa tgt ttt aag ctc acc agg aag   240
Ser Leu Trp Ser Arg Phe Lys Lys Lys Cys Phe Lys Leu Thr Arg Lys
65                  70                  75                  80 atg ccc att att ggt cgt aag att caa gac aag ttg aac aag acc aag   288
Met Pro Ile Ile Gly Arg Lys Ile Gln Asp Lys Leu Asn Lys Thr Lys
                85                  90                  95 gat gat att agc aag aac atg tca ttc ctg aaa gtg gac aaa gag tat   336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag   384
Val Lys Ala Leu Pro Ser Gln Gly Leu Ser Ser Ser Ala Val Leu Glu
        115                 120                 125 aaa ctt aag gag tac agc tct atg gac gcc ttc tgg caa gag ggg aga   432
Lys Leu Lys Glu Tyr Ser Ser Met Asp Ala Phe Trp Gln Glu Gly Arg
    130                 135                 140 gcc tct gga aca gtg tac agt ggg gag gag aag ctc act gag ctc ctt   480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat   528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct   576
Ile Phe Pro Gly Leu Arg Lys Ile Glu Ala Glu Ile Val Arg Ile Ala
            180                 185                 190 tgt tcc ctg ttc aat ggg gga cca gat tcg tgt gga tgt gtg act tct   624
Cys Ser Leu Phe Asn Gly Gly Pro Asp Ser Cys Gly Cys Val Thr Ser
        195                 200                 205 ggg gga aca gaa agc ata ctc atg gcc tgc aaa gca tgt cgg gat ctg   672
Gly Gly Thr Glu Ser Ile Leu Met Ala Cys Lys Ala Cys Arg Asp Leu
    210                 215                 220
```

```
gcc ttt gag aag ggg atc aaa act cca gaa att gtg gct ccc caa agt    720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att    768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg    816
Val Arg Val Pro Leu Thr Lys Met Met Glu Val Asp Val Arg Ala Met
            260                 265                 270 aga aga gct atc tcc agg aac act gcc atg ctc gtc tgt tct acc cca    864
Arg Arg Ala Ile Ser Arg Asn Thr Ala Met Leu Val Cys Ser Thr Pro
        275                 280                 285 cag ttt cct cat ggt gta ata gat cct gtc cct gaa gtg gcc aag ctg    912
Gln Phe Pro His Gly Val Ile Asp Pro Val Pro Glu Val Ala Lys Leu
    290                 295                 300 gct gtc aaa tac aaa ata ccc ctt cat gtc gac gct tgt ctg gga ggc    960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca   1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat   1056
Phe Asp Phe Arg Val Lys Gly Val Thr Ser Ile Ser Ala Asp Thr His
            340                 345                 350 aag ctg gaa aat atc aaa ggc atc ttt gtt ttt ggg aat ccc caa ttg   1104
Lys Leu Glu Asn Ile Lys Gly Ile Phe Val Phe Gly Asn Pro Gln Leu
        355                 360                 365 tca ctc att gct ctg gga tcc cgt gat ttt gac atc tac cga cta tca   1152
Ser Leu Ile Ala Leu Gly Ser Arg Asp Phe Asp Ile Tyr Arg Leu Ser
    370                 375                 380 aac ctg atg act gct aag ggg tgg aac ttg aac cag ttg cag ttc cca   1200
Asn Leu Met Thr Ala Lys Gly Trp Asn Leu Asn Gln Leu Gln Phe Pro
385                 390                 395                 400 ccc agt att cat ttc tgc atc aca tta cta cac gcc cgg aaa cga gta   1248
Pro Ser Ile His Phe Cys Ile Thr Leu Leu His Ala Arg Lys Arg Val
                405                 410                 415 gct ata caa ttc cta aag gac att cga gaa tct gtc act caa atc atg   1296
Ala Ile Gln Phe Leu Lys Asp Ile Arg Glu Ser Val Thr Gln Ile Met
            420                 425                 430 aag aat cct aaa gcg aag acc aca gga atg ggt gcc atc tat gcc atg   1344
Lys Asn Pro Lys Ala Lys Thr Thr Gly Met Gly Ala Ile Tyr Ala Met
        435                 440                 445 gcc cag aca act gtt gac agg aat atg gtt gca gaa ttg tcc tca gtc   1392
Ala Gln Thr Thr Val Asp Arg Asn Met Val Ala Glu Leu Ser Ser Val
    450                 455                 460 ttc ttg gac agc ttg tac agc acc gac act gtc acc cag ggc agc cag   1440
Phe Leu Asp Ser Leu Tyr Ser Thr Asp Thr Val Thr Gln Gly Ser Gln
465                 470                 475                 480 atg aat ggt tct cca aaa ccc cac tga                               1467
Met Asn Gly Ser Pro Lys Pro His  *
                485

<210> SEQ ID NO 10
<211> LENGTH: 488
<212> TYPE: PRT
<213> ORGANISM: Homo sapiens
```

```
<400> SEQUENCE: 10

Met Pro Ser Thr Asp Leu Leu Met Leu Lys Ala Phe Glu Pro Tyr Leu
 1               5                  10                  15

Glu Ile Leu Glu Val Tyr Ser Thr Lys Ala Lys Asn Tyr Val Asn Gly
             20                  25                  30

His Cys Thr Lys Tyr Glu Pro Trp Gln Leu Ile Ala Trp Ser Val Val
         35                  40                  45

Trp Thr Leu Leu Ile Val Trp Gly Tyr Glu Phe Val Phe Gln Pro Glu
     50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                 85                  90                  95

Asp Asp Ile Ser Lys Asn Met Ser Phe Leu Lys Val Asp Lys Glu Tyr
                100                 105                 110

Val Lys Ala Leu Pro Ser Gln Gly Leu Ser Ser Ala Val Leu Glu
            115                 120                 125

Lys Leu Lys Glu Tyr Ser Ser Met Asp Ala Phe Trp Gln Glu Gly Arg
130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
                180                 185                 190

Cys Ser Leu Phe Asn Gly Gly Pro Asp Ser Cys Gly Cys Val Thr Ser
            195                 200                 205

Gly Gly Thr Glu Ser Ile Leu Met Ala Cys Lys Ala Cys Arg Asp Leu
            210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
275                 280                 285

Gln Phe Pro His Gly Val Ile Asp Pro Val Pro Glu Val Ala Lys Leu
            290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Leu Glu Asn Ile Lys Gly Ile Phe Val Phe Gly Asn Pro Gln Leu
            355                 360                 365

Ser Leu Ile Ala Leu Gly Ser Arg Asp Phe Asp Ile Tyr Arg Leu Ser
            370                 375                 380

Asn Leu Met Thr Ala Lys Gly Trp Asn Leu Asn Gln Leu Gln Phe Pro
385                 390                 395                 400

Pro Ser Ile His Phe Cys Ile Thr Leu Leu His Ala Arg Lys Arg Val
                405                 410                 415
```

```
Ala Ile Gln Phe Leu Lys Asp Ile Arg Glu Ser Val Thr Gln Ile Met
            420                 425                 430

Lys Asn Pro Lys Ala Lys Thr Thr Gly Met Gly Ala Ile Tyr Ala Met
        435                 440                 445

Ala Gln Thr Thr Val Asp Arg Asn Met Val Ala Glu Leu Ser Ser Val
    450                 455                 460

Phe Leu Asp Ser Leu Tyr Ser Thr Asp Thr Val Thr Gln Gly Ser Gln
465                 470                 475                 480

Met Asn Gly Ser Pro Lys Pro His
                485

<210> SEQ ID NO 11
<211> LENGTH: 552
<212> TYPE: PRT
<213> ORGANISM: C. elegans

<400> SEQUENCE: 11

Met Asp Ser Val Lys His Thr Thr Glu Ile Ile Val Asp Leu Thr Lys
 1               5                  10                  15

Met His Tyr His Met Ile Asn Asp Arg Leu Ser Arg Tyr Asp Pro Val
            20                  25                  30

Val Leu Val Leu Ala Ala Phe Gly Gly Thr Leu Val Tyr Thr Lys Val
        35                  40                  45

Val His Leu Tyr Arg Lys Ser Glu Asp Pro Ile Leu Lys Arg Met Gly
    50                  55                  60

Ala Tyr Val Phe Ser Leu Leu Arg Lys Leu Pro Ala Val Arg Asp Lys
65                  70                  75                  80

Ile Glu Lys Glu Leu Ala Ala Glu Lys Pro Lys Leu Ile Glu Ser Ile
                85                  90                  95

His Lys Asp Asp Lys Asp Lys Gln Phe Ile Ser Thr Leu Pro Ile Ala
            100                 105                 110

Pro Leu Ser Gln Asp Ser Ile Met Glu Leu Ala Lys Lys Tyr Glu Asp
        115                 120                 125

Tyr Asn Thr Phe Asn Ile Asp Gly Gly Arg Val Ser Gly Ala Val Tyr
    130                 135                 140

Thr Asp Arg His Ala Glu His Ile Asn Leu Leu Gly Lys Ile Tyr Glu
145                 150                 155                 160

Lys Tyr Ala Phe Ser Asn Pro Leu His Pro Asp Val Phe Pro Gly Ala
                165                 170                 175

Arg Lys Met Glu Ala Glu Leu Ile Arg Met Val Leu Asn Leu Tyr Asn
            180                 185                 190

Gly Pro Glu Asp Ser Ser Gly Ser Val Thr Ser Gly Gly Thr Glu Ser
        195                 200                 205

Ile Ile Met Ala Cys Phe Ser Tyr Arg Asn Arg Ala His Ser Leu Gly
    210                 215                 220

Ile Glu His Pro Val Ile Leu Ala Cys Lys Thr Ala His Ala Ala Phe
225                 230                 235                 240

Asp Lys Ala Ala His Leu Cys Gly Met Arg Leu Arg His Val Pro Val
                245                 250                 255

Asp Ser Asp Asn Arg Val Asp Leu Lys Glu Met Glu Arg Leu Ile Asp
            260                 265                 270

Ser Asn Val Cys Met Leu Val Gly Ser Ala Pro Asn Phe Pro Ser Gly
        275                 280                 285

Thr Ile Asp Pro Ile Pro Glu Ile Ala Lys Leu Gly Lys Lys Tyr Gly
    290                 295                 300
```

```
Ile Pro Val His Val Asp Ala Cys Leu Gly Gly Phe Met Ile Pro Phe
305                 310                 315                 320

Met Asn Asp Ala Gly Tyr Leu Ile Pro Val Phe Asp Phe Arg Asn Pro
            325                 330                 335

Gly Val Thr Ser Ile Ser Cys Asp Thr His Lys Tyr Gly Cys Thr Pro
        340                 345                 350

Lys Gly Ser Ser Ile Val Met Tyr Arg Ser Lys Glu Leu His His Phe
    355                 360                 365

Gln Tyr Phe Ser Val Ala Asp Trp Cys Gly Gly Ile Tyr Ala Thr Pro
370                 375                 380

Thr Ile Ala Gly Ser Arg Ala Gly Ala Asn Thr Ala Val Ala Trp Ala
385                 390                 395                 400

Thr Leu Leu Ser Phe Gly Arg Asp Glu Tyr Val Arg Arg Cys Ala Gln
                405                 410                 415

Ile Val Lys His Thr Arg Met Leu Ala Glu Lys Ile Glu Lys Ile Lys
            420                 425                 430

Trp Ile Lys Pro Tyr Gly Lys Ser Asp Val Ser Leu Val Ala Phe Ser
        435                 440                 445

Gly Asn Gly Val Asn Ile Tyr Glu Val Ser Asp Lys Met Met Lys Leu
    450                 455                 460

Gly Trp Asn Leu Asn Thr Leu Gln Asn Pro Ala Ala Ile His Ile Cys
465                 470                 475                 480

Leu Thr Ile Asn Gln Ala Asn Glu Glu Val Val Asn Ala Phe Ala Val
                485                 490                 495

Asp Leu Glu Lys Ile Cys Glu Glu Leu Ala Ala Lys Gly Glu Gln Lys
            500                 505                 510

Ala Asp Ser Gly Met Ala Ala Met Tyr Gly Met Ala Ala Gln Val Pro
        515                 520                 525

Lys Ser Val Val Asp Glu Val Ile Ala Leu Tyr Ile Asp Ala Thr Tyr
    530                 535                 540

Ser Ala Pro Pro Ser Thr Ser Asn
545                 550

<210> SEQ ID NO 12
<211> LENGTH: 3162
<212> TYPE: DNA
<213> ORGANISM: C. elegans

<400> SEQUENCE: 12
atggattcgg ttaagcacac aaccgaaatt attgtcgact tgacaaaaat gcactatcac      60
atgataaatg ataggtgaat tttaaacaaa aattagatat ttggaaatta ctaattcaag     120
attttcagac tttctcggta tgatccggtt gttctagtgt tggccgcttt tgggggtacc     180
cttgtctata caaagtcgt ccatttgtac cgaaaaagcg aggatccaat tttgaaacgg      240
caagtgtttt cttgcgaatt ttagaaatat caaaatgaaa ttttcagcat gggagcttat     300
gtattctcac ttcttcgaaa acttccagct gttcgggata aaatcgaaaa agagctggct     360
gctgagaagc aaagcttat tgaatcgatt cataaggatg ataaggacaa gcaattcatt     420
tccagtttgt ttgaacattt attaattaac caattcatta attctatttt tcagctcttc     480
ccatcgctcc attatctcag gactcaatta tggaactggc gaaaaaatat gaggattaca     540
acacatttaa cattgacgga ggacgagtat ctggagcggt ttatactgat cgtcatgctg     600
aacacattaa tttgcttgga aaggtttaga aattctagaa ttttttcaaaa tcttagctct     660 caaatatatt ctcttgtaaa tagctacata gtatatcctg tagggaagct ttgaatccaa     720
```

```
ttcagatcag gggcgacaaa cgattttttc cggcaaatcg gcaaatcgcc ggaatggaaa    780
tttcctgcaa atcggcaaat tgccggaatg gaaatttcct gcaagttggc aaattgacgg    840
aattgaaatt tccggcaaac cgacaaattt ccgtaattaa aatttcctgc aaaccggcga    900
attggcggaa ttgaaatttc ctgcaaaccg gcaaattgcc gtaattgaaa tttcctgcaa    960
accggcaaat tgccggaatt gaaatttccg gcaaaccggc aaatcggctg aattgaaatt   1020
tcctgcaaac cggcaaattg cggtaattga atttcctgca aaaccggtca gttgccgatt   1080
tgcctttgcc tgaaaaacgg cgattgccag aaatattcgg caaattgtgg ttttgcacat   1140
ttttctggaa atttcaggca aaattgtacg catcctatga atatccctat aacatcttt    1200 tttgaaaagt cagtaaatta tatgaaaata tctaaagaaa acggggaaaa tatttcaaag   1260
aggcacagtt ttatgtgttt ccgtcatcta aatagtccct ctaaacattt ccggcaaatc   1320
tgatatccgg caaacggcaa atcgggatat tgccggaatt taaaatttgc gaacttgtc    1380 gacaaaaaaa atgcgccttg aatccgattc agatattcaa aaattgaatt ttggacgttt   1440
tagaaatcat ttagtttgtc aattttcaag aaatttctag aaaattggat ggtttccgcc   1500
aagaaatatt agctacatga aaataatttt gaaactagac atttcttaaa ataaaaattg   1560
ccatctttta tatccagatt tacgaaaagt atgcgttctc gaatcccctc caccctgacg   1620
tctttccggg agctcgtaaa atggaggcag aacttattcg aatggttctg aacctgtata   1680
atggaccaga agattctagt ggaagtgtaa cttctggtgg tactgaaagt attattatgg   1740
catgcttttc gtatcggtaa gcatttattc aactcttaaa attcaatttt gcaaactcta   1800
cagaaatcgt gcacactctc ttggcattga acatccagtt attttggcat gtaaaacagc   1860
tcacgcggca tttgataagg ccgcccatct atgcggaatg cgtcttcgcc acgttccagt   1920
tgattcggat aatcgtgtcg atttaaaaga aatggagaga ctaattgatt cgaatgtttg   1980
tatgttggtt ggctcagcgc ctaacttccc atcaggcaca attgatccaa ttccggaaat   2040
tgctaaggta ctggaaattc ccgcctcaat atcgcggaaa aaatagagaa atgactgaac   2100
aaaattacat tgtgagcggg aactctaatt gaattcagca aaaatacgat acttttttct   2160
aacttaaaat aattttttaaa aaaactcaca gatgctagtc caaaaaatgg cctttttttga   2220 ttacttaatc gaacgtttac actttcagct cggcaaaaag tatggaatcc cggtccacgt   2280
ggacgcatgt cttggtggat tcatgattcc atttatgaat gacgccggat acctgattcc   2340
tgtattcgat ttcagaaatc ccggtgttac atctatttcg tgtgatactc ataaggttgg   2400
atacagttct atccattttt ttccttcaat tcaaaatctt tcagtacgga tgcacaccga   2460
aaggttcatc gattgtcatg tatcgttcca aggaacttca tcacttccag tatttctcgg   2520
ttgccgattg gtgtggaggc atctatgcca ccccgactat tgcaggtttg aagaatgttt   2580
tagtagcttc aatagaatca aagagatccc ttaggatccc gagctggagc aacactgcc    2640 gtcgcctggg ccacactttt atccttcggt cgagacgaat atgttcgaag atgtgctcaa   2700
attgtgaagc atacacgaat gctggccgag aaaattgaga aaatcaaatg gatcaagcct   2760
tatgaaaaat cggatgtttc attggtggcg ttctccggaa atggtgtgaa tatctacgaa   2820
gtttctgaca aaatgatgaa gctcggatgg aatttgaaca ctctgcagaa tccagcggcg   2880
tatgtttatc aattttatga gttatcagct tgctaaattt tttgtttcag aatccacatt   2940
tgtttgacaa tcaatcaagc gaacgaggaa gttgtgaatg cgttcgccgt cgaccttgag   3000
aagatttgtg aagaactcgc tgcaaaaggt gaacaaaaag ctgacagtgg aatggctgcg   3060
```

```
atgtatggaa tggctgcgca agtaccaaaa tcagtagtgg acgaggttat cgctctgtac    3120
attgacgcaa cttattcagc tccaccttca acttctaatt aa                       3162

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
gaggaattca tggattcggt taagcacaca accg                                34

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
agcctcgagt taattagaag ttgaaggtgg agc                                 33

<210> SEQ ID NO 15
<211> LENGTH: 1638
<212> TYPE: DNA
<213> ORGANISM: Drosophila melanogaster

<400> SEQUENCE: 15
atgcgtccgt tctccggcag cgattgcctt aagcccgtca ccgagggcat caaccgggcg    60
ttcggcgcca aggagccctg gcaggtggcc accatcacgg ccaccacggt gctgggaggc    120
gtctggctct ggactgtgat ctgccaggat gaaaatcttt acattcgtgg caagcgtcag    180
ttctttaagt ttgccaagaa gattccagcc gtgcgtcgtc aggtggagac tgaattggcc    240
aaggccaaaa acgacttcga gacggaaatc aaaaagagca acgcccacct tacctactcg    300
gaaactctgc ccgagaaggg actcagcaag gaggagatcc tccgactggt ggatgagcac    360
ctgaagactg gtcactacaa ctggcgtgat ggtcgtgtat ctggcgcggt ctacggctac    420
aagcctgatc tggtggagct cgtcactgaa gtgtacggca aggcctccta caccaatccc    480
ttgcacgcag atcttttccc gggagtttgc aaaatggagg cggaggtagt gcgcatggca    540
tgcaacctgt tccatggaaa ctcagccagc tgtggaacca tgaccaccgg cggcaccgaa    600
tccattgtaa tggccatgaa ggcgtacagg gatttcgcta gagagtacaa gggaatcacc    660
aggccaaaca tcgtggtgcc taagacggtc cacgcggcct tcgacaaggg cggtcagtac    720
tttaatatcc acgtgcgatc cgtggatgta gatccggaga cctacgaagt ggacattaag    780
aagttcaaac gtgccattaa caggaacacg attctgctgg ttgggtctgc tccgaacttc    840
ccctatggaa ccatcgatga catcgaagct atcgccgctt gggcgttaa gtacgacatt    900 cccgtgcacg tggacgcctg cctgggcagc tttgtggtgg ccttggtccg caacgccggc    960
tataagctgc gtcccttcga ctttgaggtc aagggagtga ccagtatctc cgctgatacc    1020
cacaagtatg gtttcgcgcc caagggatca tcggtgatcc tttactcgga caagaagtac    1080
aaggaccatc agttcactgt gactactgac tggcctggcg gcgtgtatgg ttctcccaca    1140
gtcaacggtt cccgtgccgg aggtattatc gccgcctgct gggctaccat gatgagcttt    1200
ggctatgatg gttatctgga agccactaag cgcattgtgg atacggcgcg ctatatcgag    1260
aggggcgttc gcgacatcga tggcatcttt atctttggca agccagctac ttcagtgatt    1320
```

```
gccctgggtt ccaatgtgtt tgacattttc cggctatcgg attcgctgtg caaactgggc    1380
tggaacctaa atgcgctgca gtttccatct ggtatccacc tgtgcgtgac ggacatgcac    1440
acacagcccg gagtcgcgga taaattcatt gccgatgtgc gcagctgtac ggcggagatc    1500
atgaaggatc ccggccagcc cgtcgttgga aagatggctc tttacggcat ggcacagagc    1560
atacccgacc gttcggtgat cggagaagtg actcgcctat cctgcactc catgtactac     1620 actcccagcc agaaatag                                                  1638

<210> SEQ ID NO 16
<211> LENGTH: 545
<212> TYPE: PRT
<213> ORGANISM: Drosophila melanogaster

<400> SEQUENCE: 16
```

Met Arg Pro Phe Ser Gly Ser Asp Cys Leu Lys Pro Val Thr Glu Gly
 1               5                  10                  15

Ile Asn Arg Ala Phe Gly Ala Lys Glu Pro Trp Gln Val Ala Thr Ile
            20                  25                  30

Thr Ala Thr Thr Val Leu Gly Gly Val Trp Leu Trp Thr Val Ile Cys
        35                  40                  45

Gln Asp Glu Asn Leu Tyr Ile Arg Gly Lys Arg Gln Phe Phe Lys Phe
    50                  55                  60

Ala Lys Lys Ile Pro Ala Val Arg Arg Gln Val Glu Thr Glu Leu Ala
65                  70                  75                  80

Lys Ala Lys Asn Asp Phe Glu Thr Glu Ile Lys Lys Ser Asn Ala His
                85                  90                  95

Leu Thr Tyr Ser Glu Thr Leu Pro Glu Lys Gly Leu Ser Lys Glu Glu
            100                 105                 110

Ile Leu Arg Leu Val Asp Glu His Leu Lys Thr Gly His Tyr Asn Trp
        115                 120                 125

Arg Asp Gly Arg Val Ser Gly Ala Val Tyr Gly Tyr Lys Pro Asp Leu
    130                 135                 140

Val Glu Leu Val Thr Glu Val Tyr Gly Lys Ala Ser Tyr Thr Asn Pro
145                 150                 155                 160

Leu His Ala Asp Leu Phe Pro Gly Val Cys Lys Met Glu Ala Glu Val
                165                 170                 175

Val Arg Met Ala Cys Asn Leu Phe His Gly Asn Ser Ala Ser Cys Gly
            180                 185                 190

Thr Met Thr Thr Gly Gly Thr Glu Ser Ile Val Met Ala Met Lys Ala
        195                 200                 205

Tyr Arg Asp Phe Ala Arg Glu Tyr Lys Gly Ile Thr Arg Pro Asn Ile
    210                 215                 220

Val Val Pro Lys Thr Val His Ala Ala Phe Asp Lys Gly Gly Gln Tyr
225                 230                 235                 240

Phe Asn Ile His Val Arg Ser Val Asp Val Asp Pro Glu Thr Tyr Glu
                245                 250                 255

Val Asp Ile Lys Lys Phe Lys Arg Ala Ile Asn Arg Asn Thr Ile Leu
            260                 265                 270

Leu Val Gly Ser Ala Pro Asn Phe Pro Tyr Gly Thr Ile Asp Asp Ile
        275                 280                 285

Glu Ala Ile Ala Ala Leu Gly Val Lys Tyr Asp Ile Pro Val His Val
    290                 295                 300

Asp Ala Cys Leu Gly Ser Phe Val Ala Leu Val Arg Asn Ala Gly
305                 310                 315                 320

```
Tyr Lys Leu Arg Pro Phe Asp Phe Glu Val Lys Gly Val Thr Ser Ile
            325                 330                 335

Ser Ala Asp Thr His Lys Tyr Gly Phe Ala Pro Lys Gly Ser Ser Val
            340                 345                 350

Ile Leu Tyr Ser Asp Lys Lys Tyr Lys Asp His Gln Phe Thr Val Thr
            355                 360                 365

Thr Asp Trp Pro Gly Gly Val Tyr Gly Ser Pro Thr Val Asn Gly Ser
    370                 375                 380

Arg Ala Gly Gly Ile Ile Ala Ala Cys Trp Ala Thr Met Met Ser Phe
385                 390                 395                 400

Gly Tyr Asp Gly Tyr Leu Glu Ala Thr Lys Arg Ile Val Asp Thr Ala
            405                 410                 415

Arg Tyr Ile Glu Arg Gly Val Arg Asp Ile Asp Gly Ile Phe Ile Phe
            420                 425                 430

Gly Lys Pro Ala Thr Ser Val Ile Ala Leu Gly Ser Asn Val Phe Asp
            435                 440                 445

Ile Phe Arg Leu Ser Asp Ser Leu Cys Lys Leu Gly Trp Asn Leu Asn
            450                 455                 460

Ala Leu Gln Phe Pro Ser Gly Ile His Leu Cys Val Thr Asp Met His
465                 470                 475                 480

Thr Gln Pro Gly Val Ala Asp Lys Phe Ile Ala Asp Val Arg Ser Cys
            485                 490                 495

Thr Ala Glu Ile Met Lys Asp Pro Gly Gln Pro Val Val Gly Lys Met
            500                 505                 510

Ala Leu Tyr Gly Met Ala Gln Ser Ile Pro Asp Arg Ser Val Ile Gly
            515                 520                 525

Glu Val Thr Arg Leu Phe Leu His Ser Met Tyr Tyr Thr Pro Ser Gln
            530                 535                 540

Lys
545

<210> SEQ ID NO 17
<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 17 atg cct agc aca gac ctt ctg atg ttg aag gcc ttt gag ccc tac tta        48
Met Pro Ser Thr Asp Leu Leu Met Leu Lys Ala Phe Glu Pro Tyr Leu
 1                5                  10                  15 gag att ttg gaa gta tac tcc aca aaa gcc aag aat tat gta aat gga        96
Glu Ile Leu Glu Val Tyr Ser Thr Lys Ala Lys Asn Tyr Val Asn Gly
                 20                  25                  30 cat tgc acc aag tat gag ccc tgg cag cta att gca tgg agt gtc gtg       144
His Cys Thr Lys Tyr Glu Pro Trp Gln Leu Ile Ala Trp Ser Val Val
             35                  40                  45 tgg acc ctg ctg ata gtc tgg gga tat gag ttt gtc ttc cag cca gag       192
Trp Thr Leu Leu Ile Val Trp Gly Tyr Glu Phe Val Phe Gln Pro Glu
         50                  55                  60 agt tta tgg tca agg ttt aaa aag aaa tgt ttt aag ctc acc agg aag       240
Ser Leu Trp Ser Arg Phe Lys Lys Lys Cys Phe Lys Leu Thr Arg Lys
 65                  70                  75                  80 atg ccc att att ggt cgt aag att caa gac aag ttg aac aag acc aag       288
Met Pro Ile Ile Gly Arg Lys Ile Gln Asp Lys Leu Asn Lys Thr Lys
                 85                  90                  95
```

```
gat gat att agc aag aac atg tca ttc ctg aaa gtg gac aaa gag tat       336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag       384
Val Lys Ala Leu Pro Ser Gln Gly Leu Ser Ser Ser Ala Val Leu Glu
115                 120                 125 aaa ctt aag gag tac agc tct atg gac gcc ttc tgg caa gag ggg aga       432
Lys Leu Lys Glu Tyr Ser Ser Met Asp Ala Phe Trp Gln Glu Gly Arg
        130                 135                 140 gcc tct gga aca gtg tac agt ggg gag gag aag ctc act gag ctc ctt       480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat       528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct       576
Ile Phe Pro Gly Leu Arg Lys Ile Glu Ala Glu Ile Val Arg Ile Ala
            180                 185                 190 tgt tcc ctg ttc aat ggg gga cca gat tcg tgt gga tgt gtg act tct       624
Cys Ser Leu Phe Asn Gly Gly Pro Asp Ser Cys Gly Cys Val Thr Ser
        195                 200                 205 ggg gga aca gaa agc ata ctc atg gcc tgc aaa gca tat cgg gat ctg       672
Gly Gly Thr Glu Ser Ile Leu Met Ala Cys Lys Ala Tyr Arg Asp Leu
210                 215                 220 gcc ttt gag aag ggg atc aaa act cca gaa att gtg gct ccc caa agt       720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att       768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg       816
Val Arg Val Pro Leu Thr Lys Met Met Glu Val Asp Val Arg Ala Met
            260                 265                 270 aga aga gct atc tcc agg aac act gcc atg ctc gtc tgt tct acc cca       864
Arg Arg Ala Ile Ser Arg Asn Thr Ala Met Leu Val Cys Ser Thr Pro
        275                 280                 285 cag ttt cct cat ggt gta ata gat cct gtc cct gaa gtg gcc aag ctg       912
Gln Phe Pro His Gly Val Ile Asp Pro Val Pro Glu Val Ala Lys Leu
290                 295                 300 gct gtc aaa tac aaa ata ccc ctt cat gtc gac gct tgt ctg gga ggc       960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca      1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat      1056
Phe Asp Phe Arg Val Lys Gly Val Thr Ser Ile Ser Ala Asp Thr His
            340                 345                 350 aag tat ggc tat gcc cca aaa ggc tca tca ttg gtg ttg tat agt gac      1104
Lys Tyr Gly Tyr Ala Pro Lys Gly Ser Ser Leu Val Leu Tyr Ser Asp
        355                 360                 365 aag aag tac agg aac tat cag ttc ttc gtc gat aca gat tgg cag ggt      1152
Lys Lys Tyr Arg Asn Tyr Gln Phe Phe Val Asp Thr Asp Trp Gln Gly
370                 375                 380 ggc atc tat gct tcc cca acc atc gca ggc tca cgg cct ggt ggc att      1200
Gly Ile Tyr Ala Ser Pro Thr Ile Ala Gly Ser Arg Pro Gly Gly Ile
385                 390                 395                 400 agc gca gcc tgt tgg gct gcc ttg atg cac ttc ggt gag aac ggc tat      1248
Ser Ala Ala Cys Trp Ala Ala Leu Met His Phe Gly Glu Asn Gly Tyr
                405                 410                 415
```

-continued

```
gtt gaa gct acc aaa cag atc atc aaa act gct cgc ttc ctc aag tca      1296
Val Glu Ala Thr Lys Gln Ile Ile Lys Thr Ala Arg Phe Leu Lys Ser
        420                 425                 430 gaa ctg gaa aat atc aaa ggc atc ttt gtt ttt ggg aat ccc caa ttg      1344
Glu Leu Glu Asn Ile Lys Gly Ile Phe Val Phe Gly Asn Pro Gln Leu
435                 440                 445 tca gtc att gct ctg gga tcc cgt gat ttt gac atc tac cga cta tca      1392
Ser Val Ile Ala Leu Gly Ser Arg Asp Phe Asp Ile Tyr Arg Leu Ser
    450                 455                 460 aac ctg atg act gct aag ggg tgg aac ttg aac cag ttg cag ttc cca      1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta      1488
Pro Ser Ile His Phe Cys Ile Thr Leu Leu His Ala Arg Lys Arg Val
                485                 490                 495 gct ata caa ttc cta aag gac att cga gaa tct gtc act caa atc atg      1536
Ala Ile Gln Phe Leu Lys Asp Ile Arg Glu Ser Val Thr Gln Ile Met
            500                 505                 510 aag aat cct aaa gcg aag acc aca gga atg ggt gcc atc tat ggc atg      1584
Lys Asn Pro Lys Ala Lys Thr Thr Gly Met Gly Ala Ile Tyr Gly Met
        515                 520                 525 gcc cag aca act gtt gac agg aat atg gtt gca gaa ttg tcc tca gtc      1632
Ala Gln Thr Thr Val Asp Arg Asn Met Val Ala Glu Leu Ser Ser Val
530                 535                 540 ttc ttg gac agc ttg tac agc acc gac act gtc acc cag ggc agc cag      1680
Phe Leu Asp Ser Leu Tyr Ser Thr Asp Thr Val Thr Gln Gly Ser Gln
545                 550                 555                 560 atg aat ggt tct cca aaa ccc cac tga                                   1707
Met Asn Gly Ser Pro Lys Pro His *
                565

<210> SEQ ID NO 18
<211> LENGTH: 568
<212> TYPE: PRT
<213> ORGANISM: Homo sapiens

<400> SEQUENCE: 18

Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ala Val Leu Glu
        115                 120                 125

Lys Leu Lys Glu Tyr Ser Ser Met Asp Ala Phe Trp Gln Glu Gly Arg
    130                 135                 140

Ala Ser Gly Thr Val Tyr Ser Gly Glu Glu Lys Leu Thr Glu Leu Leu
145                 150                 155                 160
```

-continued

```
Val Lys Ala Tyr Gly Asp Phe Ala Trp Ser Asn Pro Leu His Pro Asp
            165                 170                 175
Ile Phe Pro Gly Leu Arg Lys Ile Glu Ala Glu Ile Val Arg Ile Ala
            180                 185                 190
Cys Ser Leu Phe Asn Gly Gly Pro Asp Ser Cys Gly Cys Val Thr Ser
            195                 200                 205
Gly Gly Thr Glu Ser Ile Leu Met Ala Cys Lys Ala Tyr Arg Asp Leu
    210                 215                 220
Ala Phe Glu Lys Gly Ile Lys Thr Pro Glu Ile Val Ala Pro Gln Ser
225                 230                 235                 240
Ala His Ala Ala Phe Asn Lys Ala Ala Ser Tyr Phe Gly Met Lys Ile
                245                 250                 255
Val Arg Val Pro Leu Thr Lys Met Met Glu Val Asp Val Arg Ala Met
            260                 265                 270
Arg Arg Ala Ile Ser Arg Asn Thr Ala Met Leu Val Cys Ser Thr Pro
            275                 280                 285
Gln Phe Pro His Gly Val Ile Asp Pro Val Pro Glu Val Ala Lys Leu
    290                 295                 300
Ala Val Lys Tyr Lys Ile Pro Leu His Val Asp Ala Cys Leu Gly Gly
305                 310                 315                 320
Phe Leu Ile Val Phe Met Glu Lys Ala Gly Tyr Pro Leu Glu His Pro
                325                 330                 335
Phe Asp Phe Arg Val Lys Gly Val Thr Ser Ile Ser Ala Asp Thr His
            340                 345                 350
Lys Tyr Gly Tyr Ala Pro Lys Gly Ser Ser Leu Val Leu Tyr Ser Asp
            355                 360                 365
Lys Lys Tyr Arg Asn Tyr Gln Phe Phe Val Asp Thr Asp Trp Gln Gly
    370                 375                 380
Gly Ile Tyr Ala Ser Pro Thr Ile Ala Gly Ser Arg Pro Gly Gly Ile
385                 390                 395                 400
Ser Ala Ala Cys Trp Ala Ala Leu Met His Phe Gly Glu Asn Gly Tyr
                405                 410                 415
Val Glu Ala Thr Lys Gln Ile Ile Lys Thr Ala Arg Phe Leu Lys Ser
            420                 425                 430
Glu Leu Glu Asn Ile Lys Gly Ile Phe Val Phe Gly Asn Pro Gln Leu
            435                 440                 445
Ser Val Ile Ala Leu Gly Ser Arg Asp Phe Asp Ile Tyr Arg Leu Ser
    450                 455                 460
Asn Leu Met Thr Ala Lys Gly Trp Asn Leu Asn Gln Leu Gln Phe Pro
465                 470                 475                 480
Pro Ser Ile His Phe Cys Ile Thr Leu Leu His Ala Arg Lys Arg Val
                485                 490                 495
Ala Ile Gln Phe Leu Lys Asp Ile Arg Glu Ser Val Thr Gln Ile Met
            500                 505                 510
Lys Asn Pro Lys Ala Lys Thr Thr Gly Met Gly Ala Ile Tyr Gly Met
            515                 520                 525
Ala Gln Thr Thr Val Asp Arg Asn Met Val Ala Glu Leu Ser Ser Val
    530                 535                 540
Phe Leu Asp Ser Leu Tyr Ser Thr Asp Thr Val Thr Gln Gly Ser Gln
545                 550                 555                 560
Met Asn Gly Ser Pro Lys Pro His
            565
```

<210> SEQ ID NO 19
<211> LENGTH: 490
<212> TYPE: PRT
<213> ORGANISM: Drosophila melanogaster

<400> SEQUENCE: 19

Phe Arg Ser Ser Asn Asp Tyr Gly Val Asn Leu Gln Thr Ala Glu Met
1               5                   10                  15

Trp His His Thr Ile Arg Lys His Lys Arg Gly Asn Gly Ser Ser Ser
            20                  25                  30

Pro Ala Asp Cys Gly Lys Gln Leu Ile Leu Leu Asn Pro Lys Ser
        35                  40                  45

Gly Ser Gly Lys Gly Arg Glu Leu Phe Gln Lys Gln Val Ala Pro Leu
    50                  55                  60

Leu Thr Glu Ala Glu Val Gln Tyr Asp Leu Gln Ile Thr Thr His Pro
65                  70                  75                  80

Gln Tyr Ala Lys Glu Phe Val Arg Thr Arg Arg Asp Leu Leu Thr Arg
                85                  90                  95

Tyr Ser Gly Ile Val Val Ala Ser Gly Asp Gly Leu Phe Tyr Glu Val
            100                 105                 110

Leu Asn Gly Leu Met Glu Arg Met Asp Trp Arg Arg Ala Cys Arg Glu
        115                 120                 125

Leu Pro Leu Gly Ile Ile Pro Cys Gly Ser Gly Asn Gly Leu Ala Lys
    130                 135                 140

Ser Val Ala His His Cys Asn Glu Pro Tyr Glu Pro Lys Pro Ile Leu
145                 150                 155                 160

His Ala Thr Leu Thr Cys Met Ala Gly Lys Ser Thr Pro Met Asp Val
                165                 170                 175

Val Arg Val Glu Leu Ala Thr Arg Asp Lys His Phe Val Met Tyr Ser
            180                 185                 190

Phe Leu Ser Val Gly Trp Gly Leu Ile Ala Asp Ile Asp Ile Glu Ser
        195                 200                 205

Glu Arg Leu Arg Ser Ile Gly Ala Gln Arg Phe Thr Leu Trp Ala Ile
    210                 215                 220

Lys Arg Leu Ile Gly Leu Arg Ser Tyr Lys Gly Arg Val Ser Tyr Leu
225                 230                 235                 240

Leu Gly Lys Gly Lys Lys Glu Pro Pro Val Glu Ala Ala Arg Glu Leu
                245                 250                 255

Pro Ala Glu Ser Thr Ala Ala Gly Ile Arg Ser Ser Leu Pro Leu Asn
            260                 265                 270

Ala Gly Glu Phe His Asp Leu Pro Glu Glu Glu Gly Glu Ala Val
        275                 280                 285

Leu Asp Gly Glu Gln Phe Ala Asp Ala Ile Ser Leu Asp Arg Ser Val
    290                 295                 300

Tyr Arg Gln His Ala Asp Ser Trp His Ser Ala Met Ser Arg Arg Thr
305                 310                 315                 320

Ala Tyr Tyr Ser Leu Gly Gly Pro Ser Met Arg Ser Asn Arg Ser Arg
                325                 330                 335

Met Ser Ile Ser Gln Arg Ile Glu Ala Ala Asn Ala Glu Phe Ala Glu
            340                 345                 350

Arg Val Pro Thr Gly Thr Ile Pro Leu Gln Met Pro Leu Leu Ser
        355                 360                 365

Ser Asp Gly Trp Ile Cys Glu Asp Gly Asp Phe Val Met Val His Ala
    370                 375                 380

```
Ala Tyr Thr Thr His Leu Ser Ser Asp Val Phe Phe Ala Pro Glu Ser
385                 390                 395                 400

Arg Leu Asp Asp Gly Leu Ile Tyr Leu Val Ile Ile Arg Arg Gly Val
            405                 410                 415

Ser Arg His Gln Leu Leu Asn Phe Met Leu Asn Leu Asn Ala Gly Thr
            420                 425                 430

His Leu Pro Ile Gly Glu Asp Pro Phe Ile Lys Val Val Pro Cys Arg
            435                 440                 445

Ala Phe Arg Ile Glu Pro Ser Ser Asp Gly Ile Leu Val Val Asp
450                 455                 460

Gly Glu Arg Val Glu Tyr Gly Pro Ile Gln Ala Glu Val Met Pro Gly
465                 470                 475                 480

Leu Ile Asn Val Met Thr Thr Ser Gly Gln
                485                 490

<210> SEQ ID NO 20
<211> LENGTH: 524
<212> TYPE: PRT
<213> ORGANISM: Drosophila melanogaster

<400> SEQUENCE: 20

Phe Arg Ser Phe Asp Thr Phe Glu Asp Asn Met Arg Glu Ala Asp Arg
1               5                   10                  15

Trp Tyr Arg Ser Leu Arg Trp Gln Leu His Arg Thr Leu Glu Glu Ile
                20                  25                  30

Phe Val Ala Pro Thr Val Asp Glu Arg Arg Arg Val Leu Val Leu
            35                  40                  45

Leu Asn Pro Lys Ser Gly Ser Gly Asp Ala Arg Glu Val Phe Asn Met
50                  55                  60

His Val Thr Pro Val Leu Asn Glu Ala Glu Val Pro Tyr Asp Leu Tyr
65                  70                  75                  80

Val Thr Lys His Ser Asn Phe Ala Ile Glu Phe Leu Ser Thr Arg Cys
                85                  90                  95

Leu Asp Ala Trp Cys Cys Val Val Ala Val Gly Gly Asp Gly Leu Phe
            100                 105                 110

His Glu Ile Val Asn Gly Leu Leu Gln Arg Gln Asp Trp Ala His Val
            115                 120                 125

Leu Pro His Leu Ala Leu Gly Ile Ile Pro Cys Gly Ser Gly Asn Gly
130                 135                 140

Leu Ala Arg Ser Ile Ala His Cys Tyr Asn Lys Pro Val Leu Gly Ala
145                 150                 155                 160

Ala Leu Thr Val Ile Ser Gly Arg Ser Ser Pro Met Asp Val Val Arg
                165                 170                 175

Val Gln Leu Gln Ser Arg Ser Leu Tyr Ser Phe Leu Ser Ile Gly Trp
            180                 185                 190

Gly Leu Ile Ser Asp Val Asp Ile Glu Ser Glu Arg Ile Arg Met Leu
            195                 200                 205

Gly Tyr Gln Arg Phe Thr Val Trp Thr Leu Tyr Arg Leu Val Asn Leu
210                 215                 220

Arg Thr Tyr Asn Gly Arg Ile Ser Tyr Leu Leu Thr Asp His Glu Val
225                 230                 235                 240

Ser Ser Thr His Ser Ala Thr Gly Tyr Ala Ala Gln Arg Arg Met Gln
                245                 250                 255

Ser Ser Arg Ser Cys Asn Thr His Ile Asp Met Leu Asn Gly Pro Ala
            260                 265                 270
```

Pro Ile Tyr His Ser Ser Ala Glu Tyr Leu Pro Gln Glu Phe Ala Asp
         275                 280                 285

Val Ile Ser Leu Glu Thr Ser Ile Asn Gln Ser Phe Arg Ser Arg Cys
         290                 295                 300

Asp Ser Trp Leu Ser Gly Gly Ser Arg Arg Ser Phe Tyr Tyr Ser Ile
305                 310                 315                 320

Ser Glu Ser Ile Tyr His Ser Leu Ala Asp Glu Ser Glu Phe Ala Gly
                 325                 330                 335

Leu Ala Ala Ser Leu Glu Asn Arg Gln Gln Asn Tyr Gly Pro Ala
         340                 345                 350

Ser Glu Leu Pro Asp Leu Asn Glu Pro Leu Ser Glu Asp Gln Gly Trp
         355                 360                 365

Leu Val Glu Glu Gly Glu Phe Val Met Met His Ala Val Tyr Gln Thr
         370                 375                 380

His Leu Gly Ile Asp Cys His Phe Ala Pro Lys Ala Gln Leu Asn Asp
385                 390                 395                 400

Gly Thr Ile Tyr Leu Ile Leu Ile Arg Ala Gly Ile Ser Arg Pro His
                 405                 410                 415

Leu Leu Ser Phe Leu Tyr Asn Met Ser Ser Gly Thr His Leu Pro Glu
         420                 425                 430

Ser His Asp Asp His Val Lys Val Leu Pro Val Arg Ala Phe Arg Leu
         435                 440                 445

Glu Pro Tyr Asp Asn His Gly Ile Ile Thr Val Asp Gly Glu Arg Val
         450                 455                 460

Glu Phe Gly Pro Leu Gln Ala Glu Val Leu Pro Gly Ile Ala Arg Val
465                 470                 475                 480

Met Val Pro Asn Val Ser Thr Phe Arg Phe Gln Ser Ala Thr Leu Gln
                 485                 490                 495

His Gly Ile Pro Val Cys Ile Pro Val Arg Lys Arg Phe Val Leu Tyr
         500                 505                 510

Asn Met Ser Ser Glu Glu Leu Ala Pro Ile Asn Glu
         515                 520

<210> SEQ ID NO 21
<211> LENGTH: 368
<212> TYPE: PRT
<213> ORGANISM: Homo sapiens

<400> SEQUENCE: 21

Val Leu Val Leu Leu Asn Pro Arg Gly Gly Lys Gly Lys Ala Leu Gln
1               5                   10                  15

Leu Phe Arg Ser His Val Gln Pro Leu Leu Ala Glu Ala Glu Ile Ser
         20                  25                  30

Phe Thr Leu Met Leu Thr Glu Arg Arg Asn His Ala Arg Glu Leu Val
         35                  40                  45

Arg Ser Glu Glu Leu Gly Arg Trp Asp Ala Leu Val Val Met Ser Gly
         50                  55                  60

Asp Gly Leu Met His Glu Val Val Asn Gly Leu Met Glu Arg Pro Asp
65                  70                  75                  80

Trp Glu Thr Ala Ile Gln Lys Pro Leu Cys Ser Leu Pro Ala Gly Ser
                 85                  90                  95

Gly Asn Ala Leu Ala Ala Ser Leu Asn His Tyr Ala Gly Tyr Glu Gln
         100                 105                 110

Val Thr Asn Glu Asp Leu Leu Thr Asn Cys Thr Leu Leu Leu Cys Arg
         115                 120                 125

```
Arg Leu Leu Ser Pro Met Asn Leu Leu Ser Leu His Thr Ala Ser Gly
    130                 135                 140

Leu Arg Leu Phe Ser Val Leu Ser Leu Ala Trp Gly Phe Ile Ala Asp
145                 150                 155                 160

Val Asp Leu Glu Ser Glu Lys Tyr Arg Arg Leu Gly Glu Met Arg Phe
                165                 170                 175

Thr Leu Gly Thr Phe Leu Arg Leu Ala Ala Leu Arg Thr Tyr Arg Gly
            180                 185                 190

Arg Leu Ala Tyr Leu Pro Val Gly Arg Val Gly Ser Lys Thr Pro Ala
        195                 200                 205

Ser Pro Val Val Gln Gln Gly Pro Val Asp Ala His Leu Val Pro
    210                 215                 220

Leu Glu Glu Pro Val Pro Ser His Trp Thr Val Val Pro Asp Glu Asp
225                 230                 235                 240

Phe Val Leu Val Leu Ala Leu Leu His Ser His Leu Gly Ser Glu Met
                245                 250                 255

Phe Ala Ala Pro Met Gly Arg Cys Ala Ala Gly Val Met His Leu Phe
            260                 265                 270

Tyr Val Arg Ala Gly Val Ser Arg Ala Met Leu Leu Arg Leu Phe Leu
        275                 280                 285

Ala Met Glu Lys Gly Arg His Met Glu Tyr Glu Cys Pro Tyr Leu Val
    290                 295                 300

Tyr Val Pro Val Val Ala Phe Arg Leu Glu Pro Lys Asp Gly Lys Gly
305                 310                 315                 320

Val Phe Ala Val Asp Gly Glu Leu Met Val Ser Glu Ala Val Gln Gly
                325                 330                 335

Gln Val His Pro Asn Tyr Phe Trp Met Val Ser Gly Cys Val Glu Pro
            340                 345                 350

Pro Pro Ser Trp Lys Pro Gln Gln Met Pro Pro Glu Glu Pro Leu
        355                 360                 365

<210> SEQ ID NO 22
<211> LENGTH: 1152
<212> TYPE: DNA
<213> ORGANISM: Homo sapiens

<400> SEQUENCE: 22
atggatccag cgggcggccc ccggggcgtg ctcccgcggc cctgccgcgt gctggtgctg      60
ctgaacccgc gcggcggcaa gggcaaggcc ttgcagctct ccggagtca cgtgcagccc     120 cttttggctg aggctgaaat ctccttcacg ctgatgctca ctgagcggcg gaaccacgcg     180
cgggagctgt gcggtcgga ggagctgggc cgctgggacg tctggtggt catgtctgga     240 gacgggctga tgcacgaggt ggtgaacggg ctcatggagc ggcctgactg ggagaccgcc     300
atccagaagc ccctgtgtag cctcccagca ggctctggca acgcgctggc agcttccttg     360
aaccattatg ctggctatga gcaggtcacc aatgaagacc tcctgaccaa ctgcacgcta     420
ttgctgtgcc gccggctgct gtcacccatg aacctgctgt ctctgcacac ggcttcgggg     480
ctgcgcctct ctctgtgct cagcctggcc tgggcttca ttgctgatgt ggacctagag     540
agtgagaagt atcggcgtct gggggagatg cgcttcactc tgggcacctt cctgcgtctg     600
gcagccctgc gcacctaccg cggccgactg gcctacctcc ctgtaggaag agtgggttcc     660
aagacacctg cctcccccgt gtggtccag cagggcccgg tagatgcaca ccttgtgcca     720
ctggaggagc cagtgccctc tcactggaca gtggtgcccg acgaggactt gtgctagtc     780
```

```
ctggcactgc tgcactcgca cctgggcagt gagatgtttg ctgcacccat gggccgctgt      840
gcagctggcg tcatgcatct gttctacgtg cgggcgggag tgtctcgtgc catgctgctg      900
cgcctcttcc tggccatgga aagggcagg catatggagt atgaatgccc ctacttggta       960
tatgtgcccg tggtcgcctt ccgcttggag cccaaggatg ggaaaggtgt gtttgcagtg     1020
gatggggaat tgatggttag cgaggccgtg cagggccagg tgcacccaaa ctacttctgg     1080
atggtcagtg gttgcgtgga gcccccgccc agctggaagc cccagcagat gccaccgcca     1140
gaagagccct ta                                                         1152
```

<210> SEQ ID NO 23
<211> LENGTH: 1707
<212> TYPE: DNA
<213> ORGANISM: Homo sapiens

<400> SEQUENCE: 23

```
atgcctagca cagaccttct gatgttgaag gcctttgagc cctacttaga gattttggaa       60
gtatactcca caaaagccaa gaattatgta aatggacatt gcaccaagta tgagccctgg      120
cagctaattg catggagtgt cgtgtggacc ctgctgatag tctggggata tgagtttgtc      180
ttccagccag agagtttatg gtcaaggttt aaaaagaaat gttttaagct caccaggaag      240
atgcccatta ttggtcgtaa gattcaagac aagttgaaca agaccaagga tgatattagc      300
aagaacatgt cattcctgaa agtggacaaa gagtatgtga agctttaccc tcccagggt      360 ctgagctcat ctgctgtttt ggagaaactt aaggagtaca gctctatgga cgccttctgg      420
caagagggga gagcctctgg aacagtgtac agtggggagg agaagctcac tgagctcctt      480
gtgaaggctt atggagattt gcatggagt aaccccctgc atccagatat cttcccagga      540
ctacgcaaga tagaggcaga aattgtgagg atagcttgtt ccctgttcaa tggggaccca      600
gattcgtgtg gatgtgtgac ttctggggga acagaaagca tactgatggc ctgcaaagca      660
tatcgggatc tggcctttga aagggatc aaaactccag aaattgtggc tccccaaagt       720
gcccatgctg catttaacaa agcagccagt tactttggga tgaagattgt gcgggtccca      780
ttgacgaaga tgatggaggt ggatgtgcgg gcaatgagaa gagctatctc caggaacact      840
gccatgctcg tctgttctac cccacagttt cctcatggtg taatagatcc tgtccctgaa      900
gtggccaagc tggctgtcaa atacaaaata ccccttcatg tcgacgcttg tctgggaggc      960
ttcctcatcg tctttatgga aaagcagga tacccactgg agcacccatt tgatttccgg      1020
gtgaaaggtg taaccagcat ttcagctgac acccataagt atggctatgc cccaaaaggc     1080
tcatcattgg tgttgtatag tgacaagaag tacaggaact atcagttctt cgtcgataca     1140
gattggcagg gtgcatcta tgcttcccca accatcgcag gctcacggcc tggtggcatt      1200
agcgcagcct gttgggctgc cttgatgcac ttcggtgaga acggctatgt gaagctacc      1260 aaacagatca tcaaaactgc tcgcttcctc aagtcagaac tggaaaatat caaaggcatc      1320
tttgtttttg ggaatcccca attgtcagtc attgctctgg atcccgtga ttttgacatc       1380 taccgactat caaacctgat gactgctaag gggtggaact tgaaccagtt gcagttccca      1440
cccagtattc atttctgcat cacattacta cacgcccgga aacgagtagc tatacaattc      1500
ctaaaggaca ttcgagaatc tgtcactcaa atcatgaaga atcctaaagc gaagaccaca     1560
ggaatgggtg ccatctatgg catggcccag acaactgttg acaggaatat ggttgcagaa     1620
ttgtcctcag tcttcttgga cagcttgtac agcaccgaca ctgtcaccca gggcagccag     1680
atgaatggtt ctccaaaacc ccactga                                         1707
```

```
<210> SEQ ID NO 24
<211> LENGTH: 2629
<212> TYPE: DNA
<213> ORGANISM: Drosophila melanogaster

<400> SEQUENCE: 24
agtacgaatt gtcgtgtcaa gcgcacagga agcgatcgca acccggatcg gattggatcg      60
gccggatcga gccaccatat gtactatata caaacacaca tatatatata gatatatcgc     120
agtctttacg gtgaacagcg tcgatcgcat gtggacaaac aattaaatac aaggtcaaag     180
aagcgctaaa aagtgaagtt aagtcgaaac aaacacgaag ataccaaaga agatatgacg     240
gccaacacag ggacgtcggg tgaaaatctg atgggaaatg gtggaaagac gcatgaaccc     300
tccacgccca cttcggatac ggaagtggcc agcggcacgc caacgaaact gagcgaaatc     360
ttcttcgtgg acaatagccg gcgcaagcag agcatcaaaa tccaggtgaa actatgcccg     420
gaaggcgttt acctgcgacg cgaaaccgag gaagatgatc acatcaatga gcagctgatc     480
aggatcgatg atatcatagg atcacgctac ggacggcgtt tgaagaaacg agcccgaggc     540
ggtctaaact cctgccgcaa tccaaatgtt ccgggccagg aggcggattc ggaaccggat     600
agcgataata gcgcctattt gtacatctat gcatatttga agaaggagaa accgttgcga     660
cgtgtccaaa cgctccggat tctacgcttt cgttcgagca atgactacgg agtgaatcta     720
cagaccgccg agatgtggca tcatacgatt cgaaagcaca agcgtggcaa tggcagcagt     780
tcgcccgccg attgtggcaa acagttgctc atcctactga atccgaaatc cggttcgggc     840
aaagggcgtg agctcttcca gaaacaggtg gcacctttgc tgacggaagc agaggtgcaa     900
tacgatctcc agatcaccac acatccgcag tatgccaagg agttcgtgcg gaccagaagg     960
gatctgctga cacgctattc gggcattgtg gttgcctccg gcgatggtct attctacgaa    1020
gtgctcaatg ggctaatgga acgcatggat tggcgccgag cctgcaggga gctaccgctt    1080
ggcattatac catgtggttc cgggaatggt ctggccaaaa gtgtggccca tcattgcaat    1140
gaaccgtacg aaccgaagcc cattctccac gccaccttga cctgcatggc gggcaaaagt    1200
acacccatgg atgtggtcag agtggagctg gcgacgcggg acaagcactt tgtgatgtac    1260
tccttcctgt cggtgggctg gggtctgata gccgacatcg atatagagag cgagcgattg    1320
agatcgattg gagcgcaaag gtttacgctg tgggccatca gcgattgat cgggctgcgc    1380 agctacaaag gccgagtgtc ctatctactg ggcaagggca agaaggaacc accagtggaa    1440
gcggctcgag agttgcctgc agaatcaacg gctgcaggaa tccgctcatc tctgcctctg    1500
aatgccgggg aattccatga tctacccgag gaggaggagg gggaggcggt cttggatgga    1560
gaacagttcg ccgatgccat atctttggat cgttcggttt accgccagca tgccgacagt    1620
tggcactcgg ccatgtccag gcgaacggca tattactccc tgggcggacc cagtatgcga    1680
tccaatcgca gccggatgag cattagccag cggatcgagg cagcaaatgc ggaattcgct    1740
gagagggtgc caacgggcac cattccacca ttacagatgc cactgctcag cagcgatggt    1800
tggatctgcg aggatggtga ctttgtgatg gtccatgccg cctataccac ccatctctcc    1860
tccgatgtct tctttgcgcc cgaatcccgt ctggacgatg gcctcatcta cctggtgatc    1920
atccggagag gcgttagtcg ccatcagctg ctcaatttca tgctgaacct aaacgcaggc    1980
acccatctgc ccatcggcga ggatccgttc atcaaggtgg tgccttgtcg ggcattccgc    2040
atcgagccgc gcagctccga tggcatcctg gtggtggacg gcgagcgggt ggaatatgga    2100
cccattcagg cggaggttat gcccggcctg atcaatgtga tgaccaccag tgggcagtag    2160
```

```
tgaaatatta aatccgtgtg ctttgcaaag ccttaatcat aacgagatac attcgaagaa      2220
tgtcaacatt caatagctac tttagatcaa acttagttta taagaagttg cctttccaat      2280
taataaccct tactaaattc ataacttttt tatatctgct aggaactttt tccaaagttt      2340
acgcattttg acattattag gtggtaaagt tcacaaaatt tctattatct ctgtttctat      2400
tgttagtgaa aacccattct catggctctg aaacgcaatc tgtaattttt ccatcagccc      2460
atcaaaaaaa aaaaggaac ttcacactat gcacttaagt agttggttat aagttgtttt      2520
ctattatttt tttttttttt aatcggtcga tagtgttaat tattttaaga accatacgta      2580
gacaaataat aaaccaaaat gctataaaaa atgttaaaaa aaaaaaaaa                  2629

<210> SEQ ID NO 25
<211> LENGTH: 2609
<212> TYPE: DNA
<213> ORGANISM: Drosophila melanogaster

<400> SEQUENCE: 25
ctgccaccga cggtaacact gcggctatga ttggatgata agcgatccat aaaagcctgg        60 acacaaaga cctgaaacat gctgcttggc agccgaatct ccagtcgaaa tgagcgaatc       120
tcttgataag accaccagcc cgagctcggc cagttccagg ccacgcccc cgggaacgca       180 ggatgcggat gagggccacg acgtgagcga taccttctac acgagccagc gcaagaaggg       240
cagccacgta tttcgggtgc gccttgacgc cacaggattc accctgcagc gggagtcgcc       300
gggcggtagc attgttaagg agcaacatgt ccgcatatcg acattgtgg gtgcccgctg       360 catgcggccc aagaagagcc ggcgcctggc gatgtcgggc gcctgtgcgt gcagctccgg       420
taatcccaat tcgccagcca tctcggcgtc cggcgatcac catcgccctg ccaccacacc       480
aagcaaatgc agcaccaata gtcgggataa tattccttcg gatggcggcg atgtcagcgc       540
gtttctctac gttttgcct atgttctgaa gaagaggagc ctgcggtcgg agttgcaccg       600
ggagcgaacg gtgctcactc tgcgcttccg gtcgttcgac accttcgagg acaacatgag       660
ggaggcggat cgttggtaca gatcccttcg ctggcagttg catcgcacgc tggaggagat       720
ctttgtggcg ccgacggtgg atgagcgacg ccgtcgagtg cttgtgctgt tgaatcccaa       780
atccggttcc ggtgacgctc gtgaggtctt caacatgcac gtgacgccgg tgctcaacga       840
ggccgaggtg ccctacgacc tgtatgtaac caagcattcc aactttgcca tcgagttctt       900
gagcaccagg tgcctggacg cctggtgctg cgtggtggct gtcggcggag acggtctctt       960
ccacgagata gtcaatggac tgctgcagcg ccaggactgg gcccacgtcc tgcctcatct      1020
ggcactggga atcattcctt gcggctccgg aaatggattg gcccgctcca ttgcccattg      1080
ttacaacaag ccagtgctag agctgctct gaccgtaatc agtggacgca gttcaccccat      1140 ggacgtggtc cgggtgcagc tgcagagtcg ctccctctac tccttcctgt ccatcggctg      1200
gggtctgatc tcggacgtgg acatcgagag cgagcgcatt cgcatgttgg gctaccagcg      1260
cttcaccgtg tggaccctct accgtctggt gaatctgcgc acctacaacg gccgaatcag      1320
ctatcttctg acgaccatg aggtgtcctc aaccccatagc gctaccggtt atgctgccca      1380
gcggagaatg cagagcagcc gtagctgcaa cacgcacatc gacatgctaa atgggccggc      1440
gcccatctat cattccagtg ccgagtacct gccacaggag tttgcggacg tgatctccct      1500
ggagacgtcc atcaatcagt cgttccgctc gaggtgcgac agctggttgt cggggggatc      1560
gcggcgcagc ttttactatt ccatatcgga gagcatctac cacagtctgg cggatgagag      1620
cgagttcgcc ggcctggcgg ccgcctcgct ggaaaaccgg cagcagaact acggtccggc      1680
```

-continued

| | |
|---|---|
| aagcgagctg ccggatctga acgaaccgct gtccgaggat cagggttggc tggtggagga | 1740 |
| gggcgagttc gtcatgatgc acgccgttta ccagacccat ctgggcatcg actgtcattt | 1800 |
| tgcgcccaag gcccagctga acgacggcac catctacctg atcctcatac gcgccggcat | 1860 |
| cagccgcccg cacctgctga gcttcctcta caacatgagc tccggcactc acctgccgga | 1920 |
| gtcgcacgac gaccatgtga aggtgctgcc agtgcgagca ttccgcctgg agccctacga | 1980 |
| caatcacggc atcatcacgg tcgacggcga gcgcgtcgag ttcgggcccc tccaagctga | 2040 |
| ggtcctgccg gcatagcccg cgtcatggt gcccaagtag gaggagctta ctgaagacca | 2100 |
| tcaagcaata gaaatctcaa ttttggaatc tctgcatttg tagctaatac ttagggtccc | 2160 |
| aggtggccga tatgagagag ttgtgcattc tacatatttc gtgttttgt ggcctgcttc | 2220 |
| tgccaaccaa tcatgtattg ttaacatttt aaacacaata acagctattt ccgaaatatc | 2280 |
| taacatgttt gtttataaaa cgtgtgccat atgaagtgca cgtgaattta ttttatctc | 2340 |
| ggctgttcaa aatagcgatg aaagtcttat ttattttgtt ctttttttt ttaaactgtg | 2400 |
| taacgaaatg agatatatat tcaaaatgtt taaagatgaa tacaaataaa tcttcatgaa | 2460 |
| ttcaaaaatc ttagaaagta acagtgtaag taacagagct aaatcattta caattccata | 2520 |
| ttttaaagta ggaagttaag aatataacat ctttgagctt gaaataaaaa ataaaaatgt | 2580 |
| taactaaaaa aaaaaaaaaa aaaaaaaa | 2609 |

<210> SEQ ID NO 26
<211> LENGTH: 2043
<212> TYPE: DNA
<213> ORGANISM: Drosophila melanogaster

<400> SEQUENCE: 26

| | |
|---|---|
| gtcactctaa gccgcaatga gtttgtacga ttaaaagttt atgtctattc gcgttttcg | 60 |
| aagctttccc gattcccgta gctgtcccac tgtacagctt gccacacgat gcgtccgttc | 120 |
| tccggcagcg attgccttaa gcccgtcacc gagggcatca accgggcgtt cggcgccaag | 180 |
| gagccttggc aggtcgccac catcacggcc accacggtgc tgggaggcgt ctggctctgg | 240 |
| actgtgatct gccaggatga aaatctttac attcgtggca agcgtcagtt cttttaagttt | 300 |
| gccaagaaga ttccagccgt gcgtcgtcag gtggagactg aattggccaa ggccaaaaac | 360 |
| gacttcgaga cggaaatcaa aaagagcaac gcccacctta cctactcgga aactctgccc | 420 |
| gagaagggac tcagcaagga ggagatcctc cgactggtgg atgagcacct gaagactggt | 480 |
| cactacaact ggcgtgatgg tcgtgtatct ggcgcggtct acggctacaa gcctgatctg | 540 |
| gtggagctcg tcactgaagt gtacggcaag gcctcctaca ccaatccctt gcacgcagat | 600 |
| cttttcccgg gagtttgcaa aatggaggcg gaggtagtgc gcatggcatg caacctgttc | 660 |
| catggaaact cagccagctg tggaaccatg accaccggcg gcaccgaatc cattgtaatg | 720 |
| gccatgaagg cgtacaggga tttcgctaga gagtacaagg gaatcaccag gccaaacatc | 780 |
| gtggtgccta agacggtcca cgcggccttc gacaagggtg gtcagtactt aatatccac | 840 |
| gtgcgatccg tggatgtaga tccggagacc tacgaagtgg acattaagaa gttcaaacgt | 900 |
| gccattaata ggaacacgat tctgctggtt gggtctgctc caaacttccc ctatggaacc | 960 |
| atagatgata tcgaagctat cgccgctttg gcgttaagt acgacattcc cgtgcacgtg | 1020 |
| gacgcctgcc tgggcagctt tgtggtggcc ttggtccgca acgccggcta agctgcgt | 1080 |
| cccttcgact tgaggtcaa gggagtgacc agtatctccg ctgatacca caagtatggt | 1140 |
| ttcgcgccca aggatcatc ggtgatcctt tactcggaca agaagtacaa ggaccatcag | 1200 |

```
ttcactgtga ctactgactg gcctggcggc gtgtatggtt ctcccacagt caacggttcc    1260
cgtgccggag gtattatcgc cgcctgctgg gctaccatga tgagctttgg ctatgatggt    1320
tatctggaag ccactaagcg cattgtggat acggcgcgct atatcgagag ggcgttcgc     1380 gacatcgatg gcatctttat cttttggcaag ccagctactt cagtgattgc cctgggttcc   1440
aatgtgtttg acatttttccg gctatcggat tcgctgtgca aactgggctg gaacctaaat   1500
gcgctgcagt ttccatctgg tatccacctg tgcgtgacgg acatgcacac acagcccgga    1560
gtcgcggata aattcattgc cgatgtgcgc agctgtacgg cggagatcat gaaggatccc    1620
ggccagcccg tcgttggaaa gatggctctc tacggcatgg cacagagcat acccgaccgt    1680
tcggtgatcg gagaagtgac tcgcctattc ctgcactcca tgtactacac tcccagccag    1740
aaatagacac ctggagcaat ccccgttctc ttcgcccacc ccacggagct aatgcatttc    1800
ctgtgctgta tttaaaccac caaaacaccc cgtcgttaaa ccttcctcaa gcaatttata    1860
ttaggatgca attagtgctg taatcgaggg tacaaaacgt cgttctacgc gaaaatctat    1920
ctacctatgt tcatcccatt tgtcaacatt cgtcgctcta agagccatgt tattaaagtg    1980
tttttctgtg taacttgcta gtgaaataat aatataatat taatcaaaaa aaaaaaaaaa    2040
aaa                                                                 2043

<210> SEQ ID NO 27
<211> LENGTH: 2043
<212> TYPE: DNA
<213> ORGANISM: Drosophila melanogaster

<400> SEQUENCE: 27
gtcactctaa gccgcaatga gtttgtacga ttaaaagttt atgtctattc gcgttttttcg     60 aagctttccc gattcccgta gctgtcccac tgtacagctt gccacacgat gcgtccgttc    120
tccggcagcg attgccttaa gcccgtcacc gagggcatca accggcgtt cggcgccaag     180 gagccttggc aggtcgccac catcacggcc accacggtgc tgggaggcgt ctggctctgg    240
actgtgatct gccaggatga aaatctttac attcgtggca agcgtcagtt ctttaagttt    300
gccaagaaga ttccagccgt gcgtcgtcag gtggagactg aattggccaa ggccaaaaac    360
gacttcgaga cggaaatcaa aaagagcaac gcccaccta cctactcgga aactctgccc      420
gagaagggac tcagcaagga ggagatcctc cgactggtgg atgagcacct gaagactggt    480
cactacaact ggcgtgatgg tcgtgtatct ggcgcggtct acggctacaa gcctgatctg    540
gtggagctcg tcactgaagt gtacggcaag gcctcctaca ccaatcccct tgcacgcagat    600 cttttcccgg gagtttgcaa aatgaggcg gaggtagtgc gcatggcatg caacctgttc     660
catgaaaact cagccagctg tggaaccatg accaccggcg gcaccgaatc cattgtaatg    720
gccatgaagg cgtacaggga tttcgctaga gagtacaagg gaatcaccag gccaaacatc    780
gtggtgccta agacggtcca cgcggccttc gacaaggtg tcagtacttt aatatccac      840 gtgcgatccg tggatgtaga tccggagacc tacgaagtgg acattaagaa gttcaaacgt    900
gccattaata ggaacacgat tctgctggtt gggtctgctc caaacttccc ctatggaacc    960
atagatgata tcgaagctat cgccgctttg ggcgttaagt acgacattcc cgtgcacgtg   1020
gacgcctgcc tggcagcttt tgtggtggcc ttggtccgca acgccggcta taagctgcgt    1080
cccttcgact ttgaggtcaa gggagtgacc agtatctccg ctgatacca caagtatggt    1140 ttcgcgccca gggatcatc ggtgatcctt tactcggaca agaagtacaa ggaccatcag    1200
ttcactgtga ctactgactg gcctggcggc gtgtatggtt ctcccacagt caacggttcc    1260
```

-continued

```
cgtgccggag gtattatcgc cgcctgctgg gctaccatga tgagctttgg ctatgatggt    1320
tatctggaag ccactaagcg cattgtggat acggcgcgct atatcgagag gggcgttcgc    1380
gacatcgatg gcatctttat ctttggcaag ccagctactt cagtgattgc cctgggttcc    1440
aatgtgtttg acattttccg gctatcggat tcgctgtgca aactgggctg aacctaaat    1500 gcgctgcagt ttccatctgg tatccacctg tgcgtgacgg acatgcacac acagcccgga    1560
gtcgcggata aattcattgc cgatgtgcgc agctgtacgg cggagatcat gaaggatccc    1620
ggccagcccg tcgttggaaa gatggctctc tacggcatgg cacagagcat acccgaccgt    1680
tcggtgatcg gagaagtgac tcgcctattc ctgcactcca tgtactacac tcccagccag    1740
aaatagacac ctggagcaat ccccgttctc ttcgcccacc ccacggagct aatgcatttc    1800
ctgtgctgta tttaaaccac caaaacaccc cgtcgttaaa ccttcctcaa gcaatttata    1860
ttaggatgca attagtgctg taatcgaggg tacaaaacgt cgttctacgc gaaaatctat    1920
ctacctatgt tcatcccatt tgtcaacatt cgtcgctcta agagccatgt tattaaagtg    1980
tttttctgtg taacttgcta gtgaaataat aatataatat taatcaaaaa aaaaaaaaaa    2040
aaa                                                                  2043
```

<210> SEQ ID NO 28
<211> LENGTH: 641
<212> TYPE: PRT
<213> ORGANISM: Drosophlia melanogaster

<400> SEQUENCE: 28

```
Met Thr Ala Asn Thr Gly Thr Ser Gly Glu Asn Leu Met Gly Asn Gly
  1               5                  10                  15

Gly Lys Thr His Glu Pro Ser Thr Pro Thr Ser Asp Thr Glu Val Ala
             20                  25                  30

Ser Gly Thr Pro Thr Glu Leu Ser Glu Ile Phe Phe Val Asp Asn Ser
         35                  40                  45

Arg Arg Lys Gln Ser Ile Lys Ile Gln Val Lys Leu Cys Pro Glu Gly
     50                  55                  60

Val Tyr Leu Arg Arg Glu Thr Glu Glu Asp Asp His Ile Asn Glu Gln
 65                  70                  75                  80

Leu Ile Arg Ile Asp Asp Ile Ile Gly Ser Arg Tyr Gly Arg Arg Leu
                 85                  90                  95

Lys Lys Arg Ala Arg Gly Gly Leu Asn Ser Cys Arg Asn Pro Asn Val
            100                 105                 110

Pro Gly Gln Glu Ala Asp Ser Glu Pro Asp Ser Asp Asn Ser Ala Tyr
        115                 120                 125

Leu Tyr Ile Tyr Ala Tyr Leu Lys Lys Glu Lys Pro Leu Arg Arg Val
    130                 135                 140

Gln Thr Leu Arg Ile Leu Arg Phe Arg Ser Ser Asn Asp Tyr Gly Val
145                 150                 155                 160

Asn Leu Gln Thr Ala Glu Met Trp His His Thr Ile Arg Lys His Lys
                165                 170                 175

Arg Gly Asn Gly Ser Ser Ser Pro Ala Asp Cys Gly Lys Gln Leu Leu
            180                 185                 190

Ile Leu Leu Asn Pro Lys Ser Gly Ser Gly Lys Gly Arg Glu Leu Phe
        195                 200                 205

Gln Lys Gln Val Ala Pro Leu Leu Thr Glu Ala Glu Val Gln Tyr Asp
    210                 215                 220
```

```
Leu Gln Ile Thr Thr His Pro Gln Tyr Ala Lys Glu Phe Val Arg Thr
225                 230                 235                 240

Arg Arg Asp Leu Leu Thr Arg Tyr Ser Gly Ile Val Val Ala Ser Gly
            245                 250                 255

Asp Gly Leu Phe Tyr Glu Val Leu Asn Gly Leu Met Glu Arg Met Asp
                260                 265                 270

Trp Arg Arg Ala Cys Arg Glu Leu Pro Leu Gly Ile Ile Pro Cys Gly
        275                 280                 285

Ser Gly Asn Gly Leu Ala Lys Ser Val Ala His His Cys Asn Glu Pro
290                 295                 300

Tyr Glu Pro Lys Pro Ile Leu His Ala Thr Leu Thr Cys Met Ala Gly
305                 310                 315                 320

Lys Ser Thr Pro Met Asp Val Val Arg Val Glu Leu Ala Thr Arg Asp
                325                 330                 335

Lys His Phe Val Met Tyr Ser Phe Leu Ser Val Gly Trp Gly Leu Ile
                340                 345                 350

Ala Asp Ile Asp Ile Glu Ser Glu Arg Leu Arg Ser Ile Gly Ala Gln
            355                 360                 365

Arg Phe Thr Leu Trp Ala Ile Lys Arg Leu Ile Gly Leu Arg Ser Tyr
        370                 375                 380

Lys Gly Arg Val Ser Tyr Leu Leu Gly Lys Gly Lys Lys Glu Pro Pro
385                 390                 395                 400

Val Glu Ala Ala Arg Glu Leu Pro Ala Glu Ser Thr Ala Ala Gly Ile
                405                 410                 415

Arg Ser Ser Leu Pro Leu Asn Ala Gly Glu Phe His Asp Leu Pro Glu
            420                 425                 430

Glu Glu Glu Gly Glu Ala Val Leu Asp Gly Gln Phe Ala Asp Ala
        435                 440                 445

Ile Ser Leu Asp Arg Ser Val Tyr Arg Gln His Ala Asp Ser Trp His
450                 455                 460

Ser Ala Met Ser Arg Arg Thr Ala Tyr Tyr Ser Leu Gly Gly Pro Ser
465                 470                 475                 480

Met Arg Ser Asn Arg Ser Arg Met Ser Ile Ser Gln Arg Ile Glu Ala
                485                 490                 495

Ala Asn Ala Glu Phe Ala Glu Arg Val Pro Thr Gly Thr Ile Pro Pro
                500                 505                 510

Leu Gln Met Pro Leu Leu Ser Ser Asp Gly Trp Ile Cys Glu Asp Gly
            515                 520                 525

Asp Phe Val Met Val His Ala Ala Tyr Thr Thr His Leu Ser Ser Asp
        530                 535                 540

Val Phe Phe Ala Pro Glu Ser Arg Leu Asp Asp Gly Leu Ile Tyr Leu
545                 550                 555                 560

Val Ile Ile Arg Arg Gly Val Ser Arg His Gln Leu Leu Asn Phe Met
                565                 570                 575

Leu Asn Leu Asn Ala Gly Thr His Leu Pro Ile Gly Glu Asp Pro Phe
            580                 585                 590

Ile Lys Val Val Pro Cys Arg Ala Phe Arg Ile Glu Pro Ser Ser Ser
        595                 600                 605

Asp Gly Ile Leu Val Val Asp Gly Glu Arg Val Glu Tyr Gly Pro Ile
610                 615                 620

Gln Ala Glu Val Met Pro Gly Leu Ile Asn Val Met Thr Thr Ser Gly
625                 630                 635                 640

Gln
```

<210> SEQ ID NO 29
<211> LENGTH: 907
<212> TYPE: PRT
<213> ORGANISM: Drosophila melanogaster

<400> SEQUENCE: 29

```
Met Ser Glu Ser Leu Asp Lys Thr Thr Ser Pro Ser Ala Ser Ser
 1               5                  10                  15

Arg Ala Thr Pro Pro Gly Thr Gln Asp Ala Asp Glu Gly His Asp Val
             20                  25                  30

Ser Asp Thr Phe Tyr Thr Ser Gln Arg Lys Lys Gly Ser His Val Phe
             35                  40                  45

Arg Val Arg Leu Asp Ala Thr Gly Phe Thr Leu Gln Arg Glu Ser Pro
 50                  55                  60

Gly Gly Ser Ile Val Lys Glu Gln His Val Arg Ile Ser Asp Ile Val
 65                  70                  75                  80

Gly Ala Arg Cys Met Arg Pro Lys Lys Ser Arg Arg Leu Ala Met Ser
                 85                  90                  95

Gly Ala Cys Ala Cys Ser Ser Gly Asn Pro Asn Ser Pro Ala Ile Ser
                100                 105                 110

Ala Ser Gly Asp His His Arg Pro Ala Thr Thr Pro Ser Lys Cys Ser
            115                 120                 125

Thr Asn Ser Arg Asp Asn Ile Pro Ser Asp Gly Gly Asp Val Ser Ala
130                 135                 140

Phe Leu Tyr Val Phe Ala Tyr Val Leu Lys Lys Arg Ser Leu Arg Ser
145                 150                 155                 160

Glu Leu His Arg Glu Arg Thr Val Leu Thr Leu Arg Phe Arg Ser Phe
                165                 170                 175

Asp Thr Phe Glu Asp Asn Met Arg Glu Ala Asp Arg Trp Tyr Arg Ser
            180                 185                 190

Leu Arg Trp Gln Leu His Arg Thr Leu Glu Glu Ile Phe Val Ala Pro
        195                 200                 205

Thr Val Asp Glu Arg Arg Arg Val Leu Val Leu Leu Asn Pro Lys
    210                 215                 220

Ser Gly Ser Gly Asp Ala Arg Glu Val Phe Asn Met His Val Thr Pro
225                 230                 235                 240

Val Leu Asn Glu Ala Glu Val Pro Tyr Asp Leu Tyr Val Thr Lys His
                245                 250                 255

Ser Asn Phe Ala Ile Glu Phe Leu Ser Thr Arg Cys Leu Asp Ala Trp
            260                 265                 270

Cys Cys Val Val Ala Val Gly Gly Asp Gly Leu Phe His Glu Ile Val
        275                 280                 285

Asn Gly Leu Leu Gln Arg Gln Asp Trp Ala His Val Leu Pro His Leu
    290                 295                 300

Ala Leu Gly Ile Ile Pro Cys Gly Ser Gly Asn Gly Leu Ala Arg Ser
305                 310                 315                 320

Ile Ala His Cys Tyr Asn Lys Pro Val Leu Gly Ala Ala Leu Thr Val
                325                 330                 335

Ile Ser Gly Arg Ser Ser Pro Met Asp Val Val Arg Val Gln Leu Gln
            340                 345                 350

Ser Arg Ser Leu Tyr Ser Phe Leu Ser Ile Gly Trp Gly Leu Ile Ser
        355                 360                 365

Asp Val Asp Ile Glu Ser Glu Arg Ile Arg Met Leu Gly Tyr Gln Arg
    370                 375                 380
```

-continued

```
Phe Thr Val Trp Thr Leu Tyr Arg Leu Val Asn Leu Arg Thr Tyr Asn
385                 390                 395                 400

Gly Arg Ile Ser Tyr Leu Leu Thr Asp His Glu Val Ser Ser Thr His
            405                 410                 415

Ser Ala Thr Gly Tyr Ala Ala Gln Arg Met Gln Ser Ser Arg Ser
        420                 425                 430

Cys Asn Thr His Ile Asp Met Leu Asn Gly Pro Ala Pro Ile Tyr His
        435                 440                 445

Ser Ser Ala Glu Tyr Leu Pro Gln Glu Phe Ala Asp Val Ile Ser Leu
    450                 455                 460

Glu Thr Ser Ile Asn Gln Ser Phe Arg Ser Arg Cys Asp Ser Trp Leu
465                 470                 475                 480

Ser Gly Gly Ser Arg Arg Ser Phe Tyr Tyr Ser Ile Ser Glu Ser Ile
            485                 490                 495

Tyr His Ser Leu Ala Asp Glu Ser Glu Phe Ala Gly Leu Ala Ala Ala
            500                 505                 510

Ser Leu Glu Asn Arg Gln Gln Asn Tyr Gly Pro Ala Ser Glu Leu Pro
    515                 520                 525

Asp Leu Asn Glu Pro Leu Ser Glu Asp Gln Gly Trp Leu Val Glu Glu
    530                 535                 540

Gly Glu Phe Val Met Met His Ala Val Tyr Gln Thr His Leu Gly Ile
545                 550                 555                 560

Asp Cys His Phe Ala Pro Lys Ala Gln Leu Asn Asp Gly Thr Ile Tyr
            565                 570                 575

Leu Ile Leu Ile Arg Ala Gly Ile Ser Arg Pro His Leu Leu Ser Phe
            580                 585                 590

Leu Tyr Asn Met Ser Ser Gly Thr His Leu Pro Glu Ser His Asp Asp
            595                 600                 605

His Val Lys Val Leu Pro Val Arg Ala Phe Arg Leu Glu Pro Tyr Asp
            610                 615                 620

Asn His Gly Ile Ile Thr Val Asp Gly Glu Arg Val Glu Phe Gly Pro
625                 630                 635                 640

Leu Gln Ala Glu Val Leu Pro Gly Ile Ala Arg Val Met Val Pro Asn
                645                 650                 655

Val Ser Thr Phe Arg Phe Gln Ser Ala Thr Leu Gln His Gly Ile Pro
            660                 665                 670

Val Cys Ile Pro Val Arg Lys Arg Phe Val Leu Tyr Asn Met Ser Ser
            675                 680                 685

Glu Glu Leu Ala Pro Ile Asn Glu Gln Asp Phe Lys Asp Leu Lys Glu
            690                 695                 700

Arg Met Lys Leu Ile Val Glu Ala Asp Pro Lys Gln Tyr His Asn Asp
705                 710                 715                 720

Phe Ser Leu Arg Arg Tyr Leu Arg Ala Phe Lys Thr Thr Asp Asp Ala
                725                 730                 735

Phe Gln Ala Ile Leu Lys Thr Asn Lys Trp Arg Glu Thr Tyr Gly Val
            740                 745                 750

Asp Lys Leu Ser Glu Met Asp Arg Ser Gln Leu Asp Lys Lys Ala Arg
            755                 760                 765

Leu Leu Arg His Arg Asp Cys Ile Gly Arg Pro Val Ile Tyr Ile Pro
    770                 775                 780

Ala Lys Asn His Ser Ser Glu Arg Asp Ile Asp Glu Leu Thr Arg Phe
785                 790                 795                 800
```

```
Ile Val Tyr Asn Leu Glu Glu Ala Cys Lys Lys Cys Phe Glu Glu Val
                805                 810                 815

Thr Asp Arg Leu Cys Ile Val Phe Asp Leu Ala Glu Phe Ser Thr Ser
            820                 825                 830

Cys Met Asp Tyr Gln Leu Val Gln Asn Leu Ile Trp Leu Leu Gly Lys
        835                 840                 845

His Phe Pro Glu Arg Leu Gly Val Cys Leu Ile Ile Asn Ser Pro Gly
    850                 855                 860

Leu Phe Ser Thr Ile Trp Pro Ala Ile Arg Val Leu Leu Asp Asp Asn
865                 870                 875                 880

Thr Ala Lys Lys Val Lys Phe Val Ala Asp Glu Ala Glu Leu Cys Gln
                885                 890                 895

Tyr Leu Ile Pro Asp Ile Leu Pro Thr Asp Met
            900                 905
```

COMPOSITIONS AND METHODS FOR THE MODULATION OF SPHINGOLIPID METABOLISM AND/OR SIGNALING

CROSS REFERENCE TO RELATED APPLICATIONS

This application claims the benefit of provisional application No. 60/349,582, filed Jan. 17, 2002 and U.S. application Ser. No. 10/053,510, filed Jan. 17, 2002, both applications incorporated herein by reference in their entirety.

STATEMENT REGARDING FEDERALLY SPONSORED RESEARCH OR DEVELOPMENT

This invention was made with government support under Grant No. 1R01CA77528 awarded by the National Institutes of Health. The government has certain rights in this invention.

BACKGROUND OF THE INVENTION

1. Field of the Invention

The present invention relates generally to cancer detection and therapy. The invention is more particularly related to polynucleotides encoding polypeptides involved in the metabolism of sphingolipids, polypeptides, and to agents that modulate the expression and/or activity of such polypeptides. Such agents may be used, for example, to diagnose and/or treat cancers such as breast, colon, uterus, stomach, ovary, lung, kidney and rectum cancer, the diagnosis and treatment of muscle developmental defects and cardiomyopathy, and diagnosis and treatment of hereditary sensory neuropathy type 1 and the sphingolipidoses. The present invention further relates to methods of screening agents that modulate the expression and/or activity of polynucleotides and/or polypeptides involved in sphingolipid metabolism.

2. Description of the Related Art

Breast cancer is a significant health problem for women in the United States and throughout the world. Although advances have been made in detection and treatment of the disease, breast cancer remains the most common form of cancer, and the second leading cause of cancer death, in American women. Among African-American women and women between 15 and 54 years of age, breast cancer is the leading cause of cancer death. One out of every eight women in the United States will develop breast cancer, a risk which has increased 52% during 1950-1990. In 1994, it is estimated that 182,000 new cases of female breast cancer were diagnosed, and 46,000 women died from the disease.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. However, the use of established markers often leads to a result that is difficult to interpret.

With current therapies, tumor invasiveness and metastasis is a critical determinant in the outcome for breast cancer patients. Although the five year survival for women diagnosed with localized breast cancer is about 90%, the five year survival drops to 18% for women whose disease has metastasized. Present therapies are inadequate for inhibiting tumor invasiveness for the large population of women with this severe disease.

Colon cancer is the second most frequently diagnosed malignancy in the United States as well as the second most common cause of cancer death. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat. In spite of considerable research into therapies for these and other cancers, colon cancer remains difficult to diagnose and treat effectively. Accordingly, improvements are needed in the treatment, diagnosis and prevention of breast and colon cancer. The present invention fulfills this need and further provides other related advantages.

Mutations that result in failure or dysregulation of sphingolipid synthesis or catabolism are directly responsible for a number of human diseases, including hereditary sensory neuropathy type 1 and the group of lysosomal storage diseases called the sphingolipidoses (Bejaoui, K., Wu, C., Scheffler, M. D., Haan, G., Ashby, P., Wu, L., de Jong, P. and Brown, R. H., Jr. (2001). *Nat Genet* 27, 261-2.; Dawkins, J. L., Hulme, D. J., Brahmbhatt, S. B., Auer-Grumbach, M. and Nicholson, G. A. (2001). *Nat Genet* 27, 309-12.; Gable, K., Han, G., Monaghan, E., Bacikova, D., Natarajan, M., Williams, R. and Dunn, T. M. (2002). *J Biol Chem* 277, 10194-200.). A large body of evidence now indicates that sphingolipid metabolites and enzymes of sphingolipid metabolism play important roles in regulating cell migration, stress response, survival, differentiation, senescence, apoptosis, receptor signaling, and endocytosis in eukaryotic cells. These findings suggest molecular mechanisms by which sphingolipids may affect animal physiology and contribute to disease states.

Sphingosine-1-phosphate (S-1-P) is an endogenous sphingolipid metabolite present in most mammalian cells and in serum. Like other sphingolipid metabolites such as ceramide and sphingosine, S-1-P participates in specific signal transduction pathways. Many of the effects of S-1-P signaling, which include promotion of cellular proliferation, enhancement of migration, inhibition of apoptosis and stimulation of angiogenesis, influence the transformation, growth, drug resistance, vascularity and metastatic capacity of cancer cells. Several observations support the notion that sphingosine kinase (SK) and sphingosine-1-phosphate lyase (SPL) may be cancer related genes. First, the overexpression of SK in NIH3T3 fibroblasts leads to oncogenic transformation as determined by the ability of transfected cells to form foci in vitro and to form fibrosarcomas in NOD/SCID mice. Second, human SPL was cloned and mapped to 10q21, a chromosomal region frequently deleted in a variety of human cancers. Taken together, these observations raise the possibility that SK and SPL may be potentially effective targets for pharmacological intervention in the treatment of cancer. Accordingly, the present invention provides methods for screening agents that modulate sphingolipid metabolism. Further, the present invention provides methods for detecting and treating cancer.

Critical steps in the identification and development of new therapeutic agents are: (a) generation of candidate agents; and (b) screening of the candidate agents for efficacy and safety. With the advent of combinatorial chemistry protocols, large numbers of potential compounds, known as libraries, can be rapidly generated. Such libraries serve as collections of potential therapeutic agents. Following generation of a library of potential therapeutic agents, the library must be screened to identity the promising candidates.

For screening purposes, a number of in vitro high throughput screening protocols have been developed. However, these in vitro screening assays must be followed by in vivo screening assays. Since it is undesirable to immediately screen compounds that show promise from in vitro assays in humans, an important step in the identification of therapeutic agents for such cellular proliferative diseases is the screening of potential therapeutic compounds in non-human animal models. As such, non-human animal models of cancer and other cellular proliferative diseases play an important role in the discovery of therapeutic agents for such diseases.

One type of non-human animal model that can be used for screening purposes to identify therapeutic agents for use in treating cancer and other cellular proliferative diseases is a non-human mammalian model, e.g. mice, etc. However, mice are expensive, have a slow reproduction time, and generate small numbers of offspring. As such, they are less than ideal for many high throughput screening assays.

Accordingly, there is a need for additional animal models for the identification of therapeutic agents for cancer and other diseases associated with altered sphingolipid metabolism, such as. Of particular interest would be the development of an animal model having a relatively short life span and a rapid reproduction cycle characterized by the production of large numbers of offspring. Preferably, such an animal model should also be relatively simple and economic to maintain.

BRIEF SUMMARY OF THE INVENTION

As noted above, the present invention relates generally to cancer detection and therapy. The invention is more particularly related to polynucleotides encoding polypeptides involved in the metabolism and/or signaling of sphingolipids, polypeptides, and to agents that modulate the expression and/or activity of such polypeptides and/or the alter the levels of sphingolipid intermediates. Such agents may be used, for example, to diagnose and/or treat cancers such as breast, colon, uterus, stomach, ovary, lung, kidney and rectum cancer, the diagnosis and treatment of muscle developmental defects and cardiomyopathy, and diagnosis and treatment of hereditary sensory neuropathy type 1 and the sphingolipidoses. The present invention further relates to methods of screening agents that modulate the components and intermediates involved in sphingolipid metabolism and/or signaling.

It is an aspect of the present invention to provide a method for identifying an agent that modulates sphingolipid metabolism, comprising (a) culturing a homozygous null mutant *Drosophila melanogaster* in the absence and presence of a candidate agent under conditions and for a time sufficient to observe in the mutant *Drosophila melanogaster* an effect of the agent on a level of either (i) at least one sphingolipid intermediate, or (ii) activity of at least one component of a sphingolipid pathway, wherein the mutant *Drosophila melanogaster* comprises a P-element transposon insertion in a gene encoding a component of a sphingolipid pathway that results in at least one of an altered level of at least one sphingolipid intermediate and an altered activity level of at least one sphingolipid pathway component; and (b) comparing the level of either (i) the sphingolipid intermediate that is generated, or (ii) the activity of the sphingolipid pathway component, in the presence of the candidate agent to the level in the absence of the candidate agent, wherein an altered level indicates the agent modulates sphingolipid metabolism. In certain embodiments the altered level of a sphingolipid intermediate comprises an increase in $C_{14/16}$ long chain bases, and in certain other embodiments the altered level of a sphingolipid intermediate comprises an increase in $C_{14/16}$ phosphorylated long chain bases. In certain embodiments the gene encoding a component of a sphingolipid pathway comprises a polynucleotide sequence set forth in any one of SEQ ID NOS:15, 24 and 25. In certain embodiments the homozygous null mutant *Drosophila melanogaster* exhibits a flightless phenotype, and in certain other embodiments the homozygous null mutant *Drosophila melanogaster* comprises a tumor. In certain embodiments the homozygous null mutant *Drosophila melanogaster* comprises a T2 segment which comprises abnormal developmental patterning of thoracic muscles. In certain embodiments the altered level of the sphingolipid intermediate that is generated in the presence of the candidate agent comprises a decrease in sphingosine-1-phosphate and in certain embodiments the altered level of the sphingolipid intermediate that is generated in the presence of the candidate agent comprises an increase in sphingosine-1-phosphate.

In still other embodiments the altered level of the activity of the sphingolipid pathway component in the presence of the candidate agent comprises a decrease in sphingosine-1-phosphate lyase (SPL) activity, while in other embodiments the altered level of the activity of the sphingolipid pathway component in the presence of the candidate agent comprises an increase in sphingosine-1-phosphate lyase (SPL) activity. In still other embodiments the altered level of the activity of the sphingolipid pathway component in the presence of the candidate agent comprises a decrease in sphingosine kinase (SK) activity, while in other embodiments the altered level of the activity of the sphingolipid pathway component in the presence of the candidate agent comprises an increase in sphingosine kinase (SK) activity. In certain embodiments the agent inhibits SK activity, and in certain other embodiments the agent inhibits SPL activity. In certain embodiments the agent comprises a 1-aryl-2-dimethylaminopropane-1,3-diol derivative, and in certain other embodiments the derivative comprises a substitution of a fatty acid amide group. In certain further embodiments the substitution comprises two N-methyl groups. In another embodiment the agent increases activity of serine palmitoyltransferase.

Turning to another aspect, the present invention provides a method for identifying an agent that modulates sphingolipid metabolism, comprising (a) culturing a homozygous null mutant *Drosophila melanogaster* in the absence and presence of a candidate agent under conditions and for a time sufficient to observe in said mutant *Drosophila melanogaster* an effect of the agent on a level of either (i) at least one sphingolipid intermediate, or (ii) activity of at least one component of a sphingolipid pathway, wherein the mutant *Drosophila melanogaster* comprises a P-element transposon insertion in a gene encoding a component of a sphingolipid pathway that results in an altered activity level of at least one sphingolipid pathway component, and wherein the mutant *Drosophila melanogaster* exhibits a flightless phenotype that results from said insertion; and (b) comparing flight performance of the mutant *Drosophila* that is cultured in the presence of the candidate agent to the flight performance of the mutant *Drosophila* that is cultured in the absence of the candidate agent, wherein an increased flight performance of the mutant *Drosophila* cultured in the presence of the agent indicates the agent modulates sphingolipid metabolism. In certain embodiments the mutant *Drosophila melanogaster* comprises a homozygous mutation in a gene encoding a sphingosine-1-phosphate lyase (SPL), and in certain embodiments the homozygous null mutant *Drosophila melanogaster* comprises a T2 segment which comprises abnormal developmental patterning of thoracic muscles. In certain embodiments the agent that modulates sphingolipid metabolism inhibits sphingosine kinase activity.

In yet another embodiment there is provided a method for identifying an agent that modulates sphingolipid signaling, comprising (a) culturing a homozygous null mutant *Drosophila melanogaster* in the absence and presence of a candidate agent under conditions and for a time sufficient to observe in said mutant *Drosophila melanogaster* an effect of the agent on a level of at least one sphingolipid intermediate, wherein the mutant *Drosophila melanogaster* comprises a P-element transposon insertion in a gene encoding a component of a sphingolipid pathway that results in an altered level of at least one sphingolipid intermediate; and (b) comparing the level of the sphingolipid intermediate that is generated in the presence of the candidate agent to the level in the absence of the candidate agent, wherein an altered level indicates the agent modulates sphingolipid signaling. It is also an aspect of the invention to provide an agent identified by the method of any one of the above described methods, which in certain embodiments is a composition comprising such agent in combination with a physiologically acceptable excipient. In certain embodiments there is provided a composition comprising an agent that increases flight performance in a homozygous null mutant *Drosophila melanogaster*, wherein the mutant *Drosophila melanogaster* comprises a P-element transposon insertion in a gene encoding a sphingosine-1-phosphate lyase (SPL) polypeptide that comprises the amino acid sequence set forth in SEQ ID NO:16, and wherein the mutant *Drosophila melanogaster* exhibits a flightless phenotype that results from said insertion, and in certain further embodiments the agent inhibits sphingosine kinase activity.

According to certain other embodiments of the present invention there is provided a method for preparing a sphingosine-1-phosphate lyase (SPL) polypeptide, comprising culturing a host cell transformed or transfected with a nucleic acid construct comprising a promoter operably linked to a polynucleotide comprising the nucleotide sequence set forth in SEQ ID NO:15; and recovering a sphingosine-1-phosphate lyase polypeptide.

In still other embodiments there is provided a method for identifying an agent that modulates sphingosine-1-phosphate lyase activity, comprising (a) contacting a candidate agent with an isolated polypeptide that comprises an amino acid sequence selected from an amino acid sequence set forth in SEQ ID NO:16 and an amino acid sequence having at least 90% identity to the sequence set forth in SEQ ID NO:16, wherein the polypeptide has sphingosine-1-phosphate lyase activity, and wherein the step of contacting is carried out under conditions and for a time sufficient to allow the candidate agent to interact with said polypeptide; and (b) determining degradation by the polypeptide of sphingosine-1-phosphate or a sphingosine-1-phosphate derivative thereof in the presence of the candidate agent, relative to degradation by said polypeptide of sphingosine-1-phosphate or a sphingosine-1-phosphate derivative thereof in the absence of the candidate agent, and therefrom identifying an agent that modulates sphingosine-1-phosphate lyase activity.

In another embodiment there is provided a method for identifying an agent that modulates sphingosine-1-phosphate lyase activity, comprising (a) contacting a candidate agent with a biological sample that comprises a cell which expresses a polypeptide that comprises an amino acid sequence selected from an amino acid sequence set forth in SEQ ID NO:16 and an amino acid sequence having at least 90% identity to the sequence set forth in SEQ ID NO:16, wherein said polypeptide has sphingosine-1-phosphate lyase activity, and wherein the step of contacting is carried out under conditions and for a time sufficient to allow the candidate agent to interact with the polypeptide; and (b) determining degradation by said polypeptide of sphingosine-1-phosphate or a sphingosine-1-phosphate derivative thereof in the presence of the candidate agent, relative to degradation by said polypeptide of sphingosine-1-phosphate or a sphingosine-1-phosphate derivative thereof in the absence of the candidate agent, and therefrom identifying an agent that modulates sphingosine-1-phosphate lyase activity. In certain embodiments the step of determining comprises an in vitro assay of an extract from the cell.

In certain embodiments the invention provides a composition comprising an agent that modulates sphingosine-1-phosphate lyase activity of a polypeptide, said polypeptide comprising a sequence set forth in SEQ ID NO:16, in combination with a pharmaceutically acceptable carrier. In certain further embodiments the agent comprises a polynucleotide. In certain other further embodiments the agent comprises an antibody or an antigen-binding fragment thereof that specifically binds a sphingosine phosphate lyase (SPL) polypeptide comprising the sequence set forth in SEQ ID NO:16, and wherein the antibody increases the ability of the SPL polypeptide to degrade sphingosine-1-phosphate. In certain embodiments the invention provides a method for inhibiting growth of a cancer cell, comprising contacting the cancer cell with an agent that increases sphingosine-1-phosphate lyase activity of a polypeptide comprising a sequence set forth in SEQ ID NO:16. In certain further embodiments the agent increases expression of an endogenous sphingosine-1-phosphate lyase gene, and in certain other further embodiments the cancer cell is a breast cancer cell.

According to another embodiment there is provided a method for inhibiting development of cancer, metastasis, or both development of cancer and metastasis in a mammal, comprising administering to said mammal an agent that increases sphingosine-1-phosphate lyase activity of a polypeptide comprising a sequence set forth in SEQ ID NO:16. In certain further embodiments the agent increases expression of an endogenous sphingosine-1-phosphate lyase gene, and in certain still further embodiments the agent is linked to a targeting component, which in certain still further embodiments is an anti-tumor antibody and in certain other still further embodiments binds to an estrogen receptor. In certain embodiments the mammal is afflicted with breast cancer.

It is another aspect of the present invention to provide a method for determining the presence of cancer in a patient, comprising the steps of (a) contacting a first biological sample comprising at least one polynucleotide and being obtained from a patient suspected of having cancer with at least one oligonucleotide that is specific for a polynucleotide which comprises a nucleic acid sequence as set forth in SEQ ID NO:23; (b) detecting an amount of the olignucleotide that hybridizes to the polynucleotide in the first sample; and (d) comparing the amount of oligonucleotide that hybridizes to the polynucleotide in the first sample to an amount of oligonucleotide that hybridizes to a polynucleotide in a second biological sample obtained from a normal control subject known to be free of cancer, wherein a statistically significant decrease in the amount of olignucleotide that hybridizes to the polynucleotide in the first biological sample relative to the amount of oligonucleotide that hybridizes to the polynucleotide in the second sample signifies the presence of a cancer in said patient.

It is another aspect of the present invention to provide a method for diagnosing a disease associated with altered sphingolipid metabolism comprising (a) contacting a first biological sample comprising at least one polynucleotide and being obtained from a patient suspected of having a disease associated with altered sphingolipid metabolism with at least one oligonucleotide that is specific for a polynucleotide which comprises a nucleic acid sequence as set forth in SEQ ID NO:23; (b) detecting an amount of the olignucleotide that hybridizes to the polynucleotide in the first sample; and (d) comparing the amount of oligonucleotide that hybridizes to the polynucleotide in the first sample to an amount of oligonucleotide that hybridizes to a polynucleotide in a second biological sample obtained from a normal control subject known to be free of a disease associated with altered sphingolipid metabolism, wherein a statistically significant decrease in the amount of olignucleotide that hybridizes to the polynucleotide in the first biological sample relative to the amount of oligonucleotide that hybridizes to the polynucleotide in the second sample signifies the presence of a disease associated with altered sphingolipid metabolism in said patient.

It is another aspect of the present invention to provide a method for determining the presence of a cancer in a patient, comprising the steps of (a) contacting a first biological sample comprising at least one polynucleotide and being obtained from a patient suspected of having cancer with at least one oligonucleotide that is specific for a polynucleotide which comprises a nucleic acid sequence as set forth in SEQ ID NO:22; (b) detecting an amount of the olignucleotide that hybridizes to the polynucleotide in the first sample; and (d) comparing the amount of oligonucleotide that hybridizes to the polynucleotide in the first sample to an amount of oligonucleotide that hybridizes to a polynucleotide in a second biological sample obtained from a normal control subject known to be free of cancer, wherein a statistically significant increase in the amount of olignucleotide that hybridizes to the polynucleotide in the first biological sample relative to the amount of oligonucleotide that hybridizes to the polynucleotide in the second sample signifies the presence of a cancer in said patient.

It is another aspect of the present invention to provide a method for diagnosing a disease associated with altered sphingolipid metabolism comprising (a) contacting a first biological sample comprising at least one polynucleotide and being obtained from a patient suspected of having a disease associated with altered sphingolipid metabolism with at least one oligonucleotide that is specific for a polynucleotide which comprises a nucleic acid sequence as set forth in SEQ ID NO:22; (b) detecting an amount of the olignucleotide that hybridizes to the polynucleotide in the first sample; and (d) comparing the amount of oligonucleotide that hybridizes to the polynucleotide in the first sample to an amount of oligonucleotide that hybridizes to a polynucleotide in a second biological sample obtained from a normal control subject known to be free of a disease associated with altered sphingolipid metabolism, wherein a statistically significant increase in the amount of olignucleotide that hybridizes to the polynucleotide in the first biological sample relative to the amount of oligonucleotide that hybridizes to the polynucleotide in the second sample signifies the presence of a disease associated with altered sphingolipid metabolism in said patient. It is another aspect of the present invention to provide a method for treating a disease associated with altered sphingolipid metabolism in a patient, comprising administering to said patient an agent identified according to any of the above described methods. In certain further embodiments the disease is colon cancer, breast cancer, uterine cancer, stomach cancer, ovarian cancer, lung cancer, kidney cancer, adenocarcinoma of the rectum, hereditary sensory neuropathy type 1, or any one of the sphingolipidoses.

These and other aspects of the present invention will become apparent upon reference to the following detailed description and attached drawings. All references (including websites) disclosed herein are hereby incorporated by reference in their entireties as if each was incorporated individually.

BRIEF DESCRIPTION OF THE FIGURES AND SEQUENCE IDENTIFIERS

FIG. 1 shows the amino acid sequence of 2 potential *Drosophila melanogaster* SK proteins aligned with the amino acid sequence of a human SK protein. (DSK1747 set forth in SEQ ID NO:19; DSK2159 set forth in SEQ ID NO:20).

Figure 2:
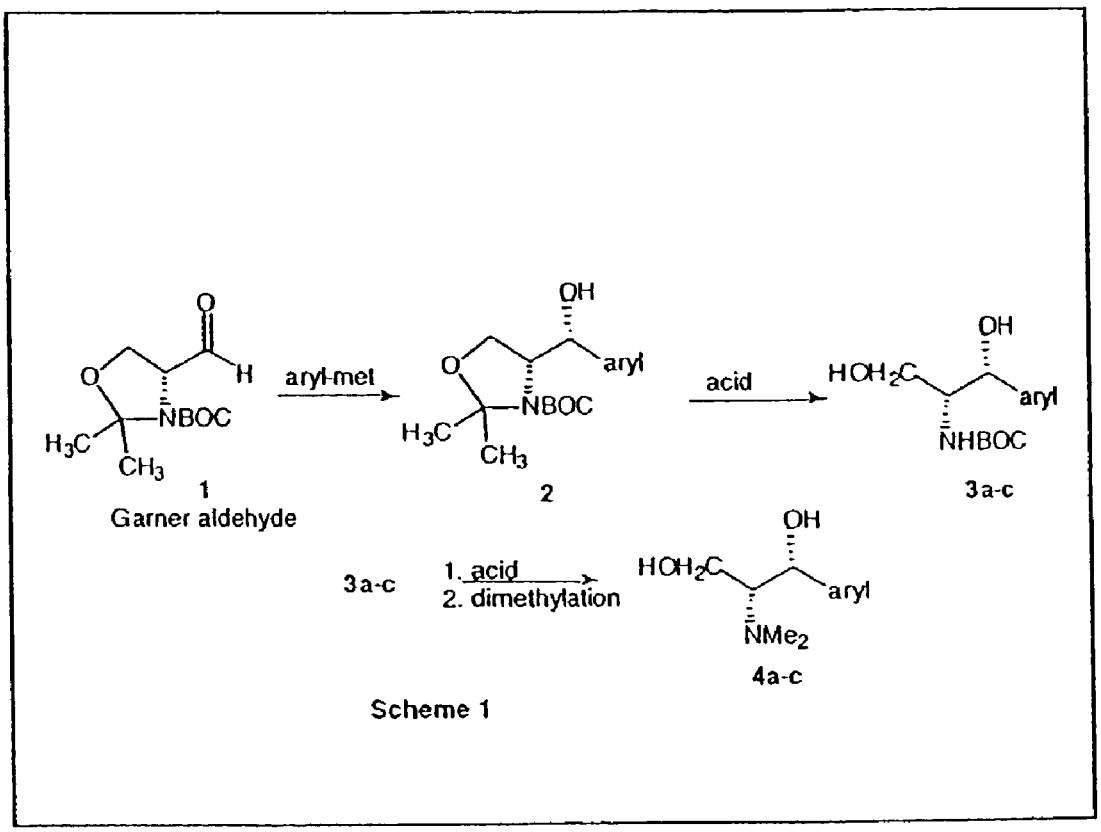
FIG. 2 shows a first chemical synthesis scheme.

SEQ ID NO:1 is the determined cDNA sequence of *S. cerevisiae* SPL

SEQ ID NO:2 is the amino acid sequence of *S. cerevisiae* SPL encoded by the polynucleotide sequence set forth in SEQ ID NO:1

SEQ ID NO:3 is the determined cDNA sequence of *C. elegans* SPL

SEQ ID NO:4 is the amino acid sequence of *C. elegans* SPL encoded by the polynucleotide sequence set forth in SEQ ID NO:3

SEQ ID NO:5 is the determined cDNA sequence of the mouse SPL

SEQ ID NO:6 is the amino acid sequence of mouse SPL encoded by the polynucleotide sequence set forth in SEQ ID NO:5

SEQ ID NO:7 is the determined cDNA sequence of the full-length human SPL

SEQ ID NO:8 is the amino acid sequence of human SPL encoded by the polynucleotide sequence set forth in SEQ ID NO:7

SEQ ID NO:9 is the determined cDNA sequence of a human SPL with a deletion

SEQ ID NO:10 is the amino acid sequence of a human SPL with a deletion, encoded by the polynucleotide sequence set forth in SEQ ID NO:9.

SEQ ID NO:11 is the amino acid sequence of *C. elegans* SPL encoded by the polynucleotide sequence set forth in SEQ ID NO:12

SEQ ID NO:12 is the determined cDNA sequence of a *C. elegans* SPL

SEQ ID NO:13 is a PCR primer

SEQ ID NO:14 is a PCR primer

SEQ ID NO:15 is the determined cDNA sequence encoding the *Drosophila melanogaster* SPL SEQ ID NO:16 is the amino acid sequence of the *Drosophila melanogaster* SPL, encoded by the cDNA sequence set forth in SEQ ID NO:15

SEQ ID NO:17 is the determined cDNA sequence of a human SPL as set forth in Genbank Accession No: AF144638.

SEQ ID NO:18 is the amino acid sequence of a human SPL encoded by the polynucleotide sequence provided in SEQ ID NO:17.

SEQ ID NO:19 is the amino acid sequence of a first *Drosophila melanogaster* SK protein.

SEQ ID NO:20 is the amino acid sequence of a second *Drosophila melanogaster* SK protein.

SEQ ID NO:21 is the amino acid sequence of a human SK protein.

SEQ ID NO:22 is the cDNA encoding the human SK protein set forth in SEQ ID NO:21.

SEQ ID NO:23 is a cDNA sequence of human SPL, encoding the amino acid sequence set forth in SEQ ID NO:18.

SEQ ID NO:24 is the full length cDNA sequence for a first *Drosophila melanogaster* SK1, GI:21429173, encoding the amino acid sequence set forth in SEQ ID NO:19 and 28.

SEQ ID NO:25 is the full length cDNA sequence for a second *Drosophila melanogaster* SK2, GI:17862169, encoding the amino acid sequence set forth in SEQ ID NO:20 and 29.

SEQ ID NO:26 is the full length cDNA sequence for *Drosophila melanogaster* SPL, clone GH13783, GI:15292460.

SEQ ID NO:27 is the full length cDNA sequence for *Drosophila melanogaster* SPL, clone LP04413, GI:15292460.

SEQ ID NO:28 is the full length amino acid sequence of *Drosophila melanogaster* SKI CG1747.

SEQ ID NO:29 is the full length amino acid sequence of *Drosophila melanogaster* CG2159.

DETAILED DESCRIPTION OF THE INVENTION

The present invention provides compositions and methods, including screening assays, for agents that modulate sphingolipid metabolism and/or signaling wherein the agents have an effect on a level of sphingolipid intermediates and/or the activity of one or more components of a sphingolipid metabolic and/or signaling pathway and further provides methods for screening for said agents. Agents of the present invention have utility in the detection, diagnosis, and therapy of cancer and other diseases associated with altered sphingolipid metabolism and/or signaling.

Generally, the present invention relates to involvement of sphingolipid intermediates, and components involved in sphingolipid metabolism and/or signaling pathways, in numerous human diseases, including a variety of cancers (e.g. colon, breast, uterus, stomach, ovary, lung, kidney and adenocarcinoma of the rectum). In particular, the present invention derives from the unexpected observation that SPL expression is reduced in colloid cancer of the colon and adenocarcinoma of the colon. Also according to the present invention as disclosed below in greater detail, reduced SPL expression is observed in adenocarcinoma of the uterus, and SK expression is increased in a variety of tumor tissues as compared to normal tissue (e.g. breast, uterus, stomach, ovary, lung, kidney and adenocarcinoma of the rectum). Other components involved in sphingolipid metabolism and/or signaling pathways are also associated with other human diseases. In particular, failure and/or dysregulation of sphingolipid synthesis and/or catabolism are directly responsible for a number of human diseases, including hereditary sensory neuropathy type 1 and the group of lysosomal storage diseases called the sphingolipidoses (Bejaoui, K., Wu, C., Scheffler, M. D., Haan, G., Ashby, P., Wu, L., de Jong, P. and Brown, R. H., Jr. (2001). *Nat Genet* 27, 261-2.; Dawkins, J. L., Hulme, D. J., Brahmbhatt, S. B., Auer-Grumbach, M. and Nicholson, G. A. (2001). *Nat Genet* 27, 309-12.; Gable, K., Han, G., Monaghan, E., Bacikova, D., Natarajan, M., Williams, R. and Dunn, T. M. (2002). *J Biol Chem* 277, 10194-200.).

The present invention further relates to the unanticipated observation that *Drosophila melanogaster* SPL and SK mutants demonstrate altered sphingolipid metabolism. Surprisingly, SPL mutant flies have a flightless phenotype that can be restored by growing such mutant flies in the presence of an agent that modifies a component of the sphingolipid metabolic and/or signaling pathway. Thus, the present invention provides mutant and/or transgenic *Drosophila melanogaster* that have altered sphingolipid metabolism and/or signaling that can be used to screen agents useful for the detection, diagnosis, and treatment of the human diseases described herein.

Components of Sphingolipid Metabolism and/or Signaling

Any component of the sphingolipid metabolic and/or signaling pathway falls within the context of the present invention. As such, components of the sphingolipid metabolic and/or signaling pathway include but are not limited to, enzymes involved in these pathways (and the polynucleotides encoding said enzymes), such as, SPL, SK, ceramidase, S-1-PP, serine palmitoyltransferase (SPT), 3-keto dihydrosphingosine reductase, ceramide synthase, sphingosine desaturase, ceramide kinase, phosphoethanolamine cytidylyltransferase, CDP-ethanolamine phosphotransferase, acid sphingomyelinase, sphingomyelin synthase, neutral sphingomyelinase, oxosphinanine reductase, and glucosylceramide synthase. Components of the sphingolipid metabolic and/or signaling pathway further include intracellular or cell surface receptors, and the polynucleotides encoding said receptors, such as EDG receptors (e.g. EDG1, EDG3, EDG5, EDG6, EDG8) and CFTR.

Generally sphingolipid metabolism can be viewed as all synthetic and catabolic pathways involving any sphingolipid or sphingolipid intermediate as described herein. Sphingolipid signaling pathways are known in the art and can generally be viewed herein as any signaling pathway activated by a sphingolipid, such as the signaling pathways of sphingosine-1-phosphate such as those described in Pyne, S., and N. J. Pyne. 2000 *Biochem. J.* 349:385-402 and Pyne, S., and N. J. Pyne, 2000 *Pharmacology and Therapeutics* 88:115-131. However, the skilled artisan would recognize that other sphingolipid signaling pathways fall within the scope of the present invention and are contemplated herein.

The present invention therefore provides for polypeptides involved in sphingolipid metabolism and/or signaling, and polynucleotides encoding said polypeptides. As used herein, the term "polypeptide" encompasses amino acid chains of any length, including full length endogenous (i.e., native) proteins and variants of endogenous sequences that are involved in sphingolipid metabolism and/or signaling. Illustrative polypeptides of the present invention are set forth in SEQ ID NOs:2, 4, 6, 8, 10, 11, 16, 18-21, and 28-29. Particularly illustrative polypeptides are set forth in SEQ ID NOs:16, 18-21, and 28-29. "Variants" are polypeptides that differ in sequence from the polypeptides of the present invention only in substitutions, deletions and/or other modifications, such that the variant retains ability to modulate sphingolipid metabolism and/or signaling, for example by effecting the levels of one or more sphingolipid intermediates, such as intracellular S-1-P, ceramide, sphingosine, or other LCB or LCBP levels, which may be determined using a representative method described herein. Polypeptide variants generally encompassed by the present invention will typically exhibit at least about 70%, 75%, 80%, 85%, 86%, 87%, 88%, 89%, 90%, 91%, 92%, 93%, 94%, 95%, 96%, 97%, 98%, or 99% or more identity along its length, to a polypeptide sequence set forth herein. Within a polypeptide variant, amino acid substitutions are preferably made at no more than 50% of the amino acid residues in the native polypeptide, and more preferably at no more than 25% of the amino acid residues. Such substitutions are preferably conservative. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. Substitutions, deletions and/or amino acid additions may be made at any location(s) in the polypeptide, provided that the modification does not diminish the ability of the variant to modulate intracellular S-1-P levels. Thus, a variant may comprise only a portion of a native polypeptide sequence as provided herein. In addition, or alternatively, variants may contain additional amino acid sequences (such as, for example, linkers, tags and/or ligands), preferably at the amino and/or carboxy termini. Such sequences may be used, for example, to facilitate purification, detection or cellular uptake of the polypeptide.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Saitou, N. Nei, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Preferred examples of algorithms that are suitable for determining percent sequence identity and sequence similarity include the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

In one embodiment of the present invention, a polypeptide comprises a fusion protein comprising a component of a sphingolipid metabolic and/or signaling pathway. The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier or excipient. The fusion proteins may comprise multiple polypeptides or portions/variants thereof, as described herein, and may further comprise one or more polypeptide segments for facilitating the expression, purification, detection, and/or activity of the polypeptide(s).

In general, polypeptide components of a sphingolipid metabolic and/or signaling pathway, and polynucleotides encoding such polypeptides as described herein, may be prepared using any of a variety of techniques that are well known in the art. For example, a DNA sequence encoding native SK, SPL or SPT may be prepared by amplification from a suitable cDNA or genomic library using, for example, polymerase chain reaction (PCR) or hybridization techniques. Libraries may generally be prepared and screened using methods well known to those of ordinary skill in the art, such as those described in Sambrook et al., *Molecular Cloning: A Laboratory Manual*, Cold Spring Harbor Laboratories, Cold Spring Harbor, N.Y., 1989. cDNA libraries may be prepared from any of a variety of sources known to contain enzymes involved in sphingolipid metabolism. For example, SPL activity is ubiquitous with regard to species and mammalian tissues, with the exception of platelets, in which SPL activity is notably absent. In rat tissues, the highest levels of activity have been demonstrated in intestinal mucosa, liver and Harderian gland, with low activity in skeletal muscle and heart. Activity has also been demonstrated in a number of human (hepatoma cell line HB 8065, cervical carcinoma HeLa), mouse (hepatoma line BW1, mouse embryo 3T3-L1, Swiss 3T3 cells) and other cell lines, as well as in human cultured fibroblasts. Preferred cDNA libraries may prepared from human liver, intestine or brain tissues or cells. Other libraries that may be employed will be apparent to those of ordinary skill in the art. Primers for use in amplification may be readily designed based on the polynucleotide sequence of a native SPL, SK, SPT, S-1-PP or other polynucleotide as provided herein or known to the skilled artisan and available on any number of public databases.

A polynucleotide encoding a polypeptide component involved in a sphingolipid pathway (metabolic and/or signaling), such as a polynucleotide encoding SPL, SK, SPT, and S-1-PP, are also provided by the present invention. A polynucleotide as used herein may be single-stranded (coding or antisense) or double-stranded, and may be DNA (genomic, cDNA or synthetic) or RNA molecules. Thus, within the context of the present invention, a polynucleotide encoding a polypeptide may also be a gene. A gene is a segment of DNA involved in producing a polypeptide chain; it includes regions preceding and following the coding region (leader and trailer) as well as intervening sequences (introns) between individual coding segments (exons). Additional coding or non-coding sequences may, but need not, be present within a polynucleotide of the present invention, and a polynucleotide may, but need not, be linked to other molecules and/or support materials. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

Polynucleotides of the present invention may comprise a native sequence (i.e., an endogenous polynucleotide, for instance, a native or non-artificially engineered or naturally occurring gene as provided herein) encoding SPL, SK, SPT, or other components of the sphingolipid metabolic or signaling pathways, alternate form sequence, or a portion or splice variant thereof) or may comprise a variant of such a sequence. Polynucleotide variants may contain one or more substitutions, additions, deletions and/or insertions such that the activity of the encoded polypeptide is not substantially diminished, as described herein. The effect on the activity of the encoded polypeptide may generally be assessed as described herein. Variants preferably exhibit at least about 70% identity, more preferably at least about 80%, 85%, 86%, 87%, 88%, 89%, identity and most preferably at least about 90%, 91%, 92%, 93%, 94%, 95%, 96%, 97%, 98%, or 99% identity to a polynucleotide sequence that encodes a native polypeptide involved in sphingolipid metabolism or signaling, such as the polynucleotides set forth in SEQ ID NOs:1, 3, 5, 7, 9, 12, 15, 17, and 22-27 or an alternate form or a portion thereof, and the polynucleotides that encode a polypeptide sequence as recited in any one of SEQ ID NOs:2, 4, 6, 8, 10, 11, 16, and 18-21, or a portion thereof. Particularly illustrative polynucleotides of the present invention comprise polynucleotides encoding a polypeptide comprising an amino acid sequence shown in FIG. 1, such as the amino acid sequences set forth in SEQ ID NOs:18-21 and 28-29. The percent identity may be readily determined by comparing sequences using computer algorithms well known to those having ordinary skill in the art and described herein.

Polynucleotides that are substantially homologous to a sequence complementary to a polynucleotide as described herein are also within the scope of the present invention. "Substantial homology," as used herein refers to polynucleotides that are capable of hybridizing under moderately stringent conditions to a polynucleotide complementary to an SK, SPL, SPT, S-1-PP or other polynucleotide sequence provided herein, provided that the encoded polypeptide variant retains enzymatic or signaling activity. Suitable moderately stringent conditions include prewashing in a solution of 5×SSC, 0.5% SDS, 1.0 mM EDTA (pH 8.0); hybridizing at 50-65° C., 5×SSC, overnight; followed by washing twice at 65° C. for 20 minutes with each of 2×, 0.5× and 0.2×SSC containing 0.1% SDS. Nucleotide sequences that, because of code degeneracy, encode a polypeptide encoded by any of the above sequences are also encompassed by the present invention.

A polynucleotide as described herein may be identified using standard yeast genetics known to the skilled artisan. A cDNA expression library may be generated using a regulatable yeast expression vector (e.g., pYES, which is available from Invitrogen, Inc.) and standard techniques. A yeast mutant strain may then be transformed with the cDNA library, and endogenous cDNAs having the ability to functionally complement the yeast sphingolipid metabolism defect (i.e., restore the ability to grow in the presence of D-erythro-sphingosine or other appropriate sphingolipid intermediate) may be isolated.

A polynucleotide encoding a polypeptide affecting sphingolipid metabolism and/or signaling may also be identified based on cross-reactivity of the protein product with antibodies that react to SPL, SK, SPT, and other polypeptides involved in sphingolipid metabolism or signaling, which may be prepared as described herein. Such screens may generally be performed using standard techniques (see Huynh et al., "Construction and Screening cDNA Libraries in λgt11," in D. M. Glover, ed., *DNA Cloning: A Practical Approach,* 1:49-78, 1984 (IRL Press, Oxford)).

Polypeptides of the present invention may be prepared by expression of recombinant DNA encoding the polypeptide in cultured host cells. Preferably, the host cells are bacteria, yeast, insect or mammalian cells, and preferably the host cells are *S. cerevisiae* bst1Δ cells. The recombinant DNA may be cloned into any expression vector suitable for use within the host cell and transfected into the host cell using techniques well known to those of ordinary skill in the art. A suitable expression vector contains a promoter sequence that is active in the host cell. A tissue-specific or conditionally active promoter may also be used. Preferred promoters express the polypeptide at high levels. As is readily appreciated by the skilled artisan, the polynucleotide encoding the polypeptide of interest is cloned into the expression vector such that it is operably linked to the promoter such that the polypeptide of interest is properly translated. Thus, in certain embodiments, the ligated DNA sequences are operably linked to suitable transcriptional or translational regulatory elements. The regulatory elements responsible for expression of DNA are generally located only 5' to the DNA sequence encoding the first polypeptides. Similarly, stop codons required to end translation and transcription termination signals are only present 3' to the DNA sequence encoding the second polypeptide.

Optionally, the construct may contain an enhancer, a transcription terminator, a poly(A) signal sequence, a bacterial or mammalian origin of replication and/or a selectable marker, all of which are well known in the art. Enhancer sequences may be included as part of the promoter region or separately. Transcription terminators are sequences that stop RNA polymerase-mediated transcription. The poly(A) signal may be contained within the termination sequence or incorporated separately. A selectable marker includes any gene that confers a phenotype on the host cell that allows transformed cells to be identified. Such markers may confer a growth advantage under specified conditions. Suitable selectable markers for bacteria are well known and include resistance genes for ampicillin, kanamycin and tetracycline. Suitable selectable markers for mammalian cells include hygromycin, neomycin, genes that complement a deficiency in the host (e.g., thymidine kinase and TK⁻cells) and others well known in the art. For yeast cells, one suitable selectable marker is URA3, which confers the ability to grow on medium without uracil.

DNA sequences expressed in this manner may encode a native polypeptide (e.g., human) involved in sphingolipid metabolism or signaling, such as SK, SPL, SPT, or may encode portions or other variants of a native polypeptide involved in sphingolipid metabolism or signaling, such as SK, SPL, SPT or other polypeptides of the present invention described herein. DNA molecules encoding variants of a native polynucleotide may generally be prepared using standard mutagenesis techniques, such as oligonucleotide-directed site-specific mutagenesis, and sections of the DNA sequence may be removed to permit preparation of truncated polypeptides.

To generate cells that express a polynucleotide encoding a polypeptide, such as SPL, SPT, SK, involved in sphingolipid metabolism, cells may be transfected, transformed or transduced using any of a variety of techniques known in the art. Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). Such techniques may result in stable transformnants or may be transient. One suitable transfection technique is electroporation, which may be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation may be obtained from manufacturers. Other suitable methods for transfection will depend upon the type of cell used (e.g., the lithium acetate method for yeast), and will be apparent to those of ordinary skill in the art. Following transfection, cells may be maintained in conditions that promote expression of the polynucleotide within the cell. Appropriate conditions depend upon the expression system and cell type, and will be apparent to those skilled in the art.

Polypeptides involved in sphingolipid metabolism may be expressed in transfected cells by culturing the cell under conditions promoting expression of the transfected polynucleotide. Appropriate conditions will depend on the specific host cell and expression vector employed, and will be readily apparent to those of ordinary skill in the art. For commercially available expression vectors, the polypeptide may generally be expressed according to the manufacturer's instructions. For certain purposes, expressed polypeptides of this invention may be isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and/or affinity chromatography.

Sphingolipid Intermediates

As noted herein above, the present invention provides agents that modulate the activity of one or more components of a sphingolipid metabolic and/or signaling pathway. The agents of the present invention also may alter the levels (e.g., relative or absolute amounts, concentrations, stability, or the like) of at least one sphingolipid intermediate. Sphingolipid intermediates of the present invention include any sphingolipid intermediate in the sphingolipid metabolic pathway. As such, the sphingolipid intermediates of the present invention include, but are not limited to, long chain bases (LCBs) and phosphorylated long chain bases (LCBPs) comprising sphingoid backbone structures of between $C_{10}$ and $C_{20}$. In one embodiment, the backbone structure comprises $C_{14}$, $C_{15}$, $C_{16}$, $C_{17}$, $C_{18}$, $C_{19}$, or $C_{20}$. In a further embodiment, the sphingolipid intermediates of the present invention include endogenous free sphingoid bases isolated from *Drosophila melanogaster*, including $C_{14}$ and $C_{16}$ sphingosine and $C_{14}$ and $C_{16}$ dihydrosphingosine. In another embodiment, a sphingolipid intermediate comprises any one or more of S-1-P, hexadecanal, phosphoethanolamine, ceramide, sphingosine, 3-keto-dihydrosphingosine, dihydrosphingosine, sphingomyelin, dihydroceramide, ceramide-1-phosphate, dihydrosphingosine-1-phosphate, ethanolamine phosphate, long chain unsaturated aldehyde, and long chain saturated aldehyde. The skilled artisan would readily appreciate that any sphingolipid intermediate species that is affected or generated by any one or more components of the sphingolipid metabolic and/or signaling pathway fall within the scope of the present invention and can be identified using a variety of assays known in the art and further described herein.

Agents that Modulate Sphingolipid Intermediates and/or Components of Sphingolipid Metabolism and/or Signaling Agents for use according to the present invention are defined as any composition, compound, substance, molecule, material, product or the like, whether artificial or naturally derived, as described herein in further detail, that modulate sphingolipid metabolism and/or signaling. An agent that modulates sphingolipid metabolism and/or signaling is an agent that alters (e.g., increases or decreases in a statistically significant manner) the level of at least one sphingolipid intermediate or the activity of at least one component of a sphingolipid metabolic and/or signaling pathway. Alteration of a level or activity comprises any statistically significant change, e.g. increase or decrease, in the level of one or more intermediates or in the activity of one or more components of sphingolipid metabolism and/or signaling as described herein, when an isolated component, or a host cell or an animal comprising an intermediate or component is contacted with the agent as compared to an isolated component, a host cell or animal comprising an intermediate or component that is not contacted with the agent. As such, in one embodiment, modulation comprises an altered level, e.g. a decrease or increase in, a polynucleotide encoding a protein involved in sphingolipid metabolism and/or signaling as described herein. Numerous methods for detecting polynucleotide levels (e.g. gene expression) are known in the art and are useful in the context of the instant invention. Illustrative methods are described in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.) and elsewhere.

In a further embodiment, modulation comprises an altered activity level, that is a statistically significant decrease or increase in enzymatic activity of any enzyme involved in sphingolipid metabolism and/or signaling, such as SPL, SK, SPT, S-1-PP, and the like. Numerous methods for detecting and measuring enzymatic activity are known in the art and can be used in the context of the present invention (see e.g. Current Protocols in Protein Science, John Wiley & Sons, Inc., Boston, Mass.). Certain illustrative methods are described in, e.g., Saba, J. D., Nara, F., Bielawska, A., Garrett, S. and Hannun, Y. A. (1997). *J Biol Chem* 272, 26087-26090, and Van Veldhoven, P. P. and Mannaerts, G. P. (1991). *J Biol Chem* 266, 12502-7, Williams, R, Wang E and Merrill A, 1984., *Arch Biochem Biophys* 228:282-291., Caligan, T B, Peters K, Ou J, Wang E, Saba J and Merrill A H, Jr., 2000. *Analytical Biochemistry* 281:36-44.

In certain embodiments, modulation comprises a statistically significant decrease or increase in the levels of (i.e. altered level of) one or more sphingolipid intermediates as described herein, such as S-1-P, ceramide, sphingosine, or other LCBs or LCBPs. A variety of methods for measuring sphingolipid intermediates (e.g., sphingosine-1-phosphate or its degradation products, ceramide, sphingosine, etc.) is known in the art and may be useful in the context of the present invention. Illustrative methods are described in the following references: Bose, R and Kolesnick R, 2000., *Methods in Enzymology* 322:373-378; Fyrst, H, Oskouian B, Kuypers F and Saba J, 1999, *Biochemistry* 38:5864-5871; Fyrst, H, Pham D V, Lubin B H and Kuypers F A, 1996, *Biochemistry* 35:2644-2650.

In certain embodiments modulation of sphingolipid metabolism and/or signaling comprises an increase or decrease in cellular proliferation, apoptosis, angiogenesis, drug resistance and cell motility. A variety of assays are known in the art to measure these activities, including those described in Current Protocols in Immunology, or Current Protocols in Cell Biology, both published by John Wiley & Sons, Inc., Boston, Mass.

Candidate agents of the present invention include polynucleotides encoding polypeptide components of the sphingolipid metabolic and/or signaling pathways such as any of said polypeptide components described herein. Agents of the present invention further include a polypeptide comprising an enzyme involved in sphingolipid metabolism or signaling such as those described herein.

Candidate agents further include any of the sphingolipid intermediates described herein, such as, but not limited to, S-1-P, hexadecanal, phosphoethanolamine, ceramide, sphingosine, 3-keto-dihydrosphingosine, dihydrosphingosine, sphingomyelin, dihydroceramide, ceramide-1-phosphate, dihydrosphingosine-1-phosphate, ethanolamine phosphate, long chain unsaturated aldehyde, and long chain saturated aldehyde. In one embodiment, an agent of the present invention comprises LCBs and LCBPs such as $C_{14}$ and $C_{16}$ sphingosine and $C_{14}$ and $C_{16}$ dihydrosphingosine identified in the *Drosophila melanogaster* as decribed herein.

In one particular embodiment, agents of the present invention decrease the level of endogenous S-1-P. Such modulating agents may be identified using methods described herein and used, for example, in cancer therapy and treatment of muscle developmental defects and cardiomyopathy. It has also been found, within the context of the present invention, that the detection of alterations in endogenous S-1-P levels can be used to diagnose cancer and defects in muscle developmental and cardiomyopathy, and to assess the prognosis for recovery. The present invention further provides such diagnostic methods and kits.

Agents which inhibit or block SK activity or expression are also provided in the present invention. In one aspect of the invention, such drugs may be effective treatment for at least some kinds of cancer, especially those in which a dominant Ras mutation is involved. Methods for the identification of new and effective pharmacological agents which inhibit SK activity, as well as drug targets downstream of S-1-P signaling are also provided in the present invention. As used herein, inhibition of SK activity means to decrease the level of SK enzymatic activity as measured using any number of assays known in the art, or certain illustrative assays described herein. Preferably, the decrease in enzymatic SK activity is a statistically significant decrease in enzymatic activity as compared to an appropriate control. Likewise inhibition may apply to the activity of any component of a sphingolipid metabolic and/or signaling pathway, such as SPL, SPT, and the like.

Agents of the present invention that modulate sphingolipid metabolism and/or signaling are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Figure 3:
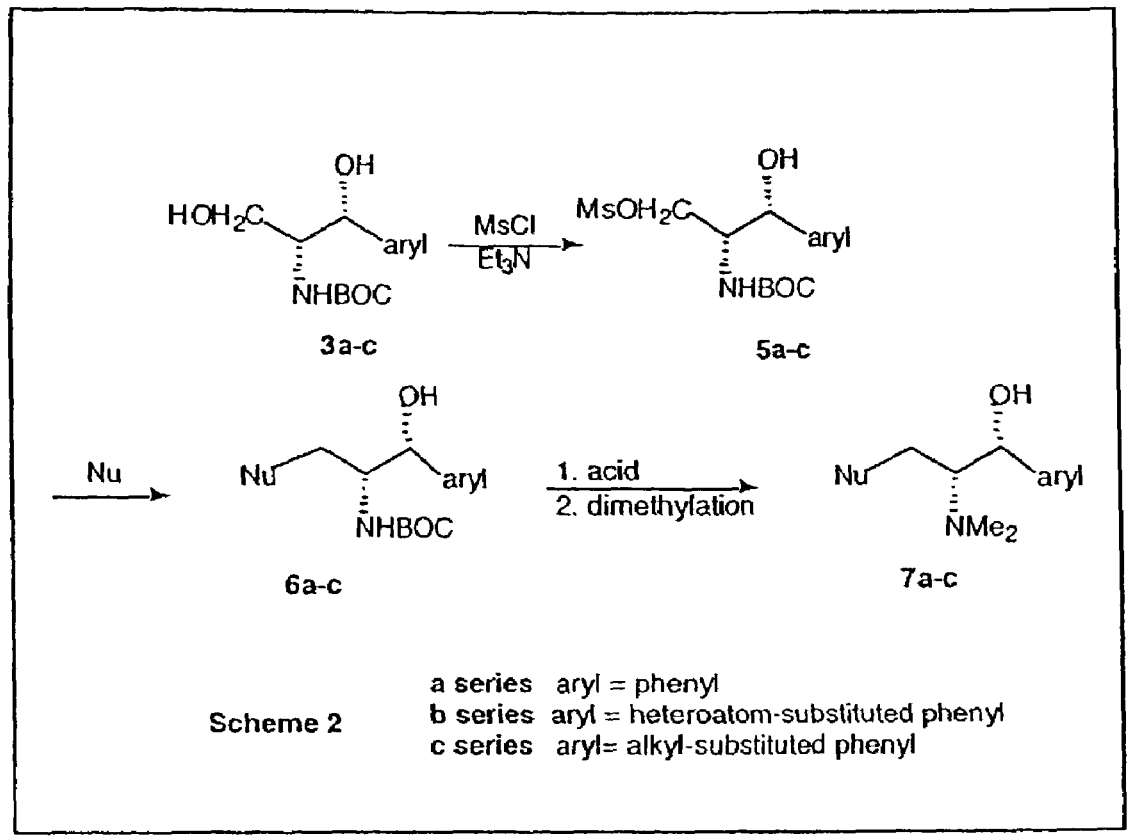
FIG. 3 shows a second chemical synthesis scheme.

Illustrative agents of the present invention include arrays of rationally designed chemicals with homology to sphingolipids. In particular synthetic analogs are created that modulate sphingolipid metabolic and/or signaling pathways. In one embodiment, a rationally designed chemical library includes 1-aryl-2-dimethylaminopropane-1,3-diol derivatives. Derivative is a term understood by the ordinarily skilled artisan. For example, derivative means a compound that can be imagined to arise from a partent compound by replacement of one atom with another atom or group of atoms. Within the context of this invention, these derivatives are rationally designed. Four diastereomers (D or L, erythro or threo) are possible for each member of the library. In one particular embodiment, the 1-aryl-2 dimethylaminopropane-1,3-diol derivative is derivitized by modifying the amine, the fatty acid amide and the benzene ring of PDMP. In one particular embodiment, the fatty acid amide group is replaced with two N-methyl groups. The skilled artisan would readily appreciate that similar variation can be made in the polar and aromatic substituents and would be particularly illustrative candidate agents within the context of the instant invention. In another embodiment of the present invention, a 1-aryl-2-dimethylaminopropane-1,3-diol derivative is designed such that lipophilic alkyl groups attached to the arene ring would more closely mimic the character of sphingosine. In one particular embodiment, the synthetic plan makes use of the well-known Garner aldehyde (See 1 in FIG. 2) as starting material, since 1 is readily available in either enantiomeric form. In one embodiment, the D- or L-enantiomer of 1 is used as starting material, and pure erythro stereoisomers of each library member are prepared. In an additional embodiment, a novel and flexible route for assembling the corresponding threo analogues (4a-c, FIG. 2) is followed using a straightforward extension of methodology for making PDMP analogues. The strategy relies on the syn-selective addition to 1 of arylmetal compounds (Aryl-Met) in the presence of certain sulfide and phosphine additives. In this embodiment, both the erythro and threo synthetic routes are modified to prepare substituted variations at the primary carbon atom. A representative synthetic procedure is shown in FIG. 3 for the preparation of 7a-c. Thus, a wide range of nitrogen, oxygen, and carbon nucleophiles could react with mesylates like 5a-c and furnish new libraries of dimethylated PDMP analogues and homologues for use as candidates in the context of the present invention.

Candidate agents for use in a method of screening for a modulator of sphingolipid metabolism and/or signaling according to the present invention may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a mutant or transgenic *Drosophila melanogaster* as described herein, and then assayed for their ability to restore the wild type phenotype to said mutant and/or transgenic *Drosophila melanogaster*. Compounds so identified as capable of influencing components of the sphingolipid metobolic or signaling pathway (e.g., by altering levels of a sphingolipid intermediate such as S-1-P, ceramide, or sphingosine) are valuable for therapeutic and/or diagnostic purposes, since they permit treatment and/or detection of diseases associated with sphingolipid metabolism and/or signaling.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666) or other compositions that may include small molecules as provided herein (see e.g., PCT/US94/08542, EP 0774464, U.S. Pat. Nos. 5,798,035, 5,789,172, 5,751,629). Those having ordinary skill in the art will appreciate that a diverse assortment of such libraries may be prepared according to established procedures, and tested using the screening methods according to the present disclosure.

Candidate agents of the present invention further provides antibodies that bind to a polypeptide involved in sphingolipid metabolism or signaling. Antibodies may function as modulating agents (as discussed further below) to inhibit or block activity of the polypeptides of the present invention in vivo. Alternatively, or in addition, antibodies may be used within screens for endogenous activity of the polypeptides of the present invention, e.g., SK, SPL, SPT, or modulating agents, for purification of said polypeptides, for assaying the level of activity of said polypeptides within a sample and/or for studies of expression of said polypeptides. Such antibodies may be polyclonal or monoclonal, and are generally specific for one or more polypeptides involved in sphingolipid metabolism and/or one or more variants thereof. Within certain preferred embodiments, antibodies are polyclonal.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising an SPL polypeptide or antigenic portion thereof is initially injected into a suitable animal (e.g., mice, rats, rabbits, sheep and goats), preferably according to a predetermined schedule incorporating one or more booster immunizations. The use of rabbits is preferred. To increase immunogenicity, an immunogen may be linked to, for example, glutaraldehyde or keyhole limpet hemocyanin (KLH). Following injection, the animals are bled periodically to obtain post-immune serum containing polyclonal antibodies that bind to a polypeptide involved in sphingolipid metabolism, such as SK, SPL, SPT, S-1-PP. Polyclonal antibodies may then be purified from such antisera by, for example, affinity chromatography using a polypeptide of the present invention, such as SK or SPL, or antigenic portion thereof coupled to a suitable solid support. Such polyclonal antibodies may be used directly for screening purposes and for Western blots.

More specifically, an adult rabbit (e.g., NZW) may be immunized with 10 µg purified (e.g., using a nickel-column) SK or SPL polypeptide emulsified in complete Freund's adjuvant (1:1 v/v) in a volume of 1 mL. Immunization may be achieved via injection in at least six different subcutaneous sites. For subsequent immunizations, 5 µg of an SK, SPL, or SPT polypeptide may be emulsified in in complete Freund's adjuvant and injected in the same manner. Immunizations may continue until a suitable serum antibody titer is achieved (typically a total of about three immunizations). The rabbit may be bled immediately before immunization to obtain pre-immune serum, and then 7-10 days following each immunization.

For certain embodiments, monoclonal antibodies may be desired. Monoclonal antibodies may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

An antibody that specifically binds to a component of a sphingolipid metabolic and/or signaling pathway may interact with said polypeptide component via specific binding if the antibody binds the polypeptide with a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$ to $10^9$ $M^{-1}$. Affinities of binding partners such as antibodies and the polypeptides that they bind to can be readily determined using conventional techniques, for example those described by Scatchard et al., *Ann. N.Y. Acad. Sci.* 51:660 (1949) and in Current Protocols in Immunology, or Current Protocols in Cell Biology, both published by John Wiley & Sons, Inc., Boston, Mass.

As noted above, the present invention provides agents that alter the expression (transcription or translation), stability and/or activity of a polypeptide involved in sphingolipid metabolism. To identify such a modulating agent, any of a variety of screens may be performed. Candidate modulating agents may be obtained using well known techniques from a variety of sources, such as plants, fungi or libraries of chemicals, small molecules or random peptides. Antibodies that bind to a polypeptide of the present invention, and anti-sense polynucleotides that hybridize to a polynucleotides that encodes a protein involved in sphingolipid metabolism, may be candidate modulating agents. Preferably, a modulating agent has a minimum of side effects and is non-toxic. For some applications, agents that can penetrate cells are preferred.

The subject methods find use in the screening of a variety of different potentially therapeutic candidate agents. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents of the present invention further include agents that restore wild type phenotype to mutant or transgenic flies as described herein, in particular in the Examples. In one embodiment, modulating agents are screened by culturing or otherwise contacting the agent with a *Drosophila melanogaster* null mutant for a time sufficient to observe in said mutant *Drosophila melanogaster* an effect of the agent on a level of either at least one sphingolipid intermediate, or the activity of at least one component of sphingosine metabolism and/or signaling pathway. In one embodiment, the *Drosophila melanogaster* null mutant has a flightless phenotype caused by abnormal development of indirect flight muscles (IFM) during metamorphosis. This phenotype provides a novel schema by which to elucidate sphingolipid metabolism and signaling, identify genetic suppressors and identify chemicals which modulate sphingolipid metabolism and/or signaling through their effect on key components in the sphingolipid metabolic and/or signaling pathway. Agents that result in a statistically significant alteration in the level of a sphingolipid intermediate or alteration in the level of activity of a component of a sphingolipid metabolic or signling pathway is an agent that modulates sphingolipid metabolism and/or signaling. Agents that result in a statistically significant restoration in the phenotype of a mutant or transgenic fly grown or otherwise cultured in the presence of said agent as compared to a mutant or transgenic fly grown or otherwise cultured in the absence of the agent as described herein is an agent that modulates sphingolipid metabolism and/or signaling.

As mentioned above, the subject mutant and transgenic flies find particular utility in screening assays designed to identify diagnostic and therapeutic compounds for a variety of human diseases as described herein, such as numerous cancers including breast, colon, uterus, stomach, ovary, lung, kidney and rectal cancer, and diagnosis and treatment of hereditary sensory neuropathy type 1 and the sphingolipidoses. Through use of the subject transgenic flies (or cells derived therefrom depending on the particular screening assay), one can identify compounds that have activity with respect to sphingolipid metabolism and/or signaling and therefore, the diseases associated with modulation of sphingolipid metabolism and/or signaling. Compounds have activity with respect to sphingolipid metabolism and/or signaling if they modulate or have an effect on at least one parameter or symptom of the disease, such as tumor development, etc., where the modulatory activity may be to reduce or enhance the magnitude of the symptom. Tumors comprise abnormal masses of tissue and can be benign or cancerous. As would be readily appreciated by the skilled artisan, there are dozens of different types of tumors and their identification and diagnosis are known in the art and can be determined by a qualified clinician.

Thus, the screening methods of subject invention can be used to identify compounds that modulate the progression of disease, e.g. by binding to, modulating, enhancing or repressing the activity of a protein or peptide involved in the sphingolipid metabolism and/or signaling, and/or compounds that ameliorate, alleviate or even remove the phenotypic symptoms of the disease, where such activity may or may not be the result of activity with respect to the underlying mechanism of the disease.

Assays of the invention make it possible to identify compounds which ultimately: (1) have a positive affect with respect to diseases associated with sphingolipid metabolism and/or signaling and as such are therapeutics, e.g., agents which arrest or reverse development of tumors or ameliorate or alleviate the symptoms of such a condition; or (2) have an adverse affect with respect to the disease and as such should be avoided as therapeutic agents.

In certain preferred screening methods of the subject invention, a quantity of a candidate agent is generally orally administered to the fly. Following oral administration, the affect of the candidate agent on phenotype of the fly is determined, typically by comparison with a control (i.e. a mutant or transgenic fly to which the candidate agent has not been administered). The effect of the candidate agent is determined by determining whether one or more of the phenotypic characteristics of the mutant or transgenic fly as described herein are exacerbated or ameliorated in the test fly as compared to the control fly, where characteristics that are monitored include levels of sphingolipid intermediates, flight behavior, flight muscle developmental defects, and the like. The candidate agent is generally orally administered to the fly by mixing the agent into the fly nutrient medium and placing the medium in the presence of the fly, (either the larva or adult fly) such that the fly feeds on the medium. Generally a plurality of assay mixtures are run in parallel with different candidate agent concentrations (or no candidate agent) to obtain a differential response to the various concentrations of the candidate agent. Typically, one of these test groups serves as a negative control, i.e., no candidate agent is present. In a preferred embodiment, a high throughput screening protocol is employed, in which a large number of candidate agents are tested in parallel using a large number of flies. By "large number" is meant a plurality, where plurality means at least 50, usually at least 100, and more usually at least 1000, where the number of may be 10,000 or 50,000 or more, but in many instances will not exceed 5000.

A modulating agent may additionally comprise, or may be associated with, a targeting component that serves to direct the agent to a desired tissue or cell type. As used herein, a "targeting component" may be any substance (such as a compound or cell) that, when linked to a compound enhances the transport of the compound to a target tissue, thereby increasing the local concentration of the compound. Targeting components include antibodies or fragments thereof, (e.g. anti-tumor antibodies) receptors, ligands and other molecules that bind to cells of, or in the vicinity of, the target tissue. Known targeting components include hormones, antibodies against cell surface antigens, lectins, adhesion molecules, tumor cell surface binding ligands, steroids, cholesterol, lymphokines, fibrinolytic enzymes and other drugs and proteins that bind to a desired target site. In particular, anti-tumor antibodies and compounds that bind to an estrogen receptor may serve as targeting components. An antibody employed in the present invention may be an intact (whole) molecule, a fragment thereof, or a functional equivalent thereof (e.g. antigen-binding fragments). Examples of antibody fragments are F(ab') 2,–Fab', Fab and F[v] fragments, which may be produced by conventional methods or by genetic or protein engineering. Linkage may be via any suitable covalent bond using standard techniques that are well known in the art. Such linkage is generally covalent and may be achieved by, for example, direct condensation or other reactions, or by way of bi- or multi-functional linkers.

Assays for Detecting Modulation of Components of Sphingolipid Metabolism and/or Signaling and/or Sphingolipid Intermediates Numerous assays for detecting modulation of components of sphingolipid metabolism and/or signaling are available in the art. Illustrative assays are described further herein, for example as described in the Example section.

Numerous methods for detecting polynucleotides of the present invention are known in the art and are useful in the context of the instant invention. Illustrative methods are described in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.), and elsewhere. In one embodiment, polynucleotide expression is measured using any number of hybridization techniques. In further embodiments, polynucleotide expression is measure using amplfication techniques, such as RT-PCR, PCR, quatitative-competitive (QC) PCR, and real-time PCR.

Numerous methods for detecting and measuring enzymatic activity of components involved in sphingolipid metabolism and/or signaling are known in the art and can be used in the context of the present invention (see e.g. Current Protocols in Protein Science, John Wiley & Sons, Inc., Boston, Mass.). Certain illustrative methods are described in Saba, J. D., Nara, F., Bielawska, A., Garrett, S. and Hannun, Y. A. (1997). *J Biol Chem* 272, 26087-26090, and Van Veldhoven, P. P. and Mannaerts, G. P. (1991). *J Biol Chem* 266, 12502-7, Williams, R, Wang E and Merrill A, 1984., *Arch Biochem Biophys* 228:282-291., Caligan, T B, Peters K, Ou J, Wang E, Saba J and Merrill A H, Jr., 2000. *Analytical Biochemistry* 281:36-44.

In one embodiment, SK activity of an SK polypeptide or variant thereof may generally be assessed using an in vitro assay that detects the production of labeled substrate (i.e., sphingosine-1-phosphate, or a derivative thereof). SK is responsible for the phosphorylation of sphingosine to generate S-1-P. In one embodiment of the present invention, an in vitro assay for SK requires both ATP and a divalent cation (magnesium, calcium or manganese) for the phosphorylation of the hydroxyl group on the first carbon of sphingosine. SK activity may be assayed in tissues from a variety of species, including human and porcine platelets, bovine brain and kidney, rat liver, the yeast *Hansenula ciferrii*, and *Tetrahymena pyriformis*. In one embodiment, the assay requires a fixed ratio of magnesium to ATP of 5:1 and a neutral pH (between 7.2-7.5). SK is found in the cytoplasm of platelets and is associated with membranes in rat brain and several other tissues. D-erythro-sphingosine, the naturally occurring isomer of sphingosine and most abundant sphingoid base in most mammalian cells, serves as a substrate for SK from all sources. Sphingosine inhibits the activity of protein kinase C, and stereospecificity for the erythro conformation has been demonstrated in mixed micellar assays using human platelet and rat brain-derived enzyme. A variety of long chain bases can also serve as substrates for SK, including erythro-dihydrosphingosine and phytosphingosine. SK activity increases with the carbon chain length of a D-erythro-dihydrosphingosine substrate. In one embodiment, stimulation of Swiss 3T3 cells with some inducers of proliferation (fetal calf serum or PDGF) can be used to assay an increase in both sphingosine levels and SK activity. Illustrative stimuli which can be used to activate SK include nerve growth factor, muscarinic acetylcholine agonists, TNFα, and cross-linking of the FcεRI and FcγRI immunoglobulin receptors. Additional mitogens such as the b subunit of the cholera toxin and 12-O-tetradecanoyl phorbol-13-acetate may also be used to increase SK enzyme activity.

Within certain embodiments, an in vitro assay for SK activity may be performed using cellular extracts prepared from cells that express a polypeptide of interest. Preferably, in the absence of a polynucleotide encoding an SK polypeptide, such cells do not produce a significant amount of endogenous SK (i.e., a cellular extract should not contain a detectable increase in the level of SK, as compared to buffer alone without extract). Illustrative assays for detection of SK activity are known in the art, such as those described herein in the Examples.

Screens for modulating agents that alter expression or stability of a polypeptide of the present invention may be readily performed using well known techniques that detect the level of protein or mRNA. Suitable assays include RNAse protection assays, in situ hybridization, ELISAs, Northern blots and Western blots. Such assays may generally be performed using standard methods (see Sambrook et al., *Molecular Cloning: A Laboratory Manual*, Cold Spring Harbor Laboratories, Cold Spring Harbor, N.Y., 1989). For example, to detect mRNA encoding SK, SPL or other polynucleotides involved in the metabolism of sphingolipids, a nucleic acid probe complementary to all or a portion of the gene sequence of interest may be employed in a Northern blot analysis of mRNA prepared from suitable cells. Additionally, In situ hybridization may be performed as described in Blair, S. (Blair S., 2000. Imaginal discs. In *Drosophila*Protocols. W. Sullivan, M. Ashburner, and R. Hawley, editors. Cold Spring Harbor Laboratory Press, Cold Spring Harbor, N.Y. 159-175).

Alternatively, real-time PCR can also be used to detect levels of mRNA encoding SPL, SK, or other polypeptides involved in sphingolipid metabolism as described herein (see Gibson et al., *Genome Research* 6:995-1001, 1996; Heid et al., *Genome Research* 6:986-994, 1996). The first-strand cDNA to be used in the quantitative real-time PCR is synthesized from 20 µg of total RNA that is first treated with DNase I (e.g., Amplification Grade, Gibco BRL Life Technology, Gaithersburg, Md.), using Superscript Reverse Transcriptase (RT) (e.g., Gibco BRL Life Technology, Gaithersburg, Md.). Real-time PCR is performed, for example, with a Gene-Amp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence is monitored during the whole amplification process. The optimal concentration of primers is determined using a checkerboard. The PCR reaction is performed in 25 µl volumes that include 2.5 µl of SYBR green buffer, 2 µl of cDNA template and 2.5 µl each of the forward and reverse primers for the SPL gene, or other gene of interest. The cDNAs used for RT reactions are diluted approximately 1:10 for each gene of interest and 1:100 for the β-actin control. In order to quantitate the amount of specific cDNA (and hence initial mRNA) in the sample, a standard curve is generated for each run using the plasmid DNA containing the gene of interest. Standard curves are generated using the Ct values determined in the real-time PCR which are related to the initial cDNA concentration used in the assay. Standard dilution ranging from 20-2×10$^6$ copies of the SPL gene or other gene of interest are used for this purpose. In addition, a standard curve is generated for β-actin ranging from 200 fg-2000 fg. This enables standardization of the initial RNA content of a sample to the amount of β-actin for comparison purposes. The mean copy number for each sample tested is normalized to a constant amount of β-actin, allowing the evaluation of the observed expression levels of SPL or other genes of interest.

To detect a protein of the present invention, a reagent that binds to the protein (typically an antibody, as described herein) may be employed within an ELISA or Western assay. Following binding, a reporter group suitable for direct or indirect detection of the reagent is employed (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

Alternatively, or in addition, a candidate modulating agent may be tested for the ability to alter enzymatic activity, such as SPL or SK activity, using an in vitro assay as described herein (see Van Veldhoven and Mannaerts, J. Biol. Chem. 266:12502-07, 1991) that detects the degradation of labeled substrate (i.e., sphingosine-1-phosphate, or a derivative thereof). Briefly, a solution (e.g., a cellular extract) containing an SK or SPL polypeptide (e.g., 10 nM to about 10 mM) may be incubated with a candidate modulating agent (typically 1 nM to 10 mM, preferably 10 nM to 1 mM) and a substrate (e.g., 40 µM) at 37° C. for 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. A modulating agent (e.g., an antibody or other modulating agent as described herein) that alters SK or SPL activity results in a statistically significant increase or decrease in the degradation of sphingosine-1-phosphate, relative to the level of degradation in the absence of modulating agent. Such modulating agents may be used to increase or decrease SK or SPL activity in a cell culture or a mammal, as described herein.

Modulating agents that alter the SPL activity of an SPL polypeptide or variant thereof may generally be assessed using an in vitro assay that detects the degradation of labeled substrate (i.e., sphingosine-1-phosphate, or a derivative thereof). Within such assays, pyridoxal 5'-phosphate is normally a requirement for SPL activity. In addition, the reaction generally proceeds optimally at pH levels around 7.4-7.6 and requires chelators due to sensitivity toward heavy metal ions. PH levels may be from 6.5, 6.7, 6.9, 7.0, 7.1, 7.2, 7.3, 7.7, 7.8, 7.9, 8.0, 8.1, 8.2, 8.3, 8.4, or 8.5. The substrate should be a D-erythro isomer, but in derivatives of sphingosine-1-phosphate the type and chain length of sphingoid base may vary. In general, an assay as described by Van Veldhoven and Mannaerts, J. Biol. Chem. 266:12502-07, 1991 may be employed. Briefly, a solution (e.g., a cellular extract) containing the polypeptide may be incubated with about 40 µM substrate at 37° C. for about 1 hour in the presence of, for example, 50 mM sucrose, 100 mM K-phosphate buffer pH 7.4, 25 mM NaF, 0.1% (w/v) Triton X-100, 0.5 mM EDTA, 2 mM DTT, 0.25 mM pyridoxal phosphate. Reactions may then be terminated and analyzed by thin-layer chromatography to detect the formation of labeled fatty aldehydes and further metabolites. A modulating agent as described herein that alters SPL activity of an SPL polypeptide or variant thereof will result in a statistically significant increase or decrease in SPL activity as assayed herein as compared to the activity in the absence of said modulating agent.

Within certain embodiments, an in vitro assay for SPL activity may be performed using cellular extracts prepared from cells that express the polypeptide of interest. Preferably, in the absence of a gene encoding an SPL polypeptide, such cells do not produce a significant amount of endogenous SPL (i.e., a cellular extract should not contain a detectable increase in the level of SPL, as compared to buffer alone without extract). It has been found, within the context of the present invention, that yeast cells containing deletion of the SPL gene (BST1) are suitable for use in evaluating the SPL activity of a polypeptide. bst1Δ cells can be generated from S. cerevisiae using standard techniques, such as PCR, as described herein. A polypeptide to be tested for SPL activity may then be expressed in bst1Δ cells, and the level of SPL activity in an extract containing the polypeptide may be compared to that of an extract prepared from cells that do not express the polypeptide. For such a test, a polypeptide is preferably expressed on a high-copy yeast vector (such as pYES2, which is available from Invitrogen) yielding more than 20 copies of the gene per cell. In general, a polypeptide has SPL activity if, when expressed using such a vector in a bst1Δ cell, a cellular extract results in a two-fold increase in substrate degradation over the level observed for an extract prepared from cells not expressing the polypeptide.

A further test for SPL activity may be based upon functional complementation in the bst1Δ strain. It has been found, within the context of the present invention, that bst1Δ cells are highly sensitive to D-erythro-sphingosine. In particular, concentrations as low as 10 µM sphingosine completely inhibit the growth of bst1Δ cells. Such a level of sphingosine has no effect on the growth of wildtype cells. A polypeptide having SPL activity as provided above significantly diminishes (i.e., by at least two fold) the sphingosine sensitivity when expressed on a high-copy yeast vector yielding more than 20 copies of the gene per cell.

Assays to detect and measure sphingolipid intermediates include solid phase extraction. In certain embodiments, a Strata C18-E solid phase extraction column (50 mg/ml) (Phenomenex, Torrance, Calif.) can be used. In this context the column is initially wetted with 200 µl of methanol, followed by equilibration with 1 ml of solvent A. Fly extracts or LCB standards in solvent A may be applied to the equilibrated Strata C18-E column, followed by a wash with 1 ml of solvent A. A second wash of the column is performed by the addition of 600 µl of methanol. LCBs are then eluted from the column with 600 µl of methanol:10 mM ammonium acetate, 9:1 (v/v) and dried down in a speed vac. The skilled artisan would readily appreciate that the above parameters can be optimized and changed according to extracts and LCBs being used.

High-performance liquid chromatography analysis (HPLC) can also be used within the context of the present invention. HPLC can be carried out as described for example in Lester, R. L., and R. C. Dickson. 2001. *Anal. Biochem.* 298: 283-292. Briefly, LCBs are derivatized with, for example, ortho-phthalaldehyde (OPA) (Sigma St. Louis, Mo.) as described in Caligan, T. B., K. Peters J. Ou, E. Wang, J. Saba, and A. H. Jr. Merrill. 2000. *Anal. Biochem.* 281: 36-44. The OPA-derivatized LCBs are separated on a reverse-phase column with the mobile phase methanol/10 mM ammonium acetate, pH 5.2, 82:18 (v/v). Numerous reverse-phase columns are known in the art. Illustrative reverse-phase columns include but are not limited Luna RP-18, 3µ, 4.6×75 mm (Phenomenex, Torrance, Calif.). Flow rate is generally in the range of 1 ml/min. The skilled artisan would appreciate that flow rates can range from 0.2 ml/min to 3 ml/min and include any integer in between. Any number of HPLC systems can be used. Illustrative systems include a Beckman System Gold with a 125 solvent module. Fluorescent LCBs can be detected using a variety of systems. In one particular embodiment, fluorescent LCBs are detected and quantified using a Spectra-Physics fluorescence detector (SP 8410).

Mass Spectrometry may also used in the context of the present invention to detect and measure sphingolipid intermediates as described herein. In one particular embodiment, a Strata C18-E column-purified lipid extract from a desired source, and a $C_{14}$ sphingolipid standard are analyzed on a Micromass Quattro LCZ instrument following direct injection of 10 µl of sample. Mobile phase is generally in the range of 80 percent methanol containing 0.1 percent formic acid. The skilled artisan would appreciate that the mobile phase can be optimized. Flow rate is generally in the range of 0.2 ml/min. Structural confirmation of LCBs is obtained by positive electrospray ionization (ESI+) mass spectrometry. LCBs can be detected by precursor ion scans of structurally distinct ion fragments as described in the art, in particular as described in Sullards, M. C., and A. H. Jr. Merrill. 2001. *Sci. STKE.* 67: 1-11. Generally, 3.5 kV is applied to the capillary to start the spray and the collision-induced decomposition spectra, at a cone voltage of 20 V, are recorded at a collision energy of 15 eV with argon as collision gas. The skilled artisan would readily understand that any of the above parameters can change according to different samples and desired intermediates being measured as is known in the art.

Thus, LCBs can be identified through their patterns of collision-induced dissociation and precursor ion scans using positive ion electrospray mass spectrometry (ESI+) as described in Sullards, M. C., and A. H. Jr. Merrill. 2001. *Sci. STKE.* 67: 1-11. Based on their unique molecular structures, typical decomposition products arise from the loss of two water molecules. For example, the precursor ion spectrum of m/z 208 ($C_{14}$ sphingosine minus two water molecules) shows parents as m/z 244 ($C_{14}$ sphingosine) and m/z 226 ($C_{14}$ sphingosine minus one water molecule). In order to verify the existence of, for example $C_{14}$ dihydrosphingosine in *Drosophila melanogaster*, a Strata C18-E column purified lipid extract may be analyzed by ESI+. In addition, precursor ion scans of m/z 236 and m/z 238 identify $C_{16}$ sphingosine and $C_{16}$ dihydrosphingosine in a sample.

Lipid extracts for analysis in the context of the present invention can be prepared using any number of procedures known in the art. For example, to prepare *Drosophila melanogaster* lipid extracts, samples containing 25 mg of frozen intact fly material are placed in a homogenizer, for example a 7 ml Potter Elvehjem homogenizer. 20 µl of a mixture of internal LCB standards, (commercially available from, for example Matreya Inc., Pleasant Gap, Pa.) containing 250 to 500 pmol of each LCB are then added. Flies are homogenized in 2 ml of ice cold methanol/water, 1:1 (v/v) with a loose pestle followed by a tight pestle until it moved smoothly. Extracts are further homogenized with a tip sonicator (3×20 sec.) while on ice, then transferred to a glass tube and centrifuged at 1500×g for 10 minutes. Supernatants are recovered and dried down in a speed vac. Extracts are resuspended in 200 µl of methanol containing 0.1 M ammonium hydroxide, followed by vortexing, bath sonication and incubation at 37° C. for 1 hr to allow hydrolysis of esterified acyl chains. Following hydrolysis, the samples are cooled to room temperature, dried down in a speed vac and resuspended in 500 µl of methanol/water, 2:3 (v/v) containing 0.1% glacial acetic acid (solvent A). The skilled artisan would recognize that the above procedure may be modified accordingly to prepare lipid extracts from other samples including mammalian cells, yeast, bacteria or any other desired source of sphingolipid intermediate.

As noted herein, sphingolipid signaling contributes to specific pathways for biological signal transduction, including those associated with cell division, cell survival, apoptosis, proliferation and differentiation and "biological signal transduction pathways" or "inducible signaling pathways" in the context of the present invention include transient or stable associations or interactions among molecular components involved in the control of these and similar processes in cells. Depending on the particular sphingolipid signaling pathway of interest, such as a pathway induced by S-1-P binding to an EDG receptor and the like, an appropriate parameter for determining induction of such pathway may be selected. Signaling pathways associated with cell proliferation, there is available a variety of well known methodologies for quantifying proliferation, including, for example, incorporation of tritiated thymidine into cellular DNA, monitoring of detectable (e.g., fluorimetric or calorimetric) indicators of cellular respiratory activity, or cell counting, or the like. Similarly, in the cell biology arts there are known multiple techniques for assessing cell survival (e.g., vital dyes, metabolic indicators, etc.) and for determining apoptosis (e.g., annexin V binding, DNA fragmentation assays, caspase activation, etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), or altered cellular morphology, and the like, such that cellular responsiveness to a particular stimulus as provided herein can be readily identified to determine whether a particular cell responds to a particular sphingolipid signaling pathway.

Methods for Detecting Cancer

Within other aspects, the present invention provides methods and kits for diagnosing cancer and/or identifying individuals with a risk for developing cancer or with a risk for metastasis that is higher or lower than average. It has been found, within the context of the present invention, that certain human tumor cells contain an altered SK and SPL expression. In particular, decrease SPL expression was observed in certain tumor tissues as compared to corresponding normal tissue from the same individual, as described further in the Examples. Further, increase SK expression was observed in numerous tumor tissues as compared to corresponding normal tissue from the same invidivual. In other words, such polynucleotides or the proteins encoded by these polynucleotides, may be used as markers to indicate the presence or absence of a cancer in a patient.

Thus, one aspect of the present invention provides methods for detecting cancer by detecting alterations in expression level of pqlynucleotides encoding components of a sphingolipid metabolic and/or signaling pathway, in particular SK and SPL. In this regard, an individual demonstrating a statistically significant descrease in expression of SPL as compared to a control is considered to be afflicted with a cancer. In particular, a 50% to 60%, 61%, 62%, 63%, 64%, or 65% reduction in SPL expression in a cancer sample as compared to a corresponding normal tissue indicates the presence of cancer in a patient. In one embodiment, a 20%, 30%, 35%, 40%, 45%, 46%, 47%, 48%, or 49% reduction in SPL expression in a cancer sample as compared to a corresponding normal tissue indicates the presence of cancer in a patient. Likewise, an individual demonstrating a statistically significant increase in expression of SK as compared to a control is considered to be afflicted with a cancer. In particular, a 50% to 60%, 61%, 62%, 63%, 64%, or 65% increase in SK expression in a cancer sample as compared to a corresponding normal tissue indicates the presence of cancer in a patient. In one embodiment, a 20%, 30%, 35%, 40%, 45%, 46%, 47%, 48%, or 49% increase in SK expression in a cancer sample as compared to a corresponding normal tissue indicates the presence of cancer in a patient.

A cancer may be detected based on the level of mRNA encoding a protein involved in sphingolipid metabolism an/or signaling in a biological sample obtained from an individual suspected of having a cancer as compared to the level of mRNA detected in a biological sample obtained from a norml control subject known to be free of cancer. In certain embodiments, biological samples which contain cDNA pairs representing tumor tissue and corresponding normal tissue from the same patient can be used to determine the presence of cancer, for example as described in the examples. By utilizing sample (e.g., cell, tissue or biological fluid) pairs from one patient, differences between gene expression in tumor and normal tissue which might be due to person-to-person variability should not confound the interpretation of results. In certain other embodiments, samples may be obtained both from a subject suspected of having or being at risk for having cancer (e.g., a patient) and from a normal, control subject known to be free of the presence and/or risk for having cancer (e.g., a malignancy). Those familiar with the art will appreciate that for the described or characterized cancers, clinical criteria have been established for ascertaining when one or more signs or symptoms are apparent at levels upon which a suspicion that cancer is present may be based. A biological sample may include, but is not limited to, blood, sera, urine, cells or tissue of any type such as breast, lung, colon and the like, biopsy, tumor, lymph node, and the like. For example, at least two oligonucleotide primers may be employed in a polymerase chain reaction (PCR) based assay (e.g. RT-PCR, QC-RT-PCR, real-time PCR, etc.) to amplify a portion of a cDNA derived from a biological sample, wherein at least one of the oligonucleotide primers is specific for (i.e., hybridizes to specifically as determined using any one of a variety of techniques and controls known in the art) a polynucleotide encoding the protein. The amplified cDNA is then separated and detected using techniques well known in the art, such as gel electrophoresis. Generally, the oligonucleotide primers used in this context can be generated using guidelines known in the art. In particular, oligonucleotide primers are designed such that they are specific for a polynucleotide of interest. The PCR conditions used can be optimized in terms of temperature, annealing times, extension times and number of cycles depending on the oligonucleotide and the polynucleotide to be amplified. Such techniques are well know in the art and are described in for example, Mullis et al., *Cold Spring Harbor Symp. Quant. Biol.*, 51:263, 1987; Erlich ed., *PCR Technology*, Stockton Press, NY, 1989). Oligonucleotide primers can be anywhere from 8, 9, 10, 11, 12, 13, 14, 15, 16, 17, 18, 19, 20, 21, 22, 23, 24, 25, 26, 27, 28, 29, or 30 nucleotides in length. In certain embodiments, the oligonucleotide primers of the present invention are 35, 40, 45, 50, 55, or 60 nucleotides in length. In one embodiment, the oligonucleotides comprise a sequence described herein, such as those set forth in SEQ ID NOs:1, 3, 5, 7, 9, 12, 15, 17, and 22-27, or the complement thereof.

Similarly, oligonucleotide probes that specifically hybridize to a polynucleotide encoding a protein involved in sphingolipid metabolism an/or signaling may be used in a hybridization assay to detect the presence of polynucleotide encoding said protein in a biological sample as described herein (biological sample may include, but is not limited to, blood, tissue, biopsy, tumor, lymph node, and the like) obtained from a patient suspected of having cancer. Oligonucleotide probes can be of the lengths as described above. In certain embodiments, a probe may comprise the entire sequence as set forth in SEQ ID NOs: 1, 3, 5, 7, 9, 12, 15, 17, and 22-27, or the complement thereof.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A statistically significant increase or decrease in expression in several dilutions of the test patient sample as compared to the same dilutions of the non-cancerous sample is typically considered positive. Alternatively, levels of polynucleotide in corresonding normal tissues from the same test patient may be used as controls.

One aspect of the present invention provides methods for monitoring the progression of a cancer by detecting alterations in expression level of polynucleotides encoding components of a sphingolipid metabolic and/or signaling pathway, in particular SK and SPL. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected shows a statistically significant increase (such as for SK) or decrease (such as for SPL) over time. In contrast, the cancer is not progressing when the level of reactive polypeptide or polynucleotide either remains constant with time.

Specific alterations present in the genes encoding the polypeptides of the present invention involved in sphingolipid metabolism in other tumor cells, such as breast, colon, uterine, or other tumor cells, may be readily identified using standard techniques, such as PCR. Alterations that may be associated with a paticular tumor include amino acid deletions, insertions, substitutions and combinations thereof. Methods in which the presence or absence of such an alteration is determined may generally be used to detect cancer and to evaluate the prognosis for a patient known to be afflicted with cancer.

To detect an altered gene, any of a variety of well-known techniques may be used including, but not limited to, PCR and hybridization techniques, using polynucleotides of the present invention, or variants thereof. Any sample that may contain cancerous cells may be assayed. In general, suitable samples are tumor biopsies. Within a preferred embodiment, a sample is a breast tumor biopsy.

Kits for diagnosing or evaluating the prognosis of a cancer generally comprise reagents for use in the particular assay to be employed. In general, a kit of the present invention comprises one or more containers enclosing elements, such as primers, probes, reagents or buffers, to be used in an assay. For example, a kit may contain one or more polynucleotide primers or probes comprising at least 15 nucleotides complementary to a polynucleotide encoding a polypeptide involved in sphingolipid metabolism. In a preferred embodiment, said polypeptide is SK. In certain embodiments, the primers or probes comprise at least 10, 25, 30, 35, 40, 45, 50, 55, 60, 65, 70, 75, 80, 85, 90, 95 or 100 nucleotides, and preferably at least 150 or 200 nucleotides, complementary to an mRNA or to a polynucleotide encoding encoding a polypeptide involved in sphingolipid metabolism. Such probe(s) may be used to detect, for example, an altered SK gene by hybridization. For example, a kit may contain one probe that hybridizes to a region of an SK or SPL gene that is not generally altered in tumors (a control) and a second probe that hybridizes to a region commonly deleted in breast cancer. A sample that contains mRNA that hybridizes to the first probe, and not to the second (using standard techniques) contains an altered SK or SPL gene. Suitable control probes include probes that hybridize to a portion of the SK or SPL gene outside of a deleted region. Alternatively, a kit may comprise one or more primers for PCR analyses, which may be readily designed based upon the sequences provided herein by those of ordinary skill in the art. Optionally, a kit may further comprise one or more solutions, compounds or detection reagents for use within an assay as described above.

In a related aspect of the present invention, kits for detecting a polypeptide involved in sphingolipid metabolism are provided. Such kits may be designed for detecting the level of protein or nucleic acid encoding a protein, e.g. SK or SPL, within a sample, or may detect the level of SK or SPL activity as described herein. A kit for detecting the level of SK or SPL, or nucleic acid encoding SK or SPL, or other component of sphingolipid metabolism and/or signaling as described herein, typically contains a reagent that binds to the protein, DNA or RNA. To detect nucleic acid encoding SK, SPL or other protein, the reagent may be a nucleic acid probe or a PCR primer. To detect SK, SPL, or other protein, the reagent is typically an antibody. The kit may also contain a reporter group suitable for direct or indirect detection of the reagent as described above.

Generation of Mutant and Transgenic *Drosophila melanogaster*

The invention further provides mutant and/or transgenic *Drosophila melanogaster*. In one embodiment, a mutant *Drosophila melanogaster* comprises a P-element transposon insertion in a coding region of a gene encoding a component of a sphingolipid metabolic and/or signaling pathway. In certain embodiments, the P-element transposon insertion results in an altered level of at least one sphingolipid intermediate as described herein. In a further embodiment, the P-element transposon results in altered activity level of at least one sphingolipid pathway component as described herein. In further embodiments, the mutant *Drosophila melanogaster* of the present invention comprise a P-element insertion in the coding region of more than one gene encoding a component of a sphingolipid metabolic and/or signaling pathway. Mutants can be generated comprising any number of insertions in any number of genes encoding components of a sphingolipid metabolic and/or signaling pathway. In certain embodiments, 1, 2, 3, 4, or 5 genes encoding components of a spphingolipid metabolic and/or signaling pathway contain P-element insertions.

Illustrative lines of *Drosophila melanogaster* inlcude Wild type Canton S, lace$^2$/lace$^{05305}$ and Sply mutant lines. Flies can be obtained from the *Drosophila* Genome Project Stock Center (Bloomington, Ind.). General fly husbandry is known in the art and is described for example, in Ashburner, M and Roote J, 2000. Laboratory culture of *Drosophila, Drosophila Protocols* 585-600. Analysis of *Drosophila melanogaster* anatomical structures may be carried out by the skilled artisan using a variety of techniques in the art, including those described in (O'Donnell, P. T. and Bernstein, S. I. (1988). *J Cell Biol* 107, 2601-12.; Fyrberg, E. A., Bernstein, S. I. and VijayRaghavan, K. (1994). *Methods Cell Biol* 44, 237-58.).

The invention further provides *Drosophila melanogaster* mutants that exhibit a flightless phenotype, where the phenotype results from the disruption of an endogenous gene involved in sphingolipid metabolism and/or signaling, for example, the SPL, SK, SPT, or other gene as described in detail herein. In one embodiment, flightless phenotype is meant that the subject non-mammalian organism models spontaneously develop a reduced number of muscle fibers comprising the dorsal longitudinal muscles (DLM) and have compensatory hypertrophy in the remaining fibers. Analysis of DLM formation is carried using markers specific for different stages of differentiation, as well as GFP markers which distinguish myoblasts emerging from imaginal discs versus larval template muscles. Expression of a series of markers of muscle development can also be used in evaluating embryonic muscle differentiation. For example, Dmef2 is expressed in migrating myoblasts, allowing analysis of early steps in embryonic myogenesis. These myoblasts divide, forming two myocytes that express αMHC and ultimately fuse to form embryonic muscles. Thus, by evaluating αMHC, embryonic muscle fusion can be evaluated.

In certain aspects, the *Drosophila melanogaster* mutant of the present invention may also demonstrate abnormal developmental patterning of thoracic muscles of the T2 segment. Identification of *Drosophila melanogaster* anatomy is readily carried out by the skilled artisan using a variety of techniques knows in the art, including those described in the Examples herein, or, for example, Developmental Biology, 6th Edition, Scott F. Gilbert, Sinauer Associates, Inc., Sunderland, Mass. In a preferred embodiment, the above phenotypes result in an inability to fly or otherwise reduced flight performance as described in the Examples or as described in Vigoreaux, et al., 1993 J. Cell Biol. May; 121(3):587-98. The subject *Drosophila melanogaster*, within a preferred embodiment, demonstrate altered activity of at least one component of a sphingolipid metabolic and/or signaling pathway, such as SPL, SK, SPT, ceramidase or other component as described herein. In a particularly illustrative embodiment, said *Drosophila melanogaster* has decreased activity of endogenous SPL and/or increased or decreased activity of SK.

In a preferred embodiment, the strain contains a mutation in any one or more of the genes encoding a component of the sphingolipid metabolism and/or signaling, such as SPL, SK, SPT, S-1-PP, ceramidase, or any combination thereof. In a further embodiment of the present invention the *D. melanogaster* strain are heterozygous for a P-element transposon which sits in any region of the gene encoding the SPL protein set forth in SEQ ID NO:16. In a certain embodiment, the P-element transposon sits in a regulatory region of the gene. In a preferred embodiment, the flies are homozygous insertional mutants in the coding region of the gene encoding the SPL protein set forth in SEQ ID NO:16. In a further embodiment of the present invention the *D. melanogaster* strain are heterozygous for a P-element transposon which sits in the coding region of the gene encoding the SK protein set forth in any one of or all of SEQ ID NOs:18, 19, 20, 28, and 29. In a preferred embodiment, the flies are homozygous insertional mutants in the coding region of the gene encoding the SK protein set forth in any one or more of SEQ ID NOs:18, 19, 20, 28, and 29. In yet a further embodiment of the present invention, the homozygous mutant strain of fly has a flightless phenotype. In certain embodiments, the mutant flies have a reduced number of muscle fibers comprising the dorsal longitudinal muscles and have compensatory hypertrophy in the remaining fibers. In certain aspects, the mutant flies of the present invention may also demonstrate abnormal developmental patterning of thoracic muscles of the T2 segment, for example as described herein in the Examples. Identification of normal and abnormal anatomy of the *Drosophila melanogaster* can be carried out using techniques known to the skilled artisan and described herein, and for example, in Developmental Biology, 6th Edition, Scott F. Gilbert, Sinauer Associates, Inc., Sunderland, Mass. Illustrative mutant flies have altered sphingolipid metabolism.

Flies heterozygous for a P-element transposon which sits in a gene encoding a component of sphingolipid metabolism and/or signaling may be obtained from the *Drosophila* Genome Project. Homozygous insertional mutants can be made, using techniques known in the art, by genetically crossing and evaluating progeny for the presence of homozygous insertional mutants (for example, based on presence of rosy eye color, encoded by a recessive marker carried on the P-element). Expression of the SPL or other gene involved in sphingolipid metabolism, can be evaluated using any number of assays known to the skilled artisan, for example, by Northern blot analysis. To determine the SPL function of each genotype, +/+, +/− and −/− flies may be homogenized using standard techniques and whole extracts can be assayed for SPL activity using assays as described herein. The transposon can be mobilized by crossing SPL mutant flies with flies carrying an actively transcribed transposase gene, which should cause the P-element to be excised in the chromosomes of both somatic cells and in the germline. Germline transposon loss is heritable and can be identified in progeny by virtue of eye color or other relevant marker. Progeny which lost both the transposase gene and the P-element can then be isolated and the restored allele can be homozygosed.

Mutations in *Drosophila melanogaster* as described herein which permanently block expression of a functional protein can be created in several ways, such as with P-element transposon insertions or chemical or radiation induced mutagenesis. Exemplary strains of mutant flies are available through the *Drosophila* Genome Project, at the University of California at Berkeley (Adams, M. et al 2000. The genome sequence of *Drosophila melanogaster*. *Science*. 287:2185-2195.). Alternatively, insertional mutant of interest may be obtained by using local hop strategies essentially as described in Tower, J. et al (Tower, J., et al. 1993. Preferential transposition of *Drosophila* P elements to nearby chromosomal sites. *Genetics*. 133:347-359.). Transposons can be mobilized by crossing in a transposase gene, followed by crossing the transposase back out (reintroducing genetic stability). Mutant flies can be identified using techniques know to those of skill in the art. For example, mutant flies can be identified by probing Southern blots prepared from extracts from flies generated in the screen using the target gene as probe. Subsequently, crosses can be performed to introduce a mutant allele of interest, (e.g. SPL, SK, SPT or other component of sphingolipid metabolism and/or signaling) and generate homozygosity at both mutant alleles (e.g. SPL and new transposon integration sites). Mutants can be screened for a phenotype of interest, for example the ability to restore flight to an SPL mutant when the mutated allele is homozygous (predicting a recessive phenotype).

In one aspect of the present invention, fly genetic manipulation may entail mating or "crossing" of flies and selection for or against progeny expressing various phenotypic markers. Exemplary techniques for fly genetic manipulation of the present invention are know in the art and are described, for example in, Ashburner, M., and J. Roote. 2000. Laboratory culture of *Drosophila*. In *Drosophila* Protocols. W. Sullivan, M. Ashbumer, and R. Hawley, editors. Cold Spring Harbor Laboratory Press, Cold Spring Harbor, N.Y. 585-600. Phenotypic markers may be used to identify the inheritance of chromosomes, engineered transposable elements, or transposase genes used to facilitate their mobilization. Marker mutations affecting eye color, bristle shape, wing morphology and cuticle pigmentation, for example, may be employed in the crosses for the mutant flies of the present invention. Within one aspect of the present invention, it may be desirable to select the individuals which contain a collection of markers indicating the desired genotype. In another aspect of the present invention, balancer chromosomes may be used to create the ability to identify recessive mutations present in the heterozygous state. Balancer chromosomes may be employed to prevent homologous recombination during meiotic prophase in females. The presence of both dominant and recessive lethal markers allows one to determine the presence or absence of the balancer chromosomes and simultaneously to follow the homologous chromosomes, which may themselves not contain a dominant marker. One particularly illustrative cross of the present invention is to eliminate the P-element insertion in the Drosophila melanogaster SPL gene and establish phenotypic reversion, as described herein in the Examples.

The genetics required to create the mutant flies described herein may involve several successive steps. For example, lines homozygous for the Sply$^{05091}$ allele and the lace$^{05305}$ allele can to be generated by meiotic recombination. Sply$^{05091}$ and lace$^{05305}$ mutations can be introduced in trans and balanced in the next generation. Flies carrying the lace$^{05305}$ allele can be selected by the presence of w$^+$. Presence of Sply$^{05091}$ and other mutation of the present invention can be verified by PCR. Similar strategies are employed to create other strategic crosses envisioned by the present invention. For example, lines containing null alleles for both SK genes will be generated. Lines containing null alleles for one or more components of a sphingolipid metabolic and/or signaling pathway are envisioned by the present invention. For example, lines containing null alleles for SK and SPL are envisioned. Lines containing null alleles for SPT and SK are envisioned as are other double, triple, and quadruple mutant lines of virtually any component in a sphingolipid metabolic and/or signaling pathway.

Selective markers to allow for selection of mutant flies is provided for in the present invention. Exemplary selective markers of the present invention may comprise a wild type rosy (ry$^+$) allele carried on the transposon to allow for selection for or against the stable transposon. Introduction of an active transposase is selected for by presence of, for example, the dominant marker, Stubble (short bristle phenotype) in the first cross, and is selected against to identify progeny which have lost the transposase, restoring genetic stability in the second cross. Other illustrative markers include Curly O (CyO) which is lethal when present in two copies, allowing selection for heterozygotes containing the CyO balancer and another allele of interest originally containing the transposon (e.g., SPL). By selecting against rosy eye color, progeny in which the transposon has been excised from the locus of interest, e.g., SPL, SK, or other components of sphingolipid metabolism and/or signaling can be identified. Expansion of this "reverted" allele in the population can be achieved in the third cross, and the desired allele can be homozygosed in the final cross, to determine whether restoration of the intact allele of interest, for example SPL and/or SK, is associated with a desired phenotype of interest, such as restoration of flight.

Transgenic Drosophila melanogaster are also provided in the present invention. Relevant methods of preparing transgenic Drosophila melanogaster are disclosed in: Spradling, A. C., and Rubin, G. M. (1982). Science 218, 341-347; Brand & Perrimon, Development (1993) 118: 401-415; and Phelps & Brand, Methods (April 1998) 14:367-379. See also, Spradling A C, P Element Mediated Transfornmation in Drosophila: A Practical Approach (ed. D. D. Roberts, IRL Press, Oxford)(1986) pp 175-179; and U.S. Pat. No. 6,316,690.

The subject transgenic flies can be prepared using any convenient protocol that provides for stable integration of the transgene in to the fly genome in a manner sufficient to provide for the requisite spatial expression of the transgene. A number of different strategies can be employed to obtain the integration of the transgene with the requisite expression pattern. Generally, methods of producing the subject transgenic flies involve stable integration of the transgene into the fly genome. Stable integration is achieved by first introducing the transgene into a cell or cells of the fly, e.g. a fly embryo. The transgene is generally present on a suitable vector, such as a plasmid. Transgene introduction may be accomplished using any convenient protocol, where suitable protocols include: electroporation, microinjection, vesicle delivery, e.g. liposome delivery vehicles, and the like. Following introduction of the transgene into the cell(s), the transgene is stably integrated into the genome of the cell. Stable integration may be either site specific or random, but is generally random.

Where integration is random, the transgene is typically integrated with the use of transposase. In such embodiments, the transgene is introduced into the cell(s) within a vector that includes the requisite P element, terminal 31 base pair inverted repeats. Where the cell into which the transgene is to be integrated does not comprise an endogenous transposase, a vector encoding a transposase is also introduced into the cell, e.g. a helper plasmid comprising a transposase gene, such as pTURBO (as disclosed in Steller & Pirrotta, "P Transposons Controlled by the Heat Shock Promoter," Mol. Cell. Biol. (1986) 6:1640-1649). Methods of random integration of transgenes into the genome of a target Drosophila melanogaster cell(s) are disclosed in U.S. Pat. No. 4,670,388.

In those embodiments in which the transgene is stably integrated in a random fashion into the fly genome, means are also provided for selectively expressing the transgene at the appropriate time during development of the fly. In other words, means are provided for obtaining targeted expression of the transgene. To obtain the desired targeted expression of the randomly integrated transgene, integration of particular promoter upstream of the transgene, as a single unit in the P element vector may be employed. Alternatively, a transactivator that mediates expression of the transgene may be employed. Of particular interest is the GAL4 system described in Brand & Perrimon, supra.

In one aspect of the present invention, transgenic flies can be created using P-elements to express, overexpress or misexpress proteins of interest, such as SPL, SK, SPT, S-1-PP, ceramidase, or any combination thereof. The transgenes for use in the context of the present invention may include SPL, SK, SPT, S-1-PP, ceramidase, or any other protein involved in sphingolipid metabolism and/or signaling from human, mouse, yeast, or C. elegans. In further embodiments of the present invention, the transgene of interest comprises a polynucleotide encoding a fusion protein. For example, a polynucleotide encoding a polypeptide component of the sphingolipid metabolic pathway, such as SK, SPL, SPT, S-1-PP and the like, can be engineered to fuse the protein of interest to a marker protein such as GFP for use as a transgene in the context of this invention. The skilled artisan would readily recognize that any number of marker proteins can be used in fusion proteins of the present invention.

In one embodiment of the invention, GAL4-mediated ectopic gene expression is employed, essentially as described (van Roessel, P., and A. Brand. 2000. GAL4-mediated ectopic gene expression in Drosophila. In Drosophila Protocols. W. Sullivan, M. Ashburner, and R. Hawley, editors. Cold Spring Harbor Laboratory Press, Cold Spring Harbor, N.Y. 439-448.). Other illustrative inducible promoter may be used as well, such as those described in Rubin, G, Hong L, Brokstein P, Evans-Holm M, Frise E, Stapleton M and Harvey D, 2000. A Drosophila complementary DNA resource, Science 287: 2222-2224. The GAL4 protein is a yeast transcription factor capable of activating transcription of Drosophila melanogaster genes which have been engineered to contain upstream sequences recognized by the GAL4 protein. Various mutants can be created with a gene of interest expressed in specific tissue distributions, a construct containing the gene of interest (reporter) under regulation of a GAL4 containing promoter is introduced into embryos, and a genetic marker allows identification of progeny containing this construct. Illustrative GAL4 containing promoters include, but are not limited to, pUAS. The skilled artisan would readily appreciate that other inducible systems can be used in the context of the present invention. The use of embryos of a strain containing an active P-transposase increases the efficiency of transgene integration, although many of the embryos die. These progeny can then be crossed to various available lines containing GAL4 transgenes (driver) expressed under control of tissue-specific promoters. In one embodiment of the present invention, GAL4 driver constructs which allow expression during embryogenesis may be used.

Various methods to identify the etiology of the SPL, SPT and other mutant phenotypes are known to those of skill in the art and are also provided herein. The present invention provides for mutant *Drosophila melanogaster* with defective or overexpressed SPL, SK, SPT and S-1-P phosphatase genes. In a particular embodiment, abnormal sphingolipid metabolism is a phenotype of the mutant *Drosophila melanogaster* of the present invention. In a further embodiment, the abnormal sphingolipid metabolism affects developmental programs in the mutant flies. In certain embodiments, the mutant and/or transgenic *Drosophila melanogaster* of the present invention develop one or more tumors. Tumors can be identified and measured using a variety of techniques known to the skilled artisan. Particularly illustrative techniques are described in, for example, De Lorenzo, C., B. M. Mechler, and P. J. Bryant. 1999. *Cancer Metastasis Rev.* 18:295-311.; Watson, K., R. Justice, and P. Bryant. 1994. *J Cell Sci Supp.* 18:19-33.; Gateff, E., and H. Schneiderman. 1967. *Amer Zool.* 7:760.; Gateff, E. 1994. *Int J Dev Biol.* 4:565-590, or any references cited therein.

Quantitative analysis and characterization of sphingolipids in normal and mutant and/or transgenic flies throughout development may be carried out using any number of techniques known to the skilled artisan. Such techniques are described in, for example, Ashbumer, M., and J. Roote. 2000, Laboratory culture of *Drosophila*. In *Drosophila* Protocols, W. Sullivan, M. Ashburner, and R. Hawley, editors, Cold Spring Harbor Laboratory Press, Cold Spring Harbor, N.Y. Pp. 585-600; Blair, S. 2000, Imaginal discs, In *Drosophila* Protocols, W. Sullivan, M. Ashburner, and R. Hawley, editors. Cold Spring Harbor Laboratory Press, Cold Spring Harbor, N.Y. 159-175, and Stern, D., and E. Sucena. 2000. Preparation of larval and adult cuticles for light microscopy. In *Drosophila* Protocols. W. Sullivan, M. Ashbumer, and R. Hawley, editors. Cold Spring Harbor Laboratory Press, Cold Spring Harbor, N.Y. 601-616.

Further, identification of lipids which are not within normal concentration ranges in various mutants of the present invention, especially those demonstrating developmental defects, can be done using standard techniques. In certain embodiments, the embryonic, larval, pupal and adult stages of development of *Drosophila melanogaster* models harboring single or multiple sphingolipid metabolic defects are examined using techniques described herein, in particular in the Examples. Light and electron microscopy and in situ hybridization with appropriate tissue-specific markers of differentiation should identify both gross and subtle defects associated with altered sphingolipid metabolism.

Within further aspects, the present invention provides other transgenic organisms in which sphingolipid metabolism is altered, compared to wild-type organisms. Within the context of the present invention, organisms may include but are not limited to mice, rats, and *C. elegans*, and other species of *Drosophila*. Such organisms may contain an alteration, insertion or deletion in an endogenous gene involved in sphingolipid metabolism and/or signaling, or may contain DNA encoding a modulating agent that modulates expression or activity of a gene involved in sphingolipid metabolism. In one embodiment the altered endogenous gene comprises SK. In certain aspects, such organisms may contain DNA encoding a modulating agent that increases expression or activity of an SK or an SPL gene. Transgenic organisms may be generated using techniques that are known to those of ordinary skill in the art. For example, a transgenic organism containing an insertion or deletion in the coding region for the SK or SPL gene may be generated from embryonic stem cells, using standard techniques. Such stem cells may be generated by first identifying the full genomic sequence of the gene encoding the SK or SPL, and then creating an insertion or deletion in the coding region in embryonic stem cells. Alternatively, appropriate genetically altered embryonic stem cells may be identified from a bank. Using the altered stem cells, hybrid organisms may be generated with one normal SK or SPL gene and one marked, abnormal gene. These hybrids may be mated, and homozygous progeny identified.

Transgenic organisms may be used for a variety of purposes, which will be apparent to those of ordinary skill in the art. For example, such organisms may be used to prepare cell lines from different tissues, using well known techniques. Such cell lines may be used, for example, to evaluate the effect of the alteration, and to test various candidate modulators.

In addition to their use as animal models for screening candidate therapeutic agents, the subject mutant and transgenic flies also find use in the identification of gene targets involved in sphingolipid metabolism and/or signaling, i.e. genes whose expression can be beneficially modulated to treat diseases associated with sphingolipid metabolism and/or signaling. Gene based therapies can be identified by doing traditional enhancer/suppressor analyses in the subject mutant and transgenic flies. In these analyses, genes in the subject mutant and/or transgenic flies are mutated to identify ones that either exacerbate or alleviate the mutant or transgenic phenotype. Methods of mutating genes and carrying out enhancer/suppressor analyses are well known to those of skill in the art (Hays, T S et al., Molecular and Cellular Biology (March 1989) 9(3):875-84; Deuring, R; Robertson, B; Prout, M; and Fuller, M T. Mol. Cell. Biol., 1989 9:875-84.; Fuller, M T et al., Cell Mot. Cyto. (1989) 14 :128-35; Rottgen G, Wagner T, Hinz U Mol. Gen. Genet. 1998 257:442-51).

Genes that mutate to enhance the phenotype of mutant and/or transgenic flies of the present invention in a recessive manner yield potential protein therapeutics for conditions associated with sphingolipid metabolism and/or signaling, since elevating the normal gene product level of such genes potentially alleviates such condition. Genes that mutate to suppress the adult onset neurodegeneration phenotype in a recessive manner yield gene targets for disruption to alleviate the diseases associated with sphingolipid metabolism or signaling, where disruption of these genes can be achieved using a variety of methods, ranging from deleting the DNA for the target gene to inhibiting its transcription, translation, or protein activity. For screening candidate agents, small molecule antagonists to these genes can be constructed and evaluated for efficacy in the fly model through oral administration. Alternatively, large molecular antagonists can be delivered by gene therapy, as described infra.

Methods of Use and Pharmaceutical Compositions

The agents that modulates a component of sphingolipid metabolism and/or signaling and/or a sphingolipid intermediate as described herein are useful for the detection, diagnosis and treatment of any disease associated with altered sphingolipid metabolism and/or signaling. Illustrative diseases include but are not limited to a variety of cancers (e.g. breast, colon, uterus, stomach, ovary, lung, kidney and rectum cancer), diseases that result from muscle developmental defects, cardiomyopathy, and hereditary sensory neuropathy type 1 and the sphingolipidoses. Thus, the compositions of the present invention may be used to inhibit the development of cancer, metastasis, or both development of cancer and metastasis in an individual afflicted with a cancer.

The compositions of the present invention may be administered to an individual afflicted with a disesase associated with altered sphingolipid metabolism and/or signaling. For in vivo use for the treatment of human disease, an agent that modulates a component of sphingolipid metabolism and/or signaling and/or a sphingolipid intermediate as described herein is generally incorporated into a pharmaceutical composition prior to administration. A pharmaceutical composition comprises one or more modulating agents in combination with a physiologically acceptable carrier or excipient. To prepare a pharmaceutical composition, an effective amount of one or more modulating agents is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerine, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients (including other anti-cancer agents) and/or suitable excipients such as salts, buffers and stabilizers may, but need not, be present within the composition.

A modulating agent may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Administration may be achieved by a variety of different routes, including oral, parenteral, nasal, intravenous, intradermal, subcutaneous or topical. Preferred modes of administration depend upon the nature of the condition to be treated or prevented. An amount that, following administration, inhibits, prevents or delays the progression and/or metastasis of a cancer is considered effective. Preferably, the amount administered is sufficient to result in regression, as indicated by 50% mass or by scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

In certain embodiments, particularly where the modulating agent comprises a polynucleotide, a polynucleotide encoding a modulating agent may be administered. Such a polynucleotide may be present in a pharmaceutical composition within any of a variety of delivery systems known to those of ordinary skill in the art, including nucleic acid, bacterial and viral expression systems, and colloidal dispersion systems such as liposomes. Appropriate nucleic acid expression systems contain the necessary DNA sequences for expression in the patient (such as a suitable promoter and terminating signal, as described above). The DNA may also be "naked," as described, for example, in Ulmer et al., Science 259:1745-49, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Another delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preparation and use of liposomes is well known to those of ordinary skill in the art.

Within certain aspects of the present invention, one or more modulating agents may be used to modulate expression and/or activity of a component of a sphingolipid metabolic and/or signaling pathway, in a cell or in a mammal. In vitro, a polypeptide that is involved in sphingolipid metabolism may be contacted with a modulating agent that increases or decreases it's activity (e.g., certain antibodies, chemicals, or small molecules). In one embodiment, activity can be measured through levels of sphingolipid intermediates using assays as described herein. In a further embodiment, the modulating agent increases or decreases activity of a component of sphingolipid metabolism and/or signaling and can be assayed using methods as described herein. For use within a cell or a mammal, such modulation may be achieved by contacting a target cell with an effective amount of a modulating agent, as described herein. Administration to a mammal may generally be achieved as described herein.

As noted above, altered expression and/or activity provides a method for inhibiting the growth (i.e., proliferation) of a cancer cell, either in culture or in a mammal afflicted with cancer. In vivo, such alteration or modulation may also be used to inhibit cancer development, progression and/or metastasis. Accordingly, one or more modulating agents as provided herein may be administered as described above to a mammal in need of anti-cancer therapy. Patients that may benefit from administration of a modulating agent are those afflicted with cancer. Such patients may be identified based on standard criteria that are well known in the art. Within preferred embodiments, a patient is afflicted with breast cancer, as identified based on tissue biopsy and microscopic evaluation, using techniques well known in the art. In particular, patients whose tumor cells contain a tissue-specific deletion and/or alteration within an endogenous gene encoding a component of a sphingolipid metabolic and/or signaling pathway may benefit from administration of a modulating agent, as provided herein. In further embodiments, the patient may be afflicted with cancer of the breast, uterus, stomach, ovary, lung, kidney and rectum.

The following Examples are offered by way of illustration and not by way of limitation.

EXAMPLES

Materials and Methods used in some of the Examples below are described herein as follows. (see also D. Herr, H. Fyrst, et al. 2003, Development).

*Saccharomyces cerevisiae* strains and growth conditions: Wild type yeast used herein were of strain JK9-3d (leu2-3,112 ura3-52 rme1 trp1 his4 HMLa) (Heitman, J., Movva, N. R., Hiestand, P. C. and Hall, M. N. (1991). FK 506-binding protein proline rotamase is a target for the immunosuppressive agent FK 506 in *Saccharomyces cerevisiae*. *Proc Natl Acad Sci USA* 88, 1948-52.) The yeast strain JSK386 (dpl1Δ) is an isogenic derivative of strain JK9-3d in which the DPL1 gene has been replaced by a G418-resistant marker (Kim, S., Fyrst, H. and Saba, J. (2000). Accumulation of phosphorylated sphingoid long chain bases results in cell growth inhibition in *Saccharomyces cerevisiae*. *Genetics* 156, 1519-29.). Strains JS204 and JS205 are derivatives of JSK386 which contain the *Drosophila melanogaster* ESTs LP04413 and GH3783 respectively in expression vector, pYES2 (Invitrogen, Inc., Carlsbad, Calif.). pYES2 is a yeast expression vector containing the URA3 gene (which provides transformants the ability to grow in media without uracil), and an Ampicillin resistance marker and origin of replication functional in *Escherischia coli*. Genes expressed using this system are regulated under the control of the GAL1,10 promoter, which allows expression in the presence of galactose and not in the presence of glucose. Cells were grown in minimal or uracil⁻ media containing either 20 g glucose or galactose per liter, as indicated.

Functional complementation in yeast: Strains of interest were grown to saturation in liquid culture for 2-3 days. They were then resuspended in minimal medium, placed in the first row of a 96-well plate and diluted serially from 1:2 to 1:4000 across the plate. The cultures were normalized for $O.D._{600}=2$ and template inoculated onto a control plate and a plate containing 50 μM sphingosine, obtained from Sigma Chemical Company (St. Louis, Mo.). Sphingosine enriched plates were made with minimal media containing 0.0015% NP40 and 50 pM D-erythro-sphingosine. At this concentration of NP40, no effects on cell viability are observed. Plates were incubated at 30° C. for two days and assessed visually for differences in growth.

SPL assays: SPL assays of yeast extracts from strains expressing *Drosophila melanogaster* sequences LP04413 and GH3783 were performed as previously described using a [$^3$H] labeled $C_{18}$ dihydrosphingosine substrate, obtained from American Radiolabeled Chemicals, Inc. (St. Louis, Mo.) (Saba, J. D., Nara, F., Bielawska, A., Garrett, S. and Hannun, Y. A. (1997). The BST1 gene of *Saccharomyces cerevisiae* is the sphingosine-1-phosphate lyase. *J Biol Chem* 272, 26087-26090. Van Veldhoven, P. P. and Mannaerts, G. P. (1991). Subcellular localization and membrane topology of sphingosine-1-phosphate lyase in rat liver. *J Biol Chem* 266, 12502-7.). In this method, SPL activity is measured by determining the conversion of radiolabeled $C_{18}$-dihydrosphingosine substrate to long chain aldehyde product. To assess the ability of homozygous Sply$^{05091}$ versus wild type flies to degrade endogenous LCBPs, an HPLC method was developed and employed to examine extracts of wild type and homozygous Sply$^{05091}$ adults. Endogenous LCBPs were first isolated as described under 'Analysis of *Drosophila melanogaster* Sphingolipids,' and the lipid extract from 15 mg of homozygous Sply$^{05091}$ flies were dried down using nitrogen gas. Lipids were resuspended in SPL reaction buffer and incubated for various time points @ 37° C. Lipids were reisolated, derivatized with o-phthalaldehyde and analyzed by HPLC, as described below. Activity was determined by measuring the percent degradation of endogenous LCBPs in comparison to standards incubated in the absence of protein extracts.

Developmental expression of Sply: For Northern analysis, full-length probes were labeled by random priming with [$\gamma$-$^{32}$P] dGTP. Hybridization was carried out under standard conditions against an RNA blot prepared from total RNA of flies harvested at different stages of development (embryos at hours 0-4, 4-8, 8-12, 12-24, larval instars $1^{st}$, $2^{nd}$, $3^{rd}$ and adults). RpL32 is a constitutively expressed ribosomal gene used as a loading control.

In situ hybridization was performed with a digoxygenin-labeled probe (Roche cat# 1 175 025) and hybridized to fixed embryos at various stages essentially as described (Tautz, D. and Pfeifle, C. (1989). *Chromosoma* 98, 81-5.).

Analysis of *Drosophila* sphingolipids: 100 mg of flies were homogenized in 6 ml of ice cold methanol/water 1:1 (vol:vol) with a Potter-Elvehjem homogenizer with a loose pestle followed by a tight pestle until the pestle moved smoothly. Extract was further homogenized by tip sonication for 3 times 20 sec. Extract was spun at low speed and supernatant was removed and dried down in speed vac. Extract was resuspended in 500 μl of methanol containing 0.1M ammonium hydroxide and incubated for 1 hour at 37° C. Following incubation the extract was dried down in speed vac. Extract was resuspended in 500 μl of 50% methanol containing 0.1% glacial acetic acid and applied to a C18E STRATA solid phase extraction column. C18E STRATA column was washed with 50% methanol containing 0.1% glacial acetic acid followed by a wash with 100% methanol containing 0.1% glacial acetic acid. Lipids of interest were eluted with methanol/10 mM ammonium acetate, 9:1 (vol:vol). Lipids were dried down in speed vac. and o-pthaladehyde labeled for HPLC analysis as previously described (Kim, S., Fyrst, H. and Saba, J. (2000). *Genetics* 156, 1519-29.).

Lethal phase analysis: 100 embryos from the indicated lines were collected and observed at each developmental stage. Viability is expressed as the percentage of flies that survived through the indicated stage.

Adult flight performance: 2-7 day old adult flies were released into a top-lit Plexiglas chamber. Flight behavior was scored as follows: upward flight=3, lateral flight=2, downward flight=1, flightless=0 (Vigoreaux, et al., 1993 *J. Cell Biol*. May; 121(3):587-98). Average flight scores were compared using a two-tailed student t-test.

Adult and larval microscopy: Preparation of tissue, staining, mounting and visualization was performed using standard techniques (Sullivan, W., Ashbumer, M. and Hawley, R. S. (2000). *Drosophila* protocols. Cold Spring Harbor, N.Y.: Cold Spring Harbor Laboratory Press.). Thoraces from adult flies were dissected, fixed with formaldehyde and osmium tetroxide, and embedded in EPON. These blocks were then cut into 1 μm thick sections, stained with methylene blue and azure II, and visualized with a Lieca DMIRBE microscope.

Larvae were filleted during the third instar, pinned with the dorsal cuticle down, and eviscerated to allow an unobstructed view of the body wall muscles. The tissue was fixed with 4% formaldehyde, permeabilized in 100% acetone, and stained with fluorescein-conjugated phalloidin. (Molecular Probes cat#F-432).

Electron microscopic analysis of DLMs was performed on adults essentially as described (O'Donnell, P. T. and Bernstein, S. I. (1988). *J Cell Biol* 107, 2601-12.).

Hemithoraces were visualized essentially as described (Fyrberg, E. A., Bernstein, S. I. and VijayRaghavan, K. (1994). *Methods Cell Biol* 44, 237-58.). Briefly, adult flies were frozen in liquid nitrogen, bisected with a razor blade, and dehydrated in an ethanol series. The cuticles were then cleared with methyl salicylate to allow visualization of the muscles with a Lieca DMIRBE microscope under polarized light.

Fluorescent microscopy: 0-24 hour embryos were prepared and fixed using standard techniques (Rubin Manual) and stained with the indicated primary antibody or assayed for apoptosis using a TUNEL-based staining method (In situ cell death detection kit, Roche 1 684 795). Incorporation of fluorescein was assessed with a Leica DMIRBE epifluorescence microscope and an upright Leica TCS-NT confocal laser scanning microscope.

Antibodies and fluorescent reagents were as follows: polyclonal rabbit anti-*Drosophila* myosin heavy chain (Kiehart, D. P. and Feghali, R. (1986). Cytoplasmic myosin from *Drosophila melanogaster. J Cell Biol* 103, 1517-25.) 1:1,000. Polyclonal rabbit anti-DMEF2 (Lilly et al., 1995) 1:10,000. Secondary antibody was a fluorescein-conjugated goat anti-rabbit IgG (Jackson ImmunoResearch Laboratories, Inc.) 1:1,000.

Genetics: The precise excision of the ry$^+$ PZ P-element was performed by introducing transposase allele Δ2-3 into insertion line BL-11393. In the subsequent generation the transposase was removed and the second chromosome was balanced over CyO. Offspring of these flies that lacked the P-element were selected by scoring for loss of ry$^+$. Homozygous lines were generated, assayed for restoration of flight behavior, and assessed for precise excision by PCR if indicated. Lines homozygous for the Sply$^{05091}$ allele the lace$^{k05305}$ allele were generated by meiotic recombination. Sply$^{05091}$ and lace$^{k05305}$ mutations were introduced in trans and balanced in the next generation. Flies carrying the lace$^{k05305}$ allele were selected by presence of w$^+$. Presence of Sply$^{05091}$ was verified by PCR.

Preparation of transgenic *Drosophila melanogaster*: Relevant methods of preparing transgenic *Drosophila melanogaster* are disclosed in: Spradling, A. C., and Rubin, G. M. (1982). Science 218, 341-347; Brand & Perrimon, Development (1993) 118: 401-415; and Phelps & Brand, Methods (April 1998) 14:367-379. See also, Spradling A C, P Element Mediated Transformation in *Drosophila*: A Practical Approach (ed. D. D. Roberts, IRL Press, Oxford)(1986) pp 175-179.

Generally, *Drosophila melanogaster* stocks used in the experiments described herein are as follows: Wild type Canton-S (BL-1), Sply$^{05091}$ (BL-11393), lace$^2$ (BL-3156) and lace$^{k05305}$ (BL-12176) lines, obtained from the Bloomington *Drosophila* Stock Center (Indiana University, Bloomington, Ind.). General fly husbandry was performed as described (Sullivan, W., Ashburner, M. and Hawley, R. S. (2000). *Drosophila* protocols. Cold Spring Harbor, N.Y.: Cold Spring Harbor Laboratory Press).

Other techniques useful in generating mutant and/or transgenic flies are described in Rubin, G, Hong L, Brokstein P, Evans-Holm M, Frise E, Stapleton M and Harvey D, 2000. A *Drosophila* complementary DNA resource, *Science* 287: 2222-2224.

Example 1

Isolation and Characterization of SPL cDNA from *Drosophila melanogaster* (Sply)

In order to seek out the *Drosophila melanogaster* SPL cDNA and genomic sequence, the *D. melanogaster* genomic database was searched for sequences which demonstrated significant homology to human SPL cDNA. The *Drosophila melanogaster* genomic database (http://flybase.bio.indiana.edu) was searched for predicted proteins using mouse (accession number AAH26135; amino acid sequence set forth in SEQ ID NO:6) and human (accession number XP_166113; amino acid sequence set forth in SEQ ID NO:18) SPL sequences. DNA homology searches were performed via the Berkeley *Drosophila* Genome Project web site using the BLAST search program (http://www.ncbi.nlm.nih.gov). One computed gene (CG8946) was identified that corresponded to a predicted SPL gene. Subsequently, two ESTs (LP04413, cDNA set forth in SEQ ID NO:27 and GH13783, cDNA set forth in SEQ ID NO:26) were identified which contained open reading frames that corresponded to the two predicted splice variants. The two clones are predicted based on alternative 5' exon usage and may be expressed in different subcellular locations.

The predicted *Drosophila melanogaster* SPL is located on the right arm of chromosome II, position 53F8-12. The cDNA sequence for the coding region of the *Drosophila melanogaster* SPL is set forth in SEQ ID NO:15 and encodes the SPL protein set forth in SEQ ID NO:16. The *Drosophila* SPL predicted protein sequence set forth in SEQ ID NO:16 is 49%, 49% and 43% identical to human, mouse and yeast SPL protein sequences, respectively.

In order to evaluate whether these clones contained a functional SPL gene, they were recloned into the yeast expression vector, pYES2 in which gene expression is driven by a galactose-inducible promoter. The open reading frame contained in LP04413 (polynucleotide sequence set forth in SEQ ID NO:) was amplified using primers LPEcoRI5=5'-TGGAAT-TCGATGCGTCCGTTCTCCGGCAGC-3' and LPXhoI3'=5'-CTCCTCGAGTCTATTTCTGGCTGG-GAGT-3' and was cloned into the yeast expression vector, pYES2, at EcoRI and XhoI restriction sites. This construct was transformed into a dpl1Δ strain using the lithium acetate method (Ito, H., Fukuda, Y., Murata, K. and Kimura, A. (1983). *J Bacteriol* 153, 163-8.). These constructs were transformed into a dpl1Δ strain in which the sole endogenous Saccharomyces cerevisiae SPL gene has been deleted (Saba, J. D., Nara, F., Bielawska, A., Garrett, S. and Hannun, Y. A. (1997). *J Biol Chem* 272, 26087-26090.). The dpl1Δ strain is unable to catabolize LCBPs, and it cannot proliferate on media containing low concentrations of D-erythro-sphingosine.

Expression of clones containing the potential *Drosophila melanogaster* SPL fully complement the dpl1Δ strain's sensitivity to 50 μM D-erythro-sphingosine. Further, whole cell extracts of dpl1 strains containing either pYES2-LP04413 or pYES2-GH3783 demonstrate restoration of SPL enzyme activity to wild type levels or greater, although not as high as a DPL1 overexpressing strain (DPL OE). Further, whole cell extracts of dpl1Δ strains overexpressing Sply demonstrate restoration of SPL enzyme activity.

Northern analysis of wild type *Drosophila melanogaster* embryos and larvae indicates that Sply expression is developmentally regulated, with the onset of expression occurring by 8-12 hours of embryogenesis. Embryonic expression was largely localized to the gut primordium as indicated by in situ hybridization.

Thus, this example describes Sply, the sphingosine-1-phosphate lyase gene in Drosophila melanogaster.

Example 2

Generation and Characterization of SPL Transposon Mutant D. melanogaster

Drosophila melanogaster stocks used in the experiments described herein are as follows: Wild type Canton-S (BL-1), Sply$^{05091}$ (BL-11393), lace$^2$ (BL-3156) and lace$^{k05305}$ (BL-12176) lines, obtained from the Bloomington Drosophila Stock Center (Indiana University, Bloomington, Ind.). General fly husbandry was performed as described (Sullivan, W., Ashburner, M. and Hawley, R. S. (2000). Drosophila protocols. Cold Spring Harbor, N.Y.: Cold Spring Harbor Laboratory Press)

Flies from the Berkeley Drosophila Genome Project gene disruption project (Spradling, A. C., Stern, D. M., Kiss, I., Roote, J., Laverty, T. and Rubin, G. M. (1995). Gene disruptions using P transposable elements: an integral component of the Drosophila genome project. Proc Natl Acad Sci USA 92, 10824-30.) were identified that harbor a transposon within the Sply open reading frame (designated Sply$^{05091}$). The transposon is located at nucleotide +269 relative to the start site of the larger transcript, LP04413, cDNA set forth in SEQ ID NO:27.

These flies were genetically crossed using techniques well known to ordinarily skilled artisans, and progeny were evaluated for the presence of homozygous insertional mutants (based on presence of rosy eye color, encoded by a recessive marker carried on the P-element). Northern analysis of total RNA obtained from Sply$^{05091}$ homozygotes confirmed an absence of Sply expression.

To determine the SPL function of each genotype, +/+, +/- and -/- flies were homogenized and whole extracts assayed for SPL activity. It was observed that SPL genotype corresponded with SPL activity with +/+>+/->-/-. Initial evaluation of homozygous mutants indicated that adult SPL mutants were flightless, suggesting a potential defect in either muscle development or energetics of the adult fly. Flight analysis was carried out essentially as described (Vigoreaux, J., J. Saide, K. Valgeirdottir, and M. Pardue. 1993. Flightin, a novel myofibrillar protein of Drosophila stretch-activated muscles. J Cell Biol. 121:587-598) by determining the percentage of flies that were flightless or exhibited downward, upward, or lateral flight capabilities in control Canton-S flies as compared to mutant flies as follows: 2-7 day old adult flies were released into a top-lit Plexiglas chamber. Flight behavior was scored as follows: upward flight=3, lateral flight=2, downward flight=1, flightless=0 (Vigoreaux, et al., 1993). Average flight scores were compared using a two-tailed student t-test.

Example 3

Further Characterization of the Sply P-element Insertional Mutant Drosophila melanogaster The sphingolipids of Drosophila melanogaster contain $C_{14}$ and $C_{16}$ sphingosine and dihydrosphingosine LCBs (see Example 4). Extracts of wild type and mutant flies were compared for their ability to degrade endogenous Drosophila melanogaster LCBPs in vitro. Extracts of Sply$^{05091}$ mutants failed to catabolize endogenous LCBPs, whereas extracts of wild type flies degraded endogenous Drosophila melanogaster LCBPs, indicating that the Sply gene product is responsible for LCBP catabolism in this organism.

To determine whether loss of Sply expression affects the levels of Drosophila melanogaster endogenous LCBs and corresponding LCBPs, the sphingolipid profile of homozygous Sply$^{05091}$ flies was evaluated and compared to wild type controls. Homozygous Sply$^{05091}$ adults demonstrated an eight-fold increase in LCBs and a 20-fold increase in LCBPs when compared to wild type (Table 1), indicating significant derangement of sphingolipid metabolism. This accumulation of LCBs and LCBPs was observed in homozygous Sply$^{05091}$ mutants as early as hours 12-18 of embryogenesis, correlating with the onset of Sply expression.

TABLE 1

Biochemical and biological characteristics of mutant models of sphingolipid metabolism.

| A. Characteristic | Canton-S | Sply$^{05091}$ | Sply$^{14a}$ | lace$^{k05305/2}$ | lace$^{k05305/+}$, Sply$^{05091}$ | lace$^{k05305}$, Sply$^{05091}$ | Sply$^{05091}$ + 1 mM D,L-threo-DHS |
|---|---|---|---|---|---|---|---|
| $C_{14/16}$ LCBs (nmol/100 mg) | 2.71 ± 0.28 | 24.22 ± 1.73 | 5.30 ± 0.59 | 0.15 ± 0.01 | 12.67 ± 1.93 | 5.75 ± 0.42 | 136%* |
| $C_{14/16}$ LCBPs (nmol/100 mg) | 0.30 ± 0.09 | 6.38 ± 0.44 | 1.02 ± 0.33 | 0.08 ± 0.04 | 4.06 ± 0.64 | 1.88 ± 0.17 | 81%* |
| Average flight score | 2.60 ± 0.032 | 0.40 ± 0.036 | 1.70 ± 0.074 | 1.62 ± 0.14 | 1.41 ± 0.063 | 0.56 ± 0.13 | 0.62 ± 0.057 |
| # of DLM fibers/hemithorax | 6.00 ± 0.00 | 4.15 ± 0.21 | 5.97 ± 0.089 | 5.94 ± 0.030 | 5.13 ± 0.26 | 5.81 ± 0.14 | N.D. |
| Average # of eggs/day | 44.5 ± 3.28 | 15.8 ± 2.98 | 43.4 ± 3.43 | N/A | 52.9 ± 4.03 | N/A | N.D. |
| Developmental lethality | 20% | 66.5% | 27% | N.D. | 20% | N.D. | N.D. |

Adult wild type flies and the indicated models of sphingolipid metabolism were analyzed for total phosphorylated (LCBPs) and unphosphorylated (LCBs) long chain base levels, flight performance, number of DLM per hemithorax, fecundity (egg-laying), and % mortality prior to completion of metamorphosis. Flight performance and LCB/LCBP levels were also determined in Sply$^{05091}$ homozygous flies treated with the sphingosine kinase inhibitor, D,L-threo-DHS.
LCB/LCBP levels in inhibitor-treated flies are given as percentage of untreated controls; these determinations were obtained in a separate experiment, and baseline sphingolipid levels were not comparable between the two experiments.
Canton-S is wild type.
Sply$^{05091}$ indicates the homozygous Sply null mutant.
lace$^2$ and lace$^{k05305}$ are recessive lethal alleles of serine palmitoyltransferase.
Sply$^{14a}$ indicates the homozygous Sply$^{05091}$ revertant.
All biochemical, flight, and fiber count data were obtained from mixed-age adults.
Values are as indicated, ±s.e.m.

Homozygous and heterozygous Sply$^{05091}$ flies were examined for evidence of anatomical, developmental, and functional abnormalities. Flies heterozygous for Sply$^{05091}$ were indistinguishable from wild type. Initial evaluation of flies homozygous for the Sply$^{05091}$ allele revealed no obvious defects in external anatomical structures at embryonic, larval or adult stages. However, adult mutants were almost uniformly flightless, with 91% of the mutant population scoring zero (in comparison to 4% wild type flies) in a standard flight performance assay (Table 1). Despite the severity of the flight defect in Sply$^{05091}$ homozygotes, the function of other muscle groups, including the jump and leg muscles did not appear to be affected. Moreover, evaluation of the giant fiber neuromuscular pathway by electrophysiological analysis indicated that this pathway remained functionally intact and was not responsible for the observed flight defect.

Sply$^{05091}$ homozygotes demonstrate abnormal flight muscle morphology.

To investigate further the etiology of Sply$^{05091}$ flight defects, adult mutants were sectioned through the thoracic region, and muscles were examined by light microscopy. These studies revealed a reduction in the number of muscle fibers comprising the DLMs required for flight. Whereas the thoraces of wild type flies invariably contained 6 symmetrical pairs of fibers, Sply$^{05091}$ homozygotes exhibited a general pattern of missing fibers, asymmetry, and hypertrophy of remaining fibers. Quantitative analysis of DLM fibers revealed a reduction from 6 per hemithorax in wild type to an average of 4.15 per hemithorax in the mutants (Table 1). Microscopic analysis of hemithoraces illuminated with polarized light confirmed the abnormal muscle configuration while demonstrating that muscle insertions were not affected.

Sply$^{05091}$ mutation does not disrupt muscle ultrastructure, template formation or embryonic muscle fusion. To determine the origin of the DLM defect, adult myocyte ultrastructure and larval and embryonic muscle development were investigated. Examination of Dmef2 expression in myoblast nuclei of nascent muscle fibers of early wild type and mutant embryos revealed no appreciable differences in muscle organization. Thus, myoblasts appear to successfully migrate from somites to correct sites in mutant embryonic segments. Similarly, analysis of myosin heavy chain expression in 0-24 hour wild type and mutant embryos revealed no gross changes in the organization of the developing mutant muscle fibers as compared to wild type indicating that myocyte fusion was not impaired.

To determine whether the DLM defect observed in Sply$^{05091}$ adult homozygotes occurred due to lack of template structures required for their formation during metamorphosis, T2 dorsal oblique muscles (DOMs) were evaluated in mutant larvae. Late-stage mutant larvae exhibited no alterations in number and/or size of DOMs. Therefore, it appears that the mutant muscle defect is restricted to DLMs and affects the adult muscle configuration subsequent to myoblast fusion events during metamorphosis. Despite this defect, the ultrastructure of the DLMs that are present in the Sply$^{05091}$ mutants generally appear to be intact as evidenced by transmission electron microscopy.

Sply$^{05091}$ homozygotes demonstrate decreased fecundity, semi-lethality and increased apoptosis in embryos. The number of offspring resulting from homozygous Sply$^{05091}$ crosses was about 10% of the number observed in wild type crosses. This loss of progeny could result from diminished egg-laying and/or diminished survival of embryos and larvae. Analysis of egg-laying indicated that fecundity of the mutants was about one third that of control flies (Table 1). This outcome could be the result of diminished male and/or female fertility. To distinguish between these possibilities, both male and female Sply$^{05091}$ homozygotes were mated to wild type flies, and egg-laying was measured in comparison to wild type pairs and homozygous mutant pairs. Numbers of eggs produced were significantly diminished in crosses of both male and female mutant flies with wild type mates (data not shown), indicating that the effect on fecundity was not gender-specific. Additionally, crosses between Sply$^{05091}$ homozygous males and females resulted in progeny with an overall survival (from egg to adulthood) of 33.5%, compared to an 80% survival rate in wild type flies. Lethality in the Sply$^{05091}$ mutants was high during larval stages (46%, compared to 3% in wild type), with the majority of larval death occurring during the first larval instar. Less severe effects were observed during pupation (22% lethality, compared to 1% in wild type), and no appreciable differences in survival were noted during embryogenesis. Sply$^{05091}$ mutant embryos were examined by in situ TUNEL assay, and patterns of apoptosis were compared to those of wild type controls. Sply$^{05091}$ mutant embryos demonstrated a pronounced enhancement of apoptosis compared to wild type controls, especially in a specific region of the posterior pole near the developing genital disc.

Example 4

Characterization of Sphingolipid Species in the Drosophila melanogaster

Without being bound by theory, it is hypothesized that the phenotype of the SPL mutant Drosophila melanogaster is caused by an abnormal level of S-1-P during development. Further, without being bound by theory, it is our hypothesis that phosphorylated sphingoid base species are responsible for regulating cell proliferation, migration and other events required for both tumor formation and normal developmental processes in this model organism. Therefore, characterization of sphingolipid species in Drosophila melanogaster was determined.

Method: Wild type (Canton S) whole fly extracts were prepared by mechanical disruption. Lipids were isolated by two-phase extraction and derivatized with the fluorescent molecule o-pthalaldehyde essentially as described in Caligan, et al. hereby incorporated by reference in its entirety (Caligan, T. B., K. Peters, J. Ou, E. Wang, J. Saba, and A. H. Merrill, Jr. 2000. A high-performance liquid chromatographic method to measure sphingosine 1-phosphate and related compounds from sphingosine kinase assays and other biological samples. *Analytical Biochemistry.* 281:36-44). Derivatized lipid extracts were separated by HPLC using a $C_{18}$ ODS column (LUNA 4.6×250 mm) and mobile phase MeOH/H$_2$0/1M TBAP 82:17:0.9, pH 4.8. Standards included commercially available $C_{10}$, $C_{12}$, $C_{14}$, $C_{16}$, $C_{18}$ and $C_{20}$ sphingosines, as well as the phosphorylated forms of these standards, prepared by incubation of sphingosine standards with extract from a yeast strain which overexpresses the major yeast sphingosine kinase, LCB4.

Results: *Drosophila melanogaster* extracts contained only sphingolipid species which comigrated with $C_{14}$ sphingosine and $C_{14}$ sphingosine-1-phosphate (S-1-P) standards under the stated conditions. To verify the identity of the peaks in fly extracts which comigrated with $C_{14}$sphingosine and $C_{14}$S-1-P standards, extracts and standards were compared in four different mobile phase buffers. The peak identified as $C_{14}$ sphingosine comigrated with the $C_{14}$ sphingosine standard under all four conditions (Table 2). However, the peak identified as $C_{14}$S-1-P demonstrated a slight difference from the $C_{14}$S-1-P standard under conditions which exploit differences in charge (MeOH/10 mM KP/1 M TBAP, pH 7.2, 81:18:1).

TABLE 2

Sphingolipid Identification

| Mobile Phase | $C_{14}S$ std | $C_{14}S$ in extract | $C_{14}$S-1-P std | $C_{14}$S-1-P in extract |
|---|---|---|---|---|
| MeOH/H$_2$O/1 M TBAP pH 4.8 82.1:17:0.9 | 19.1 min | 19.0 min | 14.8 min | 14.8 min |
| MeOH/H$_2$O/1 M TBAP pH 4.8 79.1:20:0.9 | 27.3 min | 27.1 min | 22.5 min | 22.1 min |
| MeOH/10 mM KP/1 M TBAP pH 5.5 81:18.1 | 21.9 min | 22.0 min | 18.3 min | 17.2 min |
| MeOH/10 mM KP/1 M TBAP pH 7.2 81:18.1 | 21.4 min | 21.8 min | 15.0 min | 17.1 min |

This finding is likely to be due to a chemical modification of the phosphate group, since a phosphatase capable of dephosphorylating the $C_{14}$S-1-P standard does not recognize this substrate. Mass spectroscopy is being utilized to identify the phosphate group modification of this S-1-P species. Herein, this sphingolipid is referred to as "modified $C_{14}$S-1-P."

Example 5

Genetic Reversion of the Sply[05091] Mutation Restores Normal Muscle Configuration To verify the importance of Sply in mediating the semi-lethality, egg-laying defects and flight muscle phenotype of the mutant line, the transposon in the Sply[05091] locus was mobilized Genetic reversion of the Sply[05091] mutation restores normal muscle configuration. in Sply[05091] homozygotes following introduction of an active transposase. Precise excision of the transposon was subsequently confirmed by PCR and DNA sequence analysis. A homozygous revertant line (Sply[14a]) was generated as described in Materials and Methods and was found to express Sply mRNA at levels equivalent to wild type. Sply[14a] demonstrated reversion of the muscle fiber morphology defect, and flight performance was largely restored (Table 1). Additionally, apoptosis in the revertant embryo was diminished in comparison to Sply mutants. The appearance of the specific cluster of TUNEL-positive cells was <1% (n=197), 48% (n=160) and 72% (n=324) in Canton-S, Sply[14a], and Sply[05091] in stage 12-15 embryos, respectively. Phenotypic reversion correlated with normalization of LCB and LCBP levels in revertant extracts (Table 1).

Example 6

The Sply[05091] Muscle Defect is Suppressed by Reducing Sphingolipid Intermediates To investigate the possibility that the Sply[05091] muscle phenotype was caused by accumulation of LCBPs, an inhibitor of sphingosine kinase, D,L-threo-DHS, was introduced to the growth media of mutant and wild type flies. Flies were grown on the supplemented media; and F2 progeny were examined. When wild type flies were grown on media supplemented with 10 µM D,L-threo-DHS, no deleterious effects were observed. Sply[05091] mutants grown on this media demonstrated a slight but significant improvement in flight performance. To determine whether the flight improvement coincided with a restoration of LCBP levels, LCB/LCBP levels were analyzed in mutants and controls grown on D,L-threo-DHS. LCBP levels in Sply[05091] homozygotes grown in the presence of sphingosine kinase inhibitor were reduced by approximately 20% (Table 1). Similarly, LCBP levels in wild type flies were reduced to 20% of normal levels.

Assuming that the mutant phenotypes are caused by an accumulation of LCB/LCBPs, we predicted that diminishing SPT activity in the Sply[05091] homozygote would suppress the Sply[05091] phenotype by reducing production of sphingolipid intermediates. Toward that end, a lace[k05305] null allele was introduced onto the Sply[05091] chromosome by genetic recombination, thus generating a Sply[05091], lace[k05305]/+ line. Sply[05091], lace[k05305]/Sply[05091], lace+ flies exhibited reversion of the abnormal muscle patterning, and flight performance was substantially improved (Table 1). Additionally, the pattern of embryonic apoptosis appeared similar to that of the wild type. Phenotypic reversion correlated with a marked reduction of the LCBs and LCBPs (Table 1).

Example 7

Loss of Sply Expression Suppresses the Lace Null Phenotype

Inheritance of two lace[k05305] hypomorphic alleles was reported to be almost completely lethal, whereas a heterozygous allelic combination (lace[k05305]/lace[2]) yields flies that frequently survive but manifest severe developmental phenotypes leading to eye, bristle and wing abnormalities (Adachi-Yamada, T., Gotoh, T., Sugimura, I., Tateno, M., Nishida, Y., Onuki, T. and Date, H. (1999). Mol Cell Biol 19, 7276-7286.). We predicted that the lace mutant phenotype is due to diminished levels of sphingolipid intermediates. Further, we reasoned that inhibiting sphingolipid catabolism in lace mutants might allow sufficient accumulation of trace sphingolipids obtained through the diet to ameliorate developmental defects induced by the lack of critical sphingolipid intermediates. To address this possibility, a *Drosophila melanogaster* line homozygous for both the Sply[05091] and lace[k05305] alleles was generated. Significantly, the presence of the Sply[05091] allele increased the recovery of lace homozygotes from 9% to 39% of that expected by independent assortment. Furthermore, the introduction of Sply[05091] fully suppressed the eye, bristle and wing phenotypes in the resulting flies. In accordance, sphingolipid intermediates were substantially increased in this line, in comparison to lace[2]/lace[k05305] heterozygotes, which are the only available lace mutants with sufficient viability for comparison (Table 1).

Example 8

Human SPL and SK Expression Patterns in Cancer

To determine if SK and/or SPL expression is altered in human tumors, we utilized a cancer profiling array which contains more than 240 cDNA pairs representing tumor tissue and corresponding normal tissue from the same patient. By utilizing tissue pairs from one patient, differences between gene expression in tumor and normal tissue which might be due to person to person variability should not confound the interpretation of results. Additionally, each blot was normalized for loading using four separate housekeeping genes.

Standard hybridization techniques known in the art were utilized to probe this cDNA blot with the full length human SPHK1 cDNA (set forth in SEQ ID NO:22), which was obtained by RT-PCR of human umbilical vein endothelial cell total RNA Analysis of the array indicates that SK expression appears to be significantly increased in numerous human cancers including tumors of breast, uterus, stomach, ovary, lung, kidney and rectum. Additionally, some tumors demonstrated increased SK expression in metastatic lesions compared to tumor tissues. None of the SK overexpressing tumors demonstrate loss of SPL expression. Thus, altered SK expression is observed in primary human tumors. Therefore, modulating the activity of SK protein either by altering gene expression or through direct action on the protein may provide a useful treatment for individuals afflicted with an SK-related cancer. Furthermore, SK expression serves as a useful diagnostic marker of cancer in humans.

Standard hybridization techniques were utilized to probe the cDNA blot with a 300 nucleotide 3' fragment of human SPL cDNA (SEQ ID NO:23), which was obtained as described in U.S. Pat. No. 6,423,527. Analysis of the array indicated that, whereas human SPL expression is matched closely in most tissue pairs, it is significantly reduced in colon cancer specimens, with a 50% reduction in expression in colloid cancer of the colon and 61% reduction in adenocarcinoma of the colon. Reduced SPL expression was also seen in adenocarcinaom of the uterus. None of the tumors in which SPL expression is diminished demonstrates SK overexpression. Thus, altered SPL expression is observed in primary human tumors. Therefore, modulating the activity of SPL protein either by altering gene expression or through direct action on the protein may provide a useful treatment for individuals afflicted with an SPL-related cancer. Furthermore, SPL expression serves as a useful diagnostic marker of cancer in humans.

Example 9

Isolation of Drosophila melanogaster Genes Involved in Sphingolipid Metabolism Drosophila melanogaster genes that are involved in sphingolipid metabolism were identified. Using the human SK protein sequence set forth in SEQ ID NO:21 as probe, we identified two homologous Drosophila melanogaster sequences which could potentially encode fly SK proteins. These two Drosophila melanogaster SK protein sequences are set forth SEQ ID NOs: 19 and 20 and are shown in FIG. 1. The annotation FBan0001747 for gene CG1747, which has FlyBase accession number FBgn0030300, is located on chromosome arm X, and has a transcription unit length of 2020 nucleotides. This gene has the transcript CT5088. The function of this gene has been categorized as enzyme/diacylglycerol kinase, based upon a conserved lipid kinase domain. The annotation FBan0002159 for gene CG2159, which has FlyBase accession number FBgn0035391, is located on chromosome arm 3L, and has a transcription unit length of 4431 nucleotides. This gene has the transcript CT2650. These two sequences have not been cloned, and neither functional data nor ESTs are available. (DSK1747 amino acid sequence is set forth in SEQ ID NO:19; DSK2159 amino acid sequence is set forth in SEQ ID NO:20).

Example 10

Characterization of 2 Drosophila melanozaster SK Genes Involved in Sphingolipid Metabolism In order to identify potential SK genes in Drosophila melanogaster, the Drosophila melanogaster genomic database was searched using a tBLASTn enquiry for sequences that demonstrated significant homology to human SK cDNA. This led to the identification of two candidate SK as described above. Gene CG1747 is located on chromosome X and has been categorized as enzyme/diacylglycerol kinase, based upon a conserved lipid kinase domain. Gene CG2159 is located on chromosome arm 3L, and has a transcription unit length of 4431 nucleotides. ESTs corresponding to these two loci were obtained, their integrity confirmed by sequence and restriction analysis (sequences of the full length amino acids of SK1 and SK2 are set forth in SEQ ID NOs:28 and 29; full length cDNAs for SK1 and SK2 are set forth in SEQ ID NOs:24 and 25). These CG1747 and CG2159 cDNA clones were then re-cloned into yeast expression vector pYES2, under regulation of a galactose-inducible promoter (Rubin, G, Hong L, Brokstein P, Evans-Holm M, Frise E, Stapleton M and Harvey D, 2000. A Drosophila complementary DNA resource, Science 287:2222-2224.). These constructs were transformed into yeast strain JSK392 (Kim, S, Fyrst H and Saba J, 2000. Genetics 156:1519-1529.), in which the endogenous SPL, SK and S-1-PP genes (DPL1, LCB4 and YSR2 respectively) have been deleted. This strain can survive in the absence of LCBP synthesis, but expression of a functional SK gene in this background is lethal, due to severe accumulation of LCBPs which cannot be degraded. When CG1747 and CG2159 expression was induced in this background in the presence of galactose, no yeast growth occurred, indicating that these cDNAs encode functional SK enzymes. Finally, a CG2159 transposon mutant was obtained and demonstrates lack of expression from this locus (Rosemann, R, Johnson E, Rodesch C, Bjerke M, Nagoshi R and Geyer P, 1995. Drosophila melanogaster, Genetics 141:1061-1074.). This mutant (Sphk2$^{KG05894}$) was created by the insertion of a P-element into the 5' UTR of CG2159, as previously described. Preliminary studies indicate this mutant has a mild defect in DLMs, similar to that seen in Sply mutants.

Example 11

Characterization of the Chemical Structures and Concentration of Sphingolipid Metabolites in Wild Type Flies and Those with Defects of Sphingolipid Metabolism Materials and Methods:

Drosophila melanogaster Lines.

The lace gene encodes one subunit of a Drosophila serine palmitoyltransferase. Inheritance of two lace$^{k05305}$ null alleles is reported to be uniformly lethal, whereas the heterozygous allelic combination used in these experiments, lace$^{k05305}$/lace$^2$, leads to severe developmental phenotypes and a low percentage of viable progeny (Adachi-Yamada, T., T. Gotoh, I. Sugimura, M. Tateno, Y. Nishida, T. Onuki, and H. Date. 1999. *Mol. Cell. Biol.* 19: 7276-7286.). A *Drosophila* line homozygous for a null allele of one of two putative sphingosine kinase (SK) genes was also utilized in these experiments. This mutant (Sphk2$^{KG05894}$) was created by the insertion of a P-element into the 5' UTR of CG2159, as previously described. The product of this gene functionally complements a yeast SK mutant. Wild type Canton-S (BL-1), lace$^2$ (BL-3156), lace$^{k05305}$ (BL-12176), and Sphk2$^{KG05894}$ (BL-14133) lines were obtained from the Bloomington *Drosophila* Stock Center (Indiana University, Bloomington, Ind.).

Flies were reared on standard fly media at room temperature. In all cases, control and mutant flies were reared in parallel under identical conditions. For developmental analysis, adult flies were allowed to deposit embryos on grape juice agar plates. After the collection period, plates were removed from the collection chamber, covered, and aged at room temperature to obtain appropriately staged embryos. For example, to collect 6-12 hour embryos, adults were exposed to plates for 6 hours, plates were removed and aged for an additional 6 hours before embryos were collected. Embryos were removed from the plates by washing with 0.7% sodium chloride/0.03% TritonX-100, rinsed extensively with water and frozen at −70° C. for storage.

Preparation of *Drosophila* Lipid Extracts.

Samples containing 25 mg of frozen intact fly material were placed in a 7 ml Potter Elvehjem homogenizer. 20 μl of a mixture of internal LCB standards (Matreya Inc., Pleasant Gap, Pa.) containing 250 to 500 pmol of each LCB were then added. Flies were homogenized in 2 ml of ice cold methanol/water, 1:1 (v/v) with a loose pestle followed by a tight pestle until it moved smoothly. Extracts were further homogenized with a tip sonicator (3×20 sec.) while on ice, then transferred to a glass tube and centrifuged at 1500×g for 10 minutes. Supernatants were recovered and dried down in a speed vac. Extracts were resuspended in 200 μl of methanol containing 0.1 M ammonium hydroxide, followed by vortexing, bath sonication and incubation at 37° C. for 1 hr to allow hydrolysis of esterified acyl chains. Following hydrolysis, the samples were cooled to room temperature, dried down in a speed vac and resuspended in 500 μl of methanol/water, 2:3 (v/v) containing 0.1% glacial acetic acid (solvent A).

Solid Phase Extraction on a Strata C18-E Column.

The Strata C18-E solid phase extraction column (50 mg/ml) (Phenomenex, Torrance, Calif.) was initially wetted with 200 μl of methanol, followed by equilibration with 1 ml of solvent A. Fly extracts or LCB standards in solvent A were applied to the equilibrated Strata C18-E column, followed by a wash with 1 ml of solvent A. A second wash of the column was performed by the addition of 600 μl of methanol. LCBs were eluted from the column with 600 μl of methanol: 10 mM ammonium acetate, 9:1 (v/v) and dried down in a speed vac.

HPLC Analysis.

LCBs were derivatized with ortho-phthalaldehyde (OPA) (Sigma St. Louis, Mo.) as previously described (Caligan, T. B., K. Peters J. Ou, E. Wang, J. Saba, and A. H. Jr. Merrill. 2000. *Anal. Biochem.* 281: 36-44.). The OPA-derivatized LCBs were separated on a reverse-phase column (Luna RP-18, 3μ, 4.6×75 mm) (Phenomenex, Torrance, Calif.) with the mobile phase methanol/10 mM ammonium acetate, pH 5.2, 82:18 (v/v). Flow rate was 1 ml/min. The HPLC system used was a Beckman System Gold with a 125 solvent module.

The fluorescent LCBs were detected and quantified using a Spectra-Physics fluorescence detector (SP 8410).

Mass Spectrometry Analysis of *Drosophila* LCBs.

A Strata C18-E column-purified lipid extract from adult Sphk2$^{KG05894}$ flies or a $C_{14}$ So standard were analyzed on a Micromass Quattro LCZ instrument following direct injection of 10 μl of sample. Mobile phase was 80 percent methanol containing 0.1 percent formic acid. Flow rate was 0.2 ml/min. Structural confirmation of LCBs was obtained by positive electrospray ionization (ESI+) mass spectrometry. LCBs were detected by precursor ion scans of structurally distinct ion fragments as described (Sullards, M. C., and A. H. Jr. Merrill. 2001. *Sci. STKE.* 67: 1-11.). Applying 3.5 kV to the capillary started the spray and the collision-induced decomposition spectra, at a cone voltage of 20 V, were recorded at a collision energy of 15 eV with argon as collision gas.

Abbreviations: So: sphingosine; Sa: didydrosphingosine, LCB: free long chain sphingoid bases; LCBP: phosphorylated free long chain sphingoid bases; SPT: serine palmitoyltransferase; OPA: ortho-phthalaldehyde.

Results:

HPLC Separation of Sphingoid Bases and Solid Phase Extraction of Sphingoid Bases.

An HPLC method was developed for the separation of LCBs with a carbon number of 14 to 18. Initial HPLC separation of crude methanol/water lipid extracts from adult flies were complicated by high content of contaminating fluorescent material. Consequently, a solid phase extraction step using a Strata C18-E column prior to HPLC analysis was introduced. When methanol was employed as the eluting solvent, recovery of LCB standards was less than 2 percent. This inadequate recovery of the LCB standards from the Strata C18-E column was completely overcome by addition of 10 percent by volume of a 10 mM ammonium acetate solution to the methanol elution solvent. By employing this elution system, recovery in the range of 60 to 95 percent was obtained for the $C_{14}$ and $C_{16}$ sphingoid base standards (Table 3).

TABLE 3

Recovery of sphingoid base standards following solid phase extraction on a STRATA C18-E column.

| Sphingoid base | $C_{14}$ So | $C_{16}$ So | $C_{16}$ Sa | $C_{18}$ So | $C_{18}$ Sa |
|---|---|---|---|---|---|
| Recovery (%) | 95.4 ± 3.3 | 77.9 ± 7.1 | 60.6 ± 4.2 | 39.3 ± 6.5 | 16.3 ± 4.0 |

Values are shown as mean ± standard deviation for at least three independent measurements.

HPLC Analysis of LCBs from *Drosophila*.

Elution of adult fly lipids from the Strata C18-E column with methanol/10 mM ammonium acetate 9:1 (v/v) still resulted in an HPLC spectrum with significant unwanted background fluorescence. This background was minimized with the addition of a methanol wash prior to elution with methanol/10 mM ammonium acetate 9:1 (v/v) (see Materials and Methods for details). Adult flies of three different lines were analyzed. The lipid profile of wild type flies was compared to that of a sphingosine kinase (Sphk2) mutant and a serine palmitoyltransferase (SPT, lace) mutant (See Materials and Methods above). The Sphk2 mutants would be predicted to manifest a reduced capacity to phosphorylate LCBs and as a consequence should demonstrate increased levels of LCBs. In contrast, the hypomorphic lace mutants are defective in the first step of sphingolipid de novo biosynthesis and would be predicted to exhibit diminished levels or complete absence of LCBs. Three peaks demonstrating the same retention times as the $C_{14}$ So, $C_{16}$ So and $C_{16}$ Sa standards were identified in wild type fly extracts. In addition, a major peak that eluted with a retention time between that of $C_{14}$ So and $C_{16}$ So was identified. All four peaks mentioned above were increased in the Sphk2 mutant and decreased in the lace mutant, consistent with the likelihood that these peaks represented LCBs. No peaks that eluted with retention times corresponding to the $C_{18}$ LCB standards were observed.

Following isocratic elution from a C18 reverse phase HPLC column, a plot of the carbon length of a derivatized sphingoid base standard against the log of the retention time shows a linear correlation between sphingoid bases belonging to the same molecular class (Lester, R. L., and R. C. Dickson. 2001. *Anal. Biochem.* 298: 283-292.). This can be useful for the identification of an unknown sphingoid base. A linear correlation exists between the retention time of the unknown peak 2 and the two Sa standards in this plot. This finding strongly suggests that peak 2 is $C_{14}$ Sa.

Mass Spectometry Analysis of LCBs from *Drosophila*.

LCBs can be identified through their patterns of collision-induced dissociation and precursor ion scans using positive ion electrospray mass spectrometry (ESI+). Based on their unique molecular structures, typical decomposition products arise from the loss of two water molecules. The precursor ion spectrum of m/z 208 ($C_{14}$ So minus two water molecules) shows parents as m/z 244 ($C_{14}$ So) and m/z 226 ($C_{14}$ So minus one water molecule). In order to verify the existence of $C_{14}$ Sa in *Drosophila*, we analyzed a Strata C18-E column purified lipid extract by ESI+. A lipid extract from the Sphk2 mutant was chosen for the analysis since it demonstrated elevated levels of LCBs. Initially we sought the presence of endogenous $C_{14}$ So. A precursor ion spectrum of m/z 208 identifyied $C_{14}$ So (m/z 244) in the extract. Subsequently, we sought the presence of $C_{14}$ Sa. A precursor ion spectrum of m/z 210 identifyied endogenous $C_{14}$ Sa (m/z 246). In addition, precursor ion scans of m/z 236 and m/z 238 identified endogenous $C_{16}$ So and $C_{16}$ Sa in the fly extract. Precursor ion scans of m/z 264 and m/z 266 failed to identify $C_{18}$ LCBs in the fly extract supporting the results obtained from the HPLC analysis.

$C_{14}$ and $C_{16}$ Sphingoid Bases in *Drosophila* Models of Sphingolipid Metabolism Endogenous *Drosophila* LCBs were quantified by performing HPLC separation of Strata C18-E column purified extracts either with or without the addition of a defined amount of $C_{14}$ So, $C_{16}$ So and $C_{16}$ Sa standard. Separation was followed by comparison of the integrated area obtained for each fluorescent LCB peak (Table 4). Interestingly, lace and Sphk2 mutant flies differed appreciably from wild type flies in both the total amount and composition of LCBs, as determined by analysis of lipid extracts from each line. The total amount of LCBs in the wild type was approximately 1.5 nmol/100 mg of whole flies. The Sphk2 mutants exhibited a 3.3 fold increase and the lace mutants, a 2.5 fold decrease in the total amount of LCBs in comparison to wild type flies. $C_{14}$ So accounted for approximately 42 percent of the total amount of LCBs in the wild type flies, whereas $C_{14}$ Sa accounted for approximately 47 percent. Therefore, the molar ratio of $C_{14}$ So to $C_{14}$ Sa was approximately 1:1. In the Sphk2 mutant, the corresponding values were 26 percent $C_{14}$ So and 67 percent $C_{14}$ Sa resulting in a molar ratio of approximately 1:2.5, whereas in the lace mutant the corresponding values were 16 percent $C_{14}$ So and 81 percent $C_{14}$ Sa resulting in a molar ratio of approximately 1:5.

TABLE 4

HPLC analysis of endogenous LCBs in various adult *Drosophila* lines.

|  | Wild type | Sphk2 | lace |
| --- | --- | --- | --- |
| $C_{14}$ So (nmol/100 mg of flies) | 0.637 ± 0.132 | 1.282 ± 0.144 (201.3) | 0.100 ± 0.019 (15.7) |
| $C_{14}$ Sa[a] (nmol/100 mg of flies) | 0.718 ± 0.097 | 3.282 ± 0.361 (457.1) | 0.496 ± 0.055 (69.1) |
| $C_{16}$ So (nmol/100 mg of flies) | 0.055 ± 0.007 | 0.160 ± 0.011 (290.9) | 0.018 ± 0.002 (37.7) |
| $C_{16}$ Sa (nmol/100 mg of flies) | 0.051 ± 0.009 | 0.198 ± 0.026 (388.2) | n.d. |
| Total LCBs (nmol/100 mg of flies) | 1.461 ± 0.245 | 4.922 ± 0.542[b] (336.9) | 0.614 ± 0.076[c] (42.0) |
| $C_{14}$ So/$C_{14}$ Sa (mol:mol) | 0.89 | 0.39 | 0.20 |

Values are shown as mean ± standard deviation for three independent measurements.
Value n.d. means there was no detectable LCB at the amount of fly material analyzed.
Numbers in parentheses represent percent of wild type.
[a]An estimated value for the recovery of $C_{14}$ Sa from the Strata C18-E column was determined using the following formula; % recovery of $C_{14}$ Sa = % recovery of $C_{16}$ Sa × (% recovery of $C_{14}$ So/% recovery of $C_{16}$ So).
[b]Significantly different from wild type; $P < 0.001$.
[c]Significantly different from wild type; $P < 0.005$.

$C_{14}$ Sphingoid Bases in *Drosophila* Development.

Genetic studies have implicated a role for sphingolipid intermediates in the process of development. However, quantification of these molecules throughout development has not been performed. To investigate whether a biochemical basis for the potential role of sphingolipid intermediates exists, we evaluated the endogenous $C_{14}$ LCBs at different stages of *Drosophila* development (Table 5). The total amount of $C_{14}$ LCBs remained fairly constant throughout the development of the wild type. However, developmental progress from early embryos to pupae was associated with a seven fold increase in the molar ratio of $C_{14}$ So to $C_{14}$ Sa.

TABLE 5

HPLC analysis of endogenous $C_{14}$ LCBs in different stages of wild type *Drosophila* development.

| | Embryo (0-6 hr) | Embryo (6-12 hr) | Embryo (12-18 hr) | Embryo (18-24 hr) | Larvae | Pupae |
|---|---|---|---|---|---|---|
| $C_{14}$ So (nmol/100 mg of material) | 1.210 ± 0.173 | 2.132 ± 0.359 | 1.616 ± 0.261 | 1.713 ± 0.072 | 3.328 ± 0.318 | 2.094 ± 0.126 |
| $C_{14}$ Sa (nmol/100 mg of material) | 1.156 ± 0.122 | 1.010 ± 0.098 | 0.461 ± 0.051 | 0.387 ± 0.012 | 0.722 ± 0.033 | 0.309 ± 0.047 |
| Total $C_{14}$ LCBs (nmol/100 mg of material) | 2.366 ± 0.295 | 3.142 ± 0.457 | 2.077 ± 0.312 | 2.100 ± 0.084 | 4.050 ± 0.351 | 2.403 ± 0.173 |
| $C_{14}$ So/$C_{14}$ Sa (mol:mol) | 0.97 | 2.11 | 3.51 | 4.43 | 4.61 | 6.78 |

Values are shown as mean ± standard deviation for three independent measurements.

Example 12

Analysis of Gross and Microscopic Tumor Development in *Drosophila melanogaster* Strains with Altered Sphingolipid Metabolism Some *Drosophila melanogaster* sphingolipid metabolic mutants may develop tumors, especially those which demonstrate significant accumulation of S-1-P. Previously characterized *Drosophila melanogaster* tumors associated with lgl and dlg mutations possess characteristics associated with neoplastic growth in vertebrates, including lethality to the host, repeated transplantability, invasiveness, absence of terminal differentiation, rapid growth in vivo and in tissue culture, and defective cell-cell interactions and communication. Evaluation of each of these characteristics in grossly or microscopically visible tumors arising in mutants is performed. Overgrowth of imaginal discs is sought in all mutants even in the absence of gross tumors. Lethal mutations may suggest the presence of tumor formation during early developmental stages. The ability of cells of imaginal disc tumors or imaginal disc overgrowth to respond to normal differentiation signals during metamorphosis is evaluated by transplanting mutant imaginal discs into wild type larvae and following their fate. The ability of tumors or hyperproliferative imaginal discs to be serially cultured in vitro and in the abdomens of adult females for numerous transfer generations is assessed. Evidence of tumor invasiveness and metastatic capacity will be determined by determining the presence or absence of invasion into tissues surrounded by an epithelial sheath using histological analysis.

Example 13

Assessment of Gross and Microscopic Anatomic Defects in *Drosophila melanogaster* Strains with Altered Sphingolipid Metabolism Certain illustrative experimental methods are described herein, for example the above section before Example 1. Further illustrative techniques that can be used to further define the present invention, for example general techniques for assessment of gross and microscopic anatomical defects of *Drosophila melanogaster*, are known in the art and are further described herein. Lifespan of each line is determined and compared to wild type flies to assess effects on viability. Gross anatomy of tracheal and muscular systems is viewed in larvae with polarized light and in adults by viewing standard thick sections under light microscopy, in order to identify gross defects affecting trachea or muscle number, size, location or proper attachment. Preparation for light microscopy involves storing flies in a glycerol/ethanol solution, followed by 70% ethanol, dissecting away unnecessary structures, rehydrating and mounting or embedding the specimen for sectioning. Visualization is be performed using bright-field, DIC illumination, phase contrast or dark-field illumination. Electron microscopic analysis of the IFMs is performed on adults, larvae and pupae. The early *Drosophila melanogaster* embryo is amenable to structural analysis using any of a large number of highly specific antibodies which is detected using fluorescent secondary or, in some cases, primary antibodies. Large numbers of staged embryos can be collected from normal and mutant stocks and prepared for fluorescent analysis. This process involves dechorionation using a bleach solution, permeabilizing the vitelline membrane, fixation (without methanol) and vitelline membrane removal, staining, washing and mounting. Since lace mutants demonstrate abnormal apoptosis of imaginal wing discs, we plan to investigate any changes in imaginal disc structure and eversion in all mutants. Dissection of imaginal discs is performed in a saline solution and involves tearing the third instar larva in half, inverting the body wall and pinching clusters of dorsal or ventral discs away from the body. Discs may be left attached

Example 14

Identification of Pharmacologic Suppressors of SPL Mutant's Inability to Fly by Screeing an Array of Rationally Designed Chemicals with Homology to Sphingolipids for their Ability to Restore Flight to SPL Mutant Progeny Pharmacologic suppressors of the Sply mutant *Drosophila melanogaster*'s inability to fly are identified by screening an array of rationally designed chemicals with homology to sphingolipids for their ability to restore flight to the Sply mutant *Drosophila melanogaster*. Mutant SPL flies are grown at 18° C. in media supplemented with either vehicle control or micromolar concentrations of inhibitor. The ability of various inhibitors to restore flight will be measured using a standard scoring method, also as described elsewhere herein (see also Vigoreaux, et al., 1993, J Cell Biol 121:587-598). The efficacy and biochemical characteristics of interesting compounds will then be quantified by 1) determining the $IC_{50}$ of the inhibitor on purified SK, SPL and other enzymes involved in sphingolipid metabolism, such as serine palmitoyltransferase, ceramide synthase, sphingosine desaturase, ceramidase, ceramide kinase, phosphoethanolamine cytidylyltransferase, CDP-ethanolamine phosphotransferas, acid sphingomyelinase and neutral sphingomyelinase. The IC50 of the inhibitor is also determined on recombinant human SK, SPL and other enzymes involved in sphingolipid metabolism as listed above; 2) analyzing the kinetics of inhibition using classical Michaelis-Menten methods, and 3) determining the reversibility of the inhibition. Synthetic analogs are created for the screen. A library of 1-aryl-2-dimethylaminopropane-1,3-diol derivatives for screening as potential SK inhibitors are synthesized. Four diastereomers (D or L, erythro or threo) are synthesized for each member of the library. In the library the fatty acid amide group is replaced with two N-methyl groups and make similar variations in the polar and aromatic substituents. The synthetic plan makes use of the well-known Garner aldehyde (See 1 in FIG. 2) as starting material, since 1 is readily available in either enantiomeric form. A recent and exhaustive review of organometallic additions to 1 summarizing the effects of metal, solvent, and added Lewis acid catalyst has been published, and indicates that the erythroproduct is usually favored in most reactions. Thus, by choosing the D- or L-enantiomer of 1 as starting material, pure erythro stereoisomers of each library member are prepared. A novel and flexible route for assembling the corresponding threo analogues (4a-c, FIG. 2) is carried out using a straightforward extension of methodology for making PDMP analogues. The parent compound, 4a, is already known and readily available. The strategy relies on the syn-selective addition to 1 of arylmetal compounds (Aryl-Met) in the presence of certain sulfide and phosphine additives. Both the erythro and threo synthetic routes are modified to prepare substituted variations at the primary carbon atom. A representative synthetic procedure is shown in FIG. 3 for the preparation of 7a-c. A wide range of nitrogen, oxygen, and carbon nucleophiles could react with mesylates like 5a-c to furnish new libraries of dimethylated PDMP analogues and homologues.

Example 15

Further Evaluation of Candidate Drugs by Testing Their Ability to Inhibit Human SK in a Yeast Screen Devised such that Inhibition of SK Confers Cell Survival Compounds identified in the fly screen as described in Example 14 are further evaluated for their ability to inhibit human SK in a yeast model. Compounds which block the activity of human SK should restore growth on galactose to yeast strain dpl1ysr2lcb4 (Gal1,10p:human SPHK1). This strain cannot catabolize S-1-P or endogenous yeast S-1-P analogs due to the deletion of genes encoding SPL and S-1-P phosphatases. The endogenous yeast SK gene, LCB4 has also been deleted, so that no endogenous S-1-P analogs are made under baseline conditions. This strain has been transformed with a plasmid containing the human SPHK1 gene under regulation of a galactose inducible promoter, such that expression of an active SK in the presence of galactose is lethal to this strain. Inhibition of human SK protects cells from galactose-induced lethality and confirms the efficacy of the compound in question. Activity of the human SPHK1 gene in this strain has been verified by two methods, first HPLC analysis of SK activity in whole extracts of cells grown (for a limited time) in the presence of galactose, and second, the inability of this strain to form colonies on galactose-containing plates.

D-erythro-sphingosine, N,N-dimethylsphingosine, and D,L-threo-dihydrosphingosine are obtained from Biomol Research Inc. (Plymouth Meeting, Pa.). The morpholine, piperadine and erythro series of PDMP analogues is obtained. Other analogues are prepared as described above and according to previously described methods (Srivastava, M., L. Bubendorf, V. Srikantan, L. Fossom, L. Nolan, M. Glasman, X. Leighton, W. Fehrle, S. Pittaluga, M. Raffeld, P. Koivisto, N. Willi, T. C. Gasser, J. Kononen, G. Sauter, O. P. Kallioniemi, S. Srivastava, and H. B. Pollard. 2001. ANX7, a candidate tumor suppressor gene for prostate cancer. *Proc Natl Acad Sci USA*. 98:4575-4580.; Bockmuhl, U., S. Schmidt, S. Petersen, and I. Petersen. 2000. [Deletion of chromosome 10q—a marker for metastasis of head-neck carcinomas?]. *Laryngorhinootologie*. 79:81-85.; Morita, R., S. Saito, J. Ishikawa, O. Ogawa, O. Yoshida, K. Yamakawa, and Y. Nakamura. 1991. Common regions of deletion on chromosomes 5q, 6q, and 10q in renal cell carcinoma. *Cancer Res*. 51:5817-5820.; Jenkins, R. B., I. D. Hay, J. F. Herath, C. G. Schultz, J. L. Spurbeck, C. S. Grant, J. R. Goellner, and G. W. Dewald. 1990. Frequent occurrence of cytogenetic abnormalities in sporadic nonmedullary thyroid carcinoma. *Cancer*. 66:1213-1220.; Shen, W. P., R. F. Young, B. N. Walter, B. H. Choi, M. Smith, and J. Katz. 1990. Molecular analysis of a myxoid chondrosarcoma with rearrangements of chromosomes 10 and 22. *Cancer Genet Cytogenet*. 45:207-215.; Simpson, N. E., K. K. Kidd, P. J. Goodfellow, H. McDermid, S. Myers, J. R. Kidd, C. E. Jackson, A. M. Duncan, L. A. Farrer, K. Brasch, and et al. 1987. Assignment of multiple endocrine neoplasia type 2A to chromosome 10 by linkage. *Nature*. 328:528-530.; Ichimura, K., E. Schmidt, A. Miyakawa, H. Goike, and V. Collins. 1998. Distinct patterns of deletion on 10p and 10q suggest involvement of multiple tumor suppressor genes in the development of astrocytic gliomas of different malignancy grades. *Genes Chromosomes Cancer*. 22:9-15.; Kim, S., H. Fyrst, and J. Saba. 2000. Accumulation of phosphorylated sphingoid long chain bases results in cell growth inhibition in *Saccharomyces cerevisiae*. *Genetics*. 156:1519-1529.).

Lipid extraction is carried out by Ion-exchange chromatography and HPLC analysis. SK assays are performed essentially as described (Taylor, M. V. 2000. Muscle development: molecules of myoblast fusion. *Curr Biol*. 10:R646-648.). Purification of native and recombinant SK is performed essentially as described Mao, C., M. Wadleigh, G. Jenkins, Y. Hannun, and L. Obeid. 1997. Identification and characterization of *Saccharomyces cerevisiae* dihydrosphingosine-1-phosphate phosphatase. *J Biol Chem*. 272:28690-28694).

Example 16

Generation of a Transgenic *Drosophila melanogaster* Expression Human SPL and Human SPL-GFP Fusions Transgenic *Drosophila melanogaster* were generated that overexpress human SPL (cDNA set forth in SEQ ID NO:23; amino acid sequence set forth in SEQ ID NO:18) and human SPL-GFP fusion proteins using standard techniques as described herein. The transgenes were introduced into wild type Canton-S (BL-1), and Sply[05091] (BL-11393), mutant fly backgrounds.

From the foregoing, it will be appreciated that, although specific embodiments of the invention have been described herein for the purpose of illustration, various modifications may be made without deviating from the spirit and scope of the invention.

What is claimed is:

1. A method for identifying an individual with increased risk for having or developing colon or uterine cancer, comprising the steps of:
   (a) contacting a first biological sample comprising colon or uterine tissue comprising nucleic acid and being obtained from a patient suspected of having increased risk for having or developing colon or uterine cancer, with at least one oligonucleotide that is specific for the nucleic acid sequence as set forth in SEQ ID NO:23;
   (b) detecting a first amount of the oligonucleotide that hybridizes to the nucleic acid in the first sample; and
   (c) comparing the first amount of (b) to a second amount of the oligonucleotide that hybridizes to nucleic acid in a second biological sample from normal colon or uterine tissue,
   wherein a statistically significant decrease in the first amount relative to the second amount signifies increased risk for having or developing colon or uterine cancer in the individual.

* * * * *